(12) United States Patent
Huang et al.

(10) Patent No.: US 11,959,079 B2
(45) Date of Patent: Apr. 16, 2024

(54) METHODS FOR TREATING APOLIPOPROTEIN E4-ASSOCIATED DISORDERS

(71) Applicant: The J. David Gladstone Institutes, a testamentary trust established under the Will of J. David Gladstone, San Francisco, CA (US)

(72) Inventors: Yadong Huang, San Francisco, CA (US); Yaisa Andrews-Zwilling, San Francisco, CA (US)

(73) Assignee: The J. David Gladstone Institutes, a testamentary trust established under the of Will of J. David Gladstone, California (CA)

( * ) Notice: Subject to any disclaimer, the term of this patent is extended or adjusted under 35 U.S.C. 154(b) by 0 days.

(21) Appl. No.: 15/852,998

(22) Filed: Dec. 22, 2017

(65) Prior Publication Data

US 2018/0195068 A1    Jul. 12, 2018

Related U.S. Application Data

(63) Continuation of application No. 14/668,909, filed on Mar. 25, 2015, now Pat. No. 9,885,039, which is a continuation of application No. 12/958,057, filed on Dec. 1, 2010, now abandoned.

(60) Provisional application No. 61/356,977, filed on Jun. 21, 2010, provisional application No. 61/266,449, filed on Dec. 3, 2009.

(51) Int. Cl.
| | |
|---|---|
| *A61K 48/00* | (2006.01) |
| *A61K 31/7088* | (2006.01) |
| *A61K 35/30* | (2015.01) |
| *A61K 38/17* | (2006.01) |
| *A61P 25/28* | (2006.01) |
| *C12N 5/0797* | (2010.01) |
| *C12N 15/113* | (2010.01) |

(52) U.S. Cl.
CPC ........ *C12N 15/113* (2013.01); *A61K 31/7088* (2013.01); *A61K 35/30* (2013.01); *A61K 38/1716* (2013.01); *C12N 5/0623* (2013.01); *C12N 2310/14* (2013.01); *C12N 2320/32* (2013.01); *C12N 2510/00* (2013.01)

(58) Field of Classification Search
None
See application file for complete search history.

(56) References Cited

U.S. PATENT DOCUMENTS

| 7,655,785 B1* | 2/2010 | Bentwich | C12N 15/113 |
| | | | 536/24.1 |
| 9,885,039 B2 | 2/2018 | Huang et al. | |
| 2004/0241854 A1* | 12/2004 | Davidson | C12N 15/111 |
| | | | 435/455 |
| 2005/0181502 A1 | 8/2005 | Furcht et al. | |
| 2007/0116686 A1* | 5/2007 | Tamamaki | G01N 33/9426 |
| | | | 424/93.21 |
| 2008/0182813 A1* | 7/2008 | Honigman | C12N 15/111 |
| | | | 536/25.3 |
| 2009/0136456 A1 | 5/2009 | Huang et al. | |
| 2009/0170099 A1 | 7/2009 | Couillard-Despres et al. | |
| 2010/0297070 A1* | 11/2010 | Dugan | A61K 31/194 |
| | | | 424/85.2 |
| 2011/0135611 A1 | 6/2011 | Huang et al. | |
| 2011/0135613 A1 | 6/2011 | Huang et al. | |
| 2015/0267198 A1 | 9/2015 | Huang et al. | |

FOREIGN PATENT DOCUMENTS

| WO | WO 2005009359 | 2/2005 | |
| WO | WO-2005017143 A1 * | 2/2005 | ......... C07K 14/4711 |
| WO | WO 2007107789 | 9/2007 | |

OTHER PUBLICATIONS

Fastbom et al., Benzodiazepines may have protective effects against Alzheimer disease. Alzheimer Dis Assoc Disord. Mar. 1998;12(1):14-7. (Year: 1998).*
Dayer et al. New GABAergic interneurons in the adult neocortex and striatum are generated from different precursors (JCB, 2005, 168:415-427) (Year: 2005).*
Leonard et al., Does Epileptiform Activity Contribute to Cognitive Impairment in Alzheimer's Disease? Neuron, 2007, 55:677-678 ( Year: 2007).*
Cardoso et al., Tf-lipoplexes for neuronal siRNA delivery: A promising system to mediate gene silencing in the CNS. Journal of Controlled Release 132 (2008) 113-123 (Year: 2008).*
Brady et al., Parvalbumin-immunoreactive neurons in the hippocampal formation of Alzheimer's diseased brain. Neuroscience. vol. 80, Issue 4, Aug. 11, 1997, pp. 1113-1125 (Year: 1997).*
Fukuda et al., Quantitative analysis of GAD65 and GAD67 immunoreactivities in somata of GABAergic neurons in the mouse hippocampus proper (CA1 and CA3 regions), with special reference to parvalbumin-containing neurons. Brain Research 764, 1997. 237-243 (Year: 1997).*
Thakker D.R., et al. Neurochemical and behavioral consequences of widespread gene knockdown in the adult mouse brain by using nonviral RNA interference. Proc. Natl. Acad. Sci. U. S. A. 2004; 101:17270-17275 (Year: 2004).*

(Continued)

*Primary Examiner* — Arthur S Leonard

(74) *Attorney, Agent, or Firm* — Schwegman Lundberg & Woessner, P.A.

(57) ABSTRACT

The present disclosure provides a method of increasing the functionality of a GABAergic interneuron in the hilus of the hippocampus of an individual having at least one apolipoprotein E4 (apoE4) allele. The method generally involves reducing tau levels in the interneuron.

7 Claims, 16 Drawing Sheets

Specification includes a Sequence Listing.

(56) References Cited

OTHER PUBLICATIONS

Taliaz et al., Knockdown of brain-derived neurotrophic factor in specific brain sites precipitates behaviors associated with depression and reduces neurogenesis. Molecular Psychiatry vol. 15, pp. 80-92(2010), published on-line Jul. 21, 2009 (Year: 2010).*
Schraen-Maschke et al., Microtubule-associated protein tau gene: a risk factor in human neurodegenerative diseases. Neurobiology of Disease 15 (2004) 449-460 (Year: 2004).*
NCBI Reference Sequence: NM_005910.3. *Homo sapiens* microtubule-associated protein tau (MAPT), transcript variant 2, mRNA, May 25, 2008, pp. 1-3. (Year: 2008).*
Advokat, et al.; "Excitatory Amino Acids and Memory: Evidence from Research on Alzheimer's Disease and Behavioral Pharmacology"; Neuroscience & Biobehavioral Reviews; 1990; vol. 16, pp. 13-24.
Andrews-Zwilling, et al.; Apolipoprotein E4 Causes Age- and Tau-Dependent Impairment of GABAergic Interneurons, Leading to Learning and Memory Deficits in Mice; J Neurosci.; 30(41):13707-13717 (Oct. 13, 2010).
Brecht, et al.; "Neuron-specific apolipoprotein e4 proteolysis is associated with increased tau phosphorylation in brains of transgenic mice"; J Neurosci.; Mar. 10, 2004; 24(10):2527-34.
Brunden, et al.; "Advances in tau-focused drug discovery for Alzheimer's disease and related tauopathies"; Nature Reviews Drug Discovery; 8:783-793 (Oct. 2009).
Chhatwal, et al.; "Identification of cell-type-specific promoters within the brain using lentiviral vectors"; Gene Therapy; (2007) 14, 575-583.
Cobos, et al.; "Cellular Patterns of Transcription Factor Expression in Developing Cortical Interneurons"; Cerebral Cortex; 2006; V 16 Supplement, 7 pages.
Collinson, et al.; "An Inverse Agonist Selective for a5 Subunit-Containing GABAA Receptors Improves Encoding and Recall but not Consolidation in the Morris Water Maze"; Psychopharmacology; 2006; vol. 188, pp. 619-628.
Dawson, et al.; "An Inverse Agonist Selective for a5 Subunit-Containing GABAA Receptors Enhances Cognition"; The Journal of Pharmacology and Experimental Therapeutics; vol. 316, No. 3, pp. 1335-1345 (Dec. 2, 2005).
Dawson, et al.; "Inhibition of neuronal maturation in primary hippocampal neurons from tau deficient mice"; Journal of Cell Science; vol. 114, No. 6, pp. 1179-1187 (Jan. 2001).
Huang; "Abeta-independent roles of apolipoprotein E4 in the pathogenesis of Alzheimer's disease"; Trends Mol. Med.; 2010; 16(6):287-294.
Johansson, et al.; "Modelling of amyloid b-peptide induced lesions using roller-drum incubation of hippocampal slice cultures from neonatal rats"; Exp Brain Res (2006) 168: 11-24.
Kimmelman; "Clinical Review"; BMJ; 220:79-82 (Jan. 8, 2003).
Le Belle, et al.; "Stem Cells for Neurodegenerative Disorders, Where Can We Go From Here?"; BioDrugs; 16(6):389-401 (2002).
Lei, et al.; "Tau Deficiency Induces Parkinsonism with Dementia by Impairing APP-Mediated Iron Export"; Nature Medicine; Feb. 2012; vol. 18, No. 2, pp. 291-296.
Miller, et al.; "Targeting Alzheimer's disease genes with RNA interference: an effcient strategy for silencing mutant alleles"; Nucleic Acids Research; Jan. 30, 2004; vol. 32, No. 2, pp. 661-668.
Potter, et al.; "Generation of ere-transgenic Mice Using Dlx1/Dlx2 Enhancers and Their Characterization in GABAergic Interneurons"; Molecular & Cellular Neuroscience; 2009; vol. 40, pp. 167-186.
Raber, et al.; "ApoE genotype accounts for the vast majority of AD risk and AD pathology"; Neurobiol Aging; 2004; 25:641-650.
Ramos, et al.; "Early neuropathology of somatostatin/NPY GABAergic cells in the hippocampus of a PS1 x APP transgenic model of Alzheimer's disease"; Neurobiology of Aging; vol. 27, Issue 11, Nov. 2006, pp. 1658-1672.
Raper; "Gene therapy: The good, the bad, and the ugly"; Surgery, 137(5):487-492 (May 2005).
Roberson, et al.; "Reducing Endogenous Tau Ameliorates Amyloid B-Induced Deficits in an Alzheimer's Disease Mouse Model"; Science; 316:750-754 (May 4, 2007).
Tannenberg, et al.; "The Identification and Characterization of Excitotoxic Nerve-Endings in Alzheimer Disease"; Current Alzheimer Research; 2004; vol. 1, pp. 11-25.
Wernig, et al.; "Tau EGFP Embryonic Stem Cells: An Efficient Tool for Neuronal Lineage Selection and Transplantation"; J. Neuroscience Research; 69:918-924 (2002).
Lagnaouia, et al. (2002) "Benzodiazepine use and risk of dementia: A nested case-control study" J Clin Epidemiol. 55(3); pp. 314-318.
"U.S. Appl. No. 12/958,057, Advisory Action dated Nov. 18, 2013", 3 pgs.
"U.S. Appl. No. 12/958,057, Examiner Interview Summary dated Mar. 26, 2015", 4 pgs.
"U.S. Appl. No. 12/958,057, Examiner Interview Summary dated Oct. 11, 2013", 3 pgs.
"U.S. Appl. No. 12/958,057, Final Office Action dated May 20, 2013", 16 pgs.
"U.S. Appl. No. 12/958,057, Non Final Office Action dated Jan. 5, 2012", 14 pgs.
"U.S. Appl. No. 12/958,057, Non Final Office Action dated Sep. 17, 2012", 17 pgs.
"U.S. Appl. No. 12/958,057, Non Final Office Action dated Sep. 25, 2014", 23 pgs.
"U.S. Appl. No. 12/958,057, Response filed Jan. 22, 2013 to Non Final Office Action dated Sep. 17, 2012", 11 pgs.
"U.S. Appl. No. 12/958,057, Response filed May 4, 2012 to Non Final Office Action dated Jan. 5, 2012", 13 pgs.
"U.S. Appl. No. 12/958,057, Response filed Oct. 21, 2013 to Final Office Action dated May 20, 2013", 9 pgs.
"U.S. Appl. No. 14/668,909, Non Final Office Action dated Apr. 25, 2017", 13 pgs.
"U.S. Appl. No. 14/668,909, Non Final Office Action dated Jun. 20, 2016", 19 pgs.
"U.S. Appl. No. 14/668,909, Notice of Allowance dated Nov. 3, 2017", 8 pgs.
"U.S. Appl. No. 14/668,909, Response filed Mar. 25, 2016 to Restriction Requirement dated Sep. 28, 2015", 2 pgs.
"U.S. Appl. No. 14/668,909, Response filed Jul. 21, 2017 to Non Final Office Action dated Apr. 25, 2017", 6 pgs.
"U.S. Appl. No. 14/668,909, Response filed Dec. 7, 2016 to Non Final Office Action dated Jun. 20, 2016", 10 pgs.
"U.S. Appl. No. 14/668,909, Restriction Requirement dated Sep. 28, 2015", 9 pgs.
Dickey, et al., "Pharmacologic reductions of total tau levels; implications for the role of microtubule dynamics in regulating tau expression", Molecular Neurodegeneration 1:6, (2006), 1-9.
Freed, et al., "Will embryonic stem cells be a useful source of dopamine neurons for transplant into patients with Parkinson's disease?", PNAS, vol. 99 No. 4;, (Feb. 19, 2002), 1755-1757.
Liu, et al., "Amyloid-beta-induced toxicity of primary neurons is dependent upon differentiation-associated increases in tau and cyclin-dependent kinase 5 expression", J Neurochem. Feb;88(3):, (2004), 554-63.
Mahley, et al., "Apolipoprotein E4: A causative factor and therapeutic target in neuropathology, including Alzheimer's disease", PNAS, vol. 103, No. 15, (Apr. 11, 2006), 5644-5651.
Ruschenschmidt, et al., "Functional Properties of ES Cell-Derived Neurons Engrafted into the Hippocampus of Adult Normal and Chronically Epileptic Rats", Epilepsia, 46(Suppl. 5), (2005), 174-183.
Sullivan, M, "Phase II Findings in AD Drug Trial 'Not All Bad'", Clin Psychiatry News, 36, (2008), 34-35.
Xiao, et al., "Induced pluripotent stem cells in Parkinson's disease: scientific and clinical challenges", J Neural Neurosurg Psychiatry ;0:, (2015), 1-6.

* cited by examiner

```
catg agttgccat gttgagcagg actatttctg gcacttgcaa gtcccatgat
tccttcggta attctgaggg tgggggaag gacatgaaat catcttagot tagtttctg
tctgtgaatg tctatatagt gtattgtgtg tttaacaaa tgattacac tgactgtttgc
tgtaaaagtg aatttggaaa taaagttatt actctgat (nucleotides 6547-6758 of tau1 mRNA; SEQ ID NO:7)
```

FIG. 11A

```
acggccgagc ggcagggcgc ctgcgcgcgc ccactagtgg ccggaggaga aggctcccgc
ggaggccgcg ctgccccgcc tgccccctg ggaggctcgc gtccccgtcg ctcgggcctg
cgccgccgc cggcctcagg aacgggccct cttcgccggc gggcccctc gcagtcaccg
ccaccacca gtccggcac gtcccggcca caacagcagc gccgctgcca ccgcccacct tctgccgccg (nucleotides 1-240 of tau1 mRNA; SEQ ID NO:9)
```

FIG. 11B

SEQUENCE LISTING

<160> NUMBER OF SEQ ID NOS: 17

<210> SEQ ID NO 1
<211> LENGTH: 6762
<212> TYPE: DNA
<213> ORGANISM: Homo Sapiens

<400> SEQUENCE: 1

| | | | | | | |
|---|---|---|---|---|---|---|
| acggccgagc | ggcagggcgc | tcgcgcgcgc | ccactagtgg | ccggaggaga | aggctcccgc | 60 |
| ggaggccgcg | ctgcccgccc | cctcccctgg | ggaggctcgc | gttcccgctg | ctcgcgcctg | 120 |
| cgccgcccgc | cggcctcagg | aacgcgccct | cttcgccggc | gcgcgccctc | gcagtcaccg | 180 |
| ccacccacca | gctccggcac | caacagcagc | gccgctgcca | ccgcccacct | tctgccgccg | 240 |
| ccaccacagc | caccttctcc | tcctccgctg | tcctctcccg | tcctcgcctc | tgtcgactat | 300 |
| caggtgaact | ttgaaccagg | atggctgagc | cccgccagga | gttcgaagtg | atggaagatc | 360 |
| acgctgggac | gtacgggttg | ggggacagga | aagatcaggg | gggctacacc | atgcaccaag | 420 |
| accaagaggg | tgacacggac | gctggcctga | agaatctcc | cctgcagacc | cccactgagg | 480 |
| acggatctga | ggaaccgggc | tctgaaacct | ctgatgctaa | gagcactcca | acagcggaag | 540 |
| atgtgacagc | acccttagtg | gatgagggag | ctcccggcaa | gcaggctgcc | gcgcagcccc | 600 |
| acacggagat | cccagaagga | accacagctg | aagaagcagg | cattggagac | accccagcc | 660 |
| tggaagacga | agctgctggt | cacgtgaccc | aagagcctga | aagtggtaag | gtggtccagg | 720 |
| aaggcttcct | ccgagagcca | ggccccccag | gtctgagcca | ccagctcatg | tccggcatgc | 780 |
| ctgggctcc | cctcctgcct | gagggcccca | gagaggccac | acgccaacct | tcggggacag | 840 |
| gacctgagga | cacagagggc | ggccgccacg | ccctgagct | gctcaagcac | cagcttctag | 900 |
| gagacctgca | ccaggagggg | ccgccgctga | aggggcagg | gggcaaagag | aggccgggga | 960 |
| gcaaggagga | ggtggatgaa | gaccgcgacg | tcgatgagtc | ctcccccaa | gactcccctc | 1020 |
| cctccaaggc | ctccccagcc | caagatgggg | ggcctcccca | gacagccgcc | agagaagcca | 1080 |
| ccagcatccc | aggcttccca | gcggagggtg | ccatccccct | ccctgtggat | ttcctctcca | 1140 |
| aagtttccac | agagatccca | gcctcagagc | ccgacgggcc | cagtgtaggg | cgggccaaag | 1200 |
| ggcaggatgc | cccctggag | ttcacgtttc | acgtggaaat | cacacccaac | gtgcagaagg | 1260 |
| agcaggcgca | ctcggaggag | catttgggaa | gggctgcatt | tccaggggcc | cctggagagg | 1320 |
| ggccagaggc | ccggggcccc | tctttgggag | aggacacaaa | agaggctgac | cttccagagc | 1380 |
| cctctgaaaa | gcagcctgct | gctgctccgc | ggggggaagcc | cgtcagccgg | gtccctcaac | 1440 |
| tcaaagctcg | catggtcagt | aaaagcaaag | acgggactgg | aagcgatgac | aaaaaagcca | 1500 |
| agacatccac | acgttcctct | gctaaaaacct | tgaaaaatag | gccttgcctt | agccccaaac | 1560 |
| accccactcc | tggtagctca | gaccctctga | tccaaccctc | cagccctgct | gtgtgcccag | 1620 |
| agccaccttc | ctctcctaaa | cacgtctctt | ctgtcacttc | ccgaactggc | agttctggag | 1680 |
| caaaggagat | gaaactcaag | ggggctgatg | gtaaaacgaa | gatcgccaca | ccgcggggag | 1740 |
| cagccctcc | aggccagaag | ggccaggcca | acgccaccag | gattccagca | aaaacccgc | 1800 |
| ccgctccaaa | gacaccaccc | agctctggtg | aacctccaaa | atcaggggat | cgcagcggct | 1860 |
| acagcagccc | cggctcccca | ggcactcccg | gcagccgctc | ccgcacccg | tcccttccaa | 1920 |
| ccccacccac | ccggggagcc | aagaaggtgg | cagtggtccg | tactccaccc | aagtcgccgt | 1980 |
| cttccgccaa | gagccgcctg | cagacagccc | ccgtgcccat | gccagacctg | aagaatgtca | 2040 |
| agtccaagat | cggctccact | gagaacctga | agcaccagcc | gggaggcggg | aaggtgcaga | 2100 |

```
taattaataa gaagctggat cttagcaacg tccagtccaa gtgtggctca aaggataata    2160
tcaaacacgt cccgggaggc ggcagtgtgc aaatagtcta caaaccagtt gacctgagca    2220
aggtgacctc caagtgtggc tcattaggca acatccatca taaaccagga ggtggccagg    2280
tggaagtaaa atctgagaag cttgacttca aggacagagt ccagtcgaag attgggtccc    2340
tggacaatat cacccacgtc cctggcggag gaaataaaaa gattgaaacc cacaagctga    2400
ccttccgcga gaacgccaaa gccaagacag accacggggc ggagatcgtg tacaagtcgc    2460
cagtggtgtc tggggacacg tctccacggc atctcagcaa tgtctcctcc accggcagca    2520
tcgacatggt agactcgccc cagctcgcca cgctagctga cgaggtgtct gcctccctgg    2580
ccaagcaggg tttgtgatca ggcccctggg gcggtcaata attgtggaga ggagagaatg    2640
agagagtgtg gaaaaaaaaa gaataatgac ccggcccccg ccctctgccc ccagctgctc    2700
ctcgcagttc ggttaattgg ttaatcactt aacctgcttt tgtcactcgg ctttggctcg    2760
ggacttcaaa atcagtgatg ggagtaagag caaatttcat cttttccaaat tgatgggtgg   2820 gctagtaata aaatatttaa aaaaaaacat tcaaaaacat ggccacatcc aacatttcct    2880
caggcaattc cttttgattc ttttttcttc cccctccatg tagaagaggg agaaggagag    2940
gctctgaaag ctgcttctgg gggatttcaa gggactgggg gtgccaacca cctctggccc    3000
tgttgtgggg gtgtcacaga ggcagtggca gcaacaaagg atttgaaact tggtgtgttc    3060
gtggagccac aggcagacga tgtcaacctt gtgtgagtgt gacggggggtt ggggtggggc    3120 gggaggccac gggggaggcc gaggcagggg ctgggcagag gggagaggaa gcacaagaag    3180
tgggagtggg agaggaagcc acgtgctgga gagtagacat ccccctcctt gccgctggga    3240
gagccaaggc ctatgccacc tgcagcgtct gagcggccgc ctgtccttgg tggccggggg    3300
tgggggcctg ctgtgggtca gtgtgccacc ctctgcaggg cagcctgtgg gagaagggac    3360
agcgggtaaa aagagaaggc aagctggcag gagggtggca cttcgtggat gacctcctta    3420
gaaaagactg accttgatgt cttgagagcg ctggcctctt cctccctccc tgcagggtag    3480
ggggcctgag ttgaggggct tccctctgct ccacagaaac cctgtttat tgagttctga     3540 aggttggaac tgctgccatg attttggcca cttttgcagac ctgggacttt agggctaacc   3600
agttctcttt gtaaggactt gtgcctcttg ggagacgtcc acccgtttcc aagcctgggc    3660
cactggcatc tctggagtgt gtggggtct gggaggcagg tcccgagccc cctgtccttc     3720
ccacggccac tgcagtcacc cctgtctgcg ccgctgtgct gttgtctgcc gtgagagccc    3780
aatcactgcc tataccccct catcacacgtc acaatgtccc gaattcccag cctcaccacc    3840
ccttctcagt aatgaccctg gttggttgca ggaggtacct actccatact gagggtgaaa    3900
ttaagggaag gcaaagtcca ggcacaagag tgggacccca gcctctcact ctcagttcca    3960
ctcatccaac tgggaccctc accacgaatc tcatgatctg attcggttcc ctgtctcctc    4020
ctcccgtcac agatgtgagc cagggcactg ctcagctgtg accctaggtg tttctgcctt    4080
gttgacatgg agagagccct ttcccctgag aaggcctggc ccttcctgt gctgagccca     4140 cagcagcagg ctgggtgtct tggttgtcag tggtggcacc aggatggaag gcaaggcac     4200 ccagggcagg cccacagtcc cgctgtcccc cacttgcacc ctagcttgta gctgccaacc    4260
tcccagacag cccagcccgc tgctcagctc cacatgcata gtatcagccc tccacacccg    4320
acaaagggga acacaccccc ttggaaatgg ttcttttccc ccagtcccag ctggaagcca    4380
tgctgtctgt tctgctggag cagctgaaca tatacataga tgttgccctg ccctcccat     4440
```

-continued

```
ctgcaccctg ttgagttgta gttggatttg tctgtttatg cttggattca ccagagtgac    4500
tatgatagta aaaagaaaaa aaaaaaaaaa aaaggacgca tgtatcttga aatgcttgta    4560
aagaggtttc taacccaccc tcacgaggtg tctctcaccc ccacactggg actcgtgtgg    4620
cctgtgtggt gccaccctgc tggggcctcc caagttttga aaggctttcc tcagcacctg    4680
ggacccaaca gagaccagct tctagcagct aaggaggccg ttcagctgtg acgaaggcct    4740
gaagcacagg attaggactg aagcgatgat gtccccttcc ctacttcccc ttggggctcc    4800
ctgtgtcagg gcacagacta ggtcttgtgg ctggtctggc ttgcggcgcg aggatggttc    4860
tctctggtca tagcccgaag tctcatggca gtcccaaagg aggcttacaa ctcctgcatc    4920
acaagaaaaa ggaagccact gccagctggg gggatctgca gctcccagaa gctccgtgag    4980
cctcagccac ccctcagact gggttcctct ccaagctcgc cctctggagg ggcagcgcag    5040
cctcccacca agggccctgc gaccacagca gggattggga tgaattgcct gtcctggatc    5100
tgctctagag gcccaagctg cctgcctgag aaggatgac ttgacaagtc aggagacact    5160
gttcccaaag ccttgaccag agcacctcag cccgctgacc ttgcacaaac tccatctgct    5220
gccatgagaa aagggaagcc gccttttgcaa aacattgctg cctaaagaaa ctcagcagcc    5280
tcaggcccaa ttctgccact tctggttttgg gtacagttaa aggcaacct gagggacttg    5340
gcagtagaaa tccagggcct cccctggggc tggcagcttc gtgtgcagct agagctttac    5400
ctgaaaggaa gtctctgggc ccagaactct ccaccaagag cctccctgcc gttcgctgag    5460
tcccagcaat tctcctaagt tgaagggatc tgagaaggag aaggaaatgt ggggtagatt    5520
tggtggtggt tagagatatg ccccccctcat tactgccaac agtttcggct gcatttcttc    5580
acgcacctcg gttcctcttc ctgaagttct tgtgccctgc tcttcagcac catgggcctt    5640
cttatacgga aggctctggg atctcccct tgtgggggca ggctcttggg gccagcctaa    5700
gatcatggtt tagggtgatc agtgctggca gataaattga aaaggcacgc tggcttgtga    5760
tcttaaatga ggacaatccc cccagggctg ggcactcctc ccctcccctc acttctccca    5820
cctgcagagc cagtgtcctt gggtgggcta gataggatat actgtatgcc ggctccttca    5880
agctgctgac tcacttttatc aatagttcca tttaaattga cttcagtggt gagactgtat    5940
cctgtttgct attgcttgtt gtgctatggg gggagggggg aggaatgtgt aagatagtta    6000
acatgggcaa agggagatct tggggtgcag cacttaaact gcctcgtaac ccttttcatg    6060
atttcaacca catttgctag agggagggag cagccacgga gttagaggcc cttggggttt    6120
ctcttttcca ctgacaggct ttcccaggca gctggctagt tcattccctc cccagccagg    6180
tgcaggcgta ggaatatgga catctggttg ctttggcctg ctgccctctt tcagggggtcc    6240
taagcccaca atcatgcctc cctaagacct tggcatcctt ccctctaagc cgttggcacc    6300
tctgtgccac ctctcacact ggctccagac acacagcctg tgcttttgga gctgagatca    6360
ctcgcttcac cctcctcatc tttgttctcc aagtaaagcc acgaggtcgg ggcgagggca    6420
gaggtgatca cctgcgtgtc ccatctacag acctgcggct tcataaaact tctgatttct    6480
cttcagcttt gaaaagggtt accctgggca ctggcctaga gcctcacctc ctaatagact    6540
tagccccatg agtttgccat gttgagcagg actatttctg gcacttgcaa gtcccatgat    6600
ttcttcggta attctgaggg tgggggagg gacatgaaat catcttagct tagctttctg    6660
tctgtgaatg tctatatagt gtattgtgtg ttttaacaaa tgatttacac tgactgttgc    6720
tgtaaaagtg aatttggaaa taaagttatt actctgatta aa                        6762
```

<210> SEQ ID NO 2
<211> LENGTH: 5811
<212> TYPE: DNA
<213> ORGANISM: Homo Sapiens

<400> SEQUENCE: 2

| | | | | | |
|---|---|---|---|---|---|
| acggccgagc | ggcagggcgc | tcgcgcgcgc | ccactagtgg | ccggaggaga | aggctcccgc | 60 |
| ggaggccgcg | ctgcccgccc | cctcccctgg | ggaggctcgc | gttcccgctg | ctcgcgcctg | 120 |
| cgccgcccgc | cggcctcagg | aacgcgccct | cttcgccggc | gcgcgccctc | gcagtcaccg | 180 |
| ccacccacca | gctccggcac | caacagcagc | gccgctgcca | ccgcccacct | tctgccgccg | 240 |
| ccaccacagc | caccttctcc | tcctccgctg | tcctctcccg | tcctcgcctc | tgtcgactat | 300 |
| caggtgaact | ttgaaccagg | atggctgagc | cccgccagga | gttcgaagtg | atggaagatc | 360 |
| acgctgggac | gtacggggttg | ggggacagga | aagatcaggg | gggctacacc | atgcaccaag | 420 |
| accaagaggg | tgacacggac | gctggcctga | agaatctccc | cctgcagacc | cccactgagg | 480 |
| acggatctga | ggaaccgggc | tctgaaacct | ctgatgctaa | gagcactcca | acagcggaag | 540 |
| atgtgacagc | acccttagtg | gatgagggag | ctcccggcaa | gcaggctgcc | gcgcagcccc | 600 |
| acacggagat | cccagaagga | accacagctg | aagaagcagg | cattggagac | accccagcc | 660 |
| tggaagacga | agctgctggt | cacgtgaccc | aagctcgcat | ggtcagtaaa | agcaaagacg | 720 |
| ggactggaag | cgatgacaaa | aaagccaagg | gggctgatgg | taaaacgaag | atcgccacac | 780 |
| cgcggggagc | agcccctcca | ggccagaagg | gccaggccaa | cgccaccagg | attccagcaa | 840 |
| aaacccccgcc | cgctccaaag | acaccaccca | gctctggtga | acctccaaaa | tcaggggatc | 900 |
| gcagcggcta | cagcagcccc | ggctccccag | gcactcccgg | cagccgctcc | cgcacccgt | 960 |
| cccttccaac | cccacccacc | cgggagccca | agaaggtggc | agtggtccgt | actccaccca | 1020 |
| agtcgccgtc | ttccgccaag | agccgcctgc | agacagcccc | cgtgcccatg | ccagacctga | 1080 |
| agaatgtcaa | gtccaagatc | ggctccactg | agaacctgaa | gcaccagccg | ggaggcggga | 1140 |
| aggtgcagat | aattaataag | aagctggatc | ttagcaacgt | ccagtccaag | tgtggctcaa | 1200 |
| aggataatat | caaacacgtc | ccgggaggcg | gcagtgtgca | aatagtctac | aaaccagttg | 1260 |
| acctgagcaa | ggtgacctcc | aagtgtggct | cattaggcaa | catccatcat | aaaccaggag | 1320 |
| gtggccaggt | ggaagtaaaa | tctgagaagc | ttgacttcaa | ggacagagtc | cagtcgaaga | 1380 |
| ttgggtccct | ggacaatatc | acccacgtcc | ctggcggagg | aaataaaaag | attgaaaccc | 1440 |
| acaagctgac | cttccgcgag | aacgccaaag | ccaagacaga | ccacggggcg | gagatcgtgt | 1500 |
| acaagtcgcc | agtggtgtct | ggggacacgt | ctccacggca | tctcagcaat | gtctcctcca | 1560 |
| ccggcagcat | cgacatggta | gactcgcccc | agctcgccac | gctagctgac | gaggtgtctg | 1620 |
| cctccctggc | caagcagggt | ttgtgatcag | gcccctgggg | cggtcaataa | ttgtggagag | 1680 |
| gagagaatga | gagagtgtgg | aaaaaaaaag | aataatgacc | cggccccgc | cctctgcccc | 1740 |
| cagctgctcc | tcgcagttcg | gttaattggt | taatcactta | acctgctttt | gtcactcggc | 1800 |
| tttggctcgg | gacttcaaaa | tcagtgatgg | gagtaagagc | aaatttcatc | tttccaaatt | 1860 |
| gatgggtggg | ctagtaataa | aatatttaaa | aaaaaacatt | caaaaacatg | gccacatcca | 1920 |
| acatttcctc | aggcaattcc | ttttgattct | tttttcttcc | ccctccatgt | agaagaggga | 1980 |
| gaaggagagg | ctctgaaagc | tgcttctggg | ggatttcaag | ggactggggg | tgccaaccac | 2040 |
| ctctggcct | gttgtggggg | tgtcacagag | gcagtggcag | caacaaagga | tttgaaactt | 2100 |
| ggtgtgttcg | tggagccaca | ggcagacgat | gtcaaccttg | tgtgagtgtg | acggggttg | 2160 |

```
gggtggggcg ggaggccacg ggggaggccg aggcaggggc tgggcagagg ggagaggaag    2220
cacaagaagt gggagtggga gaggaagcca cgtgctggag agtagacatc cccctccttg    2280
ccgctgggag agccaaggcc tatgccacct gcagcgtctg agcggccgcc tgtccttggt    2340
ggccgggggt ggggggcctgc tgtgggtcag tgtgccaccc tctgcagggc agcctgtggg   2400
agaagggaca gcgggtaaaa agagaaggca agctggcagg agggtggcac ttcgtggatg    2460
acctccttag aaaagactga ccttgatgtc ttgagagcgc tggcctcttc ctccctccct    2520
gcagggtagg gggcctgagt tgaggggctt ccctctgctc cacagaaacc ctgttttatt    2580
gagttctgaa ggttggaact gctgccatga ttttggccac tttgcagacc tgggacttta    2640
gggctaacca gttctctttg taaggacttg tgcctcttgg gagacgtcca cccgtttcca    2700
agcctgggcc actggcatct ctggagtgtg tggggtctg gaggcaggt cccgagcccc     2760 ctgtccttcc cacggccact gcagtcaccc ctgtctgcgc cgctgtgctg ttgtctgccg    2820
tgagagccca atcactgcct ataccctca tcacacgtca caatgtcccg aattcccagc     2880
ctcaccaccc cttctcagta atgaccctgg ttggttgcag gaggtaccta ctccatactg    2940
agggtgaaat taagggaagg caaagtccag gcacaagagt gggacccag cctctcactc     3000 tcagttccac tcatccaact gggaccctca ccacgaatct catgatctga ttcggttccc    3060
tgtctcctcc tcccgtcaca gatgtgagcc agggcactgc tcagctgtga ccctaggtgt    3120
ttctgccttg ttgacatgga gagagccctt ccccctgaga aggcctggcc ccttcctgtg    3180
ctgagcccac agcagcaggc tgggtgtctt ggttgtcagt ggtggcacca ggatggaagg    3240
gcaaggcacc cagggcaggc ccacagtccc gctgtccccc acttgcaccc tagcttgtag    3300
ctgccaacct cccagacagc ccagcccgct gctcagctcc acatgcatag tatcagccct    3360
ccacacccga caaggggaa cacacccct tggaaatggt tcttttcccc cagtcccagc      3420
tggaagccat gctgtctgtt ctgctggagc agctgaacat atacatagat gttgccctgc    3480 cctcccatc tgcaccctgt tgagttgtag ttggatttgt ctgtttatgc cttggattcac   3540 cagagtgact atgatagtga aaagaaaaaa aaaaaaaaaa aaggacgcat gtatcttgaa    3600
atgcttgtaa agaggtttct aacccaccct cacgaggtgt ctctcacccc cacactggga   3660
ctcgtgtggc ctgtgtggtg ccaccctgct ggggcctccc aagttttgaa aggctttcct   3720
cagcacctgg gacccaacag agaccagctt ctagcagcta aggaggccgt tcagctgtga   3780
cgaaggcctg aagcacagga ttaggactga agcgatgatg tccccttccc tacttcccct   3840
tggggctccc tgtgtcaggg cacagactag gtcttgtggc tggtctggct gcggcgcga    3900 ggatggttct ctctggtcat agcccgaagt ctcatggcag tcccaaagga ggcttacaac    3960
tcctgcatca caagaaaag gaagccactg ccagctgggg ggatctgcag ctcccagaag   4020
ctccgtgagc ctcagccacc cctcagactg ggttcctctc caagctcgcc ctctggaggg   4080
gcagcgcagc ctcccaccaa gggccctgcg accacagcag ggattgggat gaattgcctg   4140
tcctggatct gctctagagg cccaagctgc ctgcctgagg aaggatgact tgacaagtca    4200
ggagacactg ttcccaaagc cttgaccaga gcacctcagc ccgctgacct tgcacaaact   4260
ccatctgctg ccatgagaaa agggaagccg ccttttgcaaa acattgctgc ctaaagaaac   4320
tcagcagcct caggcccaat tctgccactt ctggtttggg tacagttaaa ggcaaccctg   4380
agggacttgg cagtagaaat ccagggcctc cctgggggct ggcagcttcg tgtgcagcta    4440
gagctttacc tgaaaggaag tctctgggcc cagaactctc caccaagagc ctccctgccg   4500
ttcgctgagt cccagcaatt ctcctaagtt gaagggatct gagaaggaga aggaaatgtg    4560
```

```
gggtagattt ggtggtggtt agagatatgc cccccctcatt actgccaaca gtttcggctg   4620
catttcttca cgcacctcgg ttcctcttcc tgaagttctt gtgccctgct cttcagcacc   4680
atgggccttc ttatacggaa ggctctggga tctcccccctt gtgggggcag gctcttgggg   4740
ccagcctaag atcatggttt agggtgatca gtgctggcag ataaattgaa aaggcacgct   4800
ggcttgtgat cttaaatgag gacaatcccc ccagggctgg gcactcctcc cctcccctca   4860
cttctcccac ctgcagagcc agtgtccttg ggtgggctag ataggatata ctgtatgccg   4920
gctccttcaa gctgctgact cactttatca atagttccat ttaaattgac ttcagtggtg   4980
agactgtatc ctgtttgcta ttgcttgttg tgctatgggg ggaggggggga ggaatgtgta   5040 agatagttaa catgggcaaa gggagatctt ggggtgcagc acttaaactg cctcgtaacc   5100
cttttcatga tttcaaccac atttgctaga gggagggagc agccacggag ttagaggccc   5160
ttggggtttc tcttttccac tgacaggctt tcccaggcag ctggctagtt cattccctcc   5220
ccagccaggt gcaggcgtag gaatatggac atctggttgc tttggcctgc tgccctcttt   5280
caggggtcct aagcccacaa tcatgcctcc ctaagaccct ggcatccttc cctctaagcc   5340
gttggcacct ctgtgccacc tctcacactg gctccagaca cacagcctgt gcttttggag   5400
ctgagatcac tcgcttcacc ctcctcatct ttgttctcca agtaaagcca cgaggtcggg   5460
gcgagggcag aggtgatcac ctgcgtgtcc catctacaga cctgcggctt cataaaactt   5520
ctgatttctc ttcagctttg aaaagggtta ccctgggcac tggcctagag cctcacctcc   5580
taatagactt agccccatga gtttgccatg ttgagcagga ctatttctgg cacttgcaag   5640
tcccatgatt tcttcggtaa ttctgagggt gggggagggg acatgaaatc atcttagctt   5700
agctttctgt ctgtgaatgt ctatatagtg tattgtgtgt tttaacaaat gatttacact   5760
gactgttgct gtaaaagtga atttggaaat aaagttatta ctctgattaa a             5811
```

<210> SEQ ID NO 3
<211> LENGTH: 5637
<212> TYPE: DNA
<213> ORGANISM: Homo Sapiens

<400> SEQUENCE: 3

```
acggccgagc ggcagggcgc tcgcgcgcgc ccactagtgg ccggaggaga aggctcccgc     60
ggaggccgcg ctgccgccc cctccccctgg ggaggctcgc gttccccgctg ctcgcgcctg   120 cgccgcccgc cggcctcagg aacgcgccct cttcgccggc gcgcgccctc gcagtcaccg   180
ccacccacca gctccggcac caacagcagc gccgctgcca ccgcccacct tctgcgccg    240 ccaccacagc caccttctcc tcctccgctg tcctctcccg tcctcgcctc tgtcgactat   300
caggtgaact ttgaaccagg atggctgagc ccgccaggga gttcgaagtg atggaagatc   360
acgctgggac gtacgggttg ggggacagga aagatcaggg gggctacacc atgcaccaag   420
accaagaggg tgacacggac gctggcctga agctgaaga gcaggcatt ggagacaccc     480 ccagcctgga agacgaagct gctggtcacg tgacccaagc tcgcatggtc agtaaaagca   540
aagacgggac tggaagcgat gacaaaaaag ccaggggggc tgatggtaaa acgaagatcg   600
ccacaccgcg gggagcagcc cctccaggcc agaagggcca ggcaacgcc accaggattc    660 cagcaaaaac cccgcccgct ccaaagacac cacccagctc tggtgaacct ccaaaatcag   720
gggatcgcag cggctacagc agccccgct ccccaggcac tcccgggagc cgctcccgca   780
ccccgtccct tccaaccca cccacccggg agcccaagaa ggtggcagtg gtccgtactc   840
```

```
cacccaagtc gccgtcttcc gccaagagcc gcctgcagac agccccgtg cccatgccag    900 acctgaagaa tgtcaagtcc aagatcggct ccactgagaa cctgaagcac agccgggag    960 gcgggaaggt gcagataatt aataagaagc tggatcttag caacgtccag tccaagtgtg   1020
gctcaaagga taatatcaaa cacgtcccgg gaggcggcag tgtgcaaata gtctacaaac   1080
cagttgacct gagcaaggtg acctccaagt gtggctcatt aggcaacatc catcataaac   1140
caggaggtgg ccaggtggaa gtaaaatctg agaagcttga cttcaaggac agagtccagt   1200
cgaagattgg gtccctggac aatatcaccc acgtccctgg cggaggaaat aaaaagattg   1260
aaacccacaa gctgaccttc cgcgagaacg ccaaagccaa gacagaccac ggggcggaga   1320
tcgtgtacaa gtcgccagtg gtgtctgggg acacgtctcc acggcatctc agcaatgtct   1380
cctccaccgg cagcatcgac atggtagact cgcccagct cgccacgcta gctgacgagg    1440
tgtctgcctc cctggccaag cagggtttgt gatcaggccc ctgggcggt caataattgt     1500 ggagaggaga gaatgagaga gtgtggaaaa aaaagaata atgacccggc ccccgccctc     1560
tgcccccagc tgctcctcgc agttcggtta attggttaat cacttaacct gcttttgtca    1620
ctcggctttg gctcgggact tcaaaatcag tgatgggagt aagagcaaat ttcatctttc   1680
caaattgatg ggtgggctag taataaaata tttaaaaaaa aacattcaaa aacatggcca   1740
catccaacat ttcctcaggc aattcctttt gattcttttt tcttccccct ccatgtagaa   1800
gagggagaag gagaggctct gaaagctgct tctgggggat ttcaagggac tgggggtgcc   1860
aaccacctct ggccctgttg tgggggtgtc acagaggcag tggcagcaac aaaggatttg   1920
aaacttggtg tgttcgtgga gccacaggca gacgatgtca accttgtgtg agtgtgacgg   1980 gggttgggt ggggcgggag ccacggggg aggccgaggc aggggctggg cagaggggag     2040
aggaagcaca agaagtggga gtgggagagg aagccacgtg ctggagagta gacatccccc   2100
tccttgccgc tgggagagcc aaggcctatg ccacctgcag cgtctgagcg gccgcctgtc   2160
cttggtggcc ggggtgggg gcctgctgtg ggtcagtgtg ccaccctctg cagggcagcc     2220
tgtgggagaa gggacagcgg gtaaaaagag aaggcaagct ggcaggaggg tggcacttcg   2280
tggatgacct ccttagaaaa gactgacctt gatgtcttga gagcgctggc ctcttcctcc   2340
ctccctgcag ggtaggggc ctgagttgag gggcttccct ctgctccaca gaaaccctgt    2400
tttattgagt tctgaaggtt ggaactgctg ccatgatttt ggccactttg cagacctggg   2460
actttagggc taaccagttc tctttgtaag gacttgtgcc tcttgggaga cgtccacccg   2520
tttccaagcc tgggccactg gcatctctgg agtgtgtggg ggtctgggag gcaggtcccg   2580
agccccctgt ccttcccacg gccactgcag tcaccctgt ctgcgccgct gtgctgttgt    2640
ctgccgtgag agcccaatca ctgcctatac ccctcatcac acgtcacaat gtcccgaatt   2700
cccagcctca ccacccttc tcagtaatga ccctggttgg ttgcaggagg tacctactcc    2760
atactgaggg tgaaattaag ggaaggcaaa gtccaggcac aagagtggga ccccagcctc   2820
tcactctcag ttccactcat ccaactggga ccctcaccac gaatctcatg atctgattcg   2880
gttccctgtc tcctcctccc gtcacagatg tgagccaggg cactgctcag ctgtgaccct   2940
aggtgtttct gccttgttga catggagaga gccctttccc ctgagaaggc ctggcccctt   3000
cctgtgctga gccacagca gcaggctggg tgtcttggtt gtcagtggtg gcaccaggat    3060
ggaagggcaa ggcacccagg gcaggcccac agtcccgctg tccccacttc gcaccctagc   3120
ttgtagctgc caacctccca gacagcccag cccgctgctc agctccacat gcatagtatc   3180
agccctccac acccgacaaa ggggaacaca ccccccttgga aatggttctt ttcccccagt   3240
```

```
cccagctgga agccatgctg tctgttctgc tggagcagct gaacatatac atagatgttg    3300
ccctgccctc cccatctgca ccctgttgag ttgtagttgg atttgtctgt ttatgcttgg    3360
attcaccaga gtgactatga tagtgaaaag aaaaaaaaaa aaaaaaaagg acgcatgtat    3420
cttgaaatgc ttgtaaagag gtttctaacc caccctcacg aggtgtctct caccccacca    3480
ctgggactcg tgtggcctgt gtggtgccac cctgctgggg cctcccaagt tttgaaaggc    3540
tttcctcagc acctgggacc caacagagac cagcttctag cagctaagga ggccgttcag    3600
ctgtgacgaa ggcctgaagc acaggattag gactgaagcg atgatgtccc cttccctact    3660
tcccctgggg gctccctgtg tcagggcaca gactaggtct tgtggctggt ctggcttgcg    3720
gcgcgaggat ggttctctct ggtcatagcc cgaagtctca tggcagtccc aaaggaggct    3780
tacaactcct gcatcacaag aaaaaggaag ccactgccag ctgggggat ctgcagctcc    3840 cagaagctcc gtgagcctca gccacccctc agactgggtt cctctccaag ctcgccctct    3900
ggaggggcag cgcagcctcc caccaagggc cctgcgacca cagcagggat tgggatgaat    3960
tgcctgtcct ggatctgctc tagaggccca agctgcctgc ctgaggaagg atgacttgac    4020
aagtcaggag acactgttcc caaagccttg accagagcac ctcagcccgc tgaccttgca    4080
caaactccat ctgctgccat gagaaaaggg aagccgcctt tgcaaaacat tgctgcctaa    4140
agaaactcag cagcctcagg cccaattctg ccacttctgg tttgggtaca gttaaaggca    4200
accctgaggg acttggcagt agaaatccag ggcctcccct ggggctggca gcttcgtgtg    4260
cagctagagc tttacctgaa aggaagtctc tgggcccaga actctccacc aagagcctcc    4320
ctgccgttcg ctgagtccca gcaattctcc taagttgaag ggatctgaga aggagaagga    4380
aatgtggggt agatttggtg gtggttagag atatgccccc ctcattactg ccaacagttt    4440
cggctgcatt tcttcacgca cctcggttcc tcttcctgaa gttcttgtgc cctgctcttc    4500
agcaccatgg gccttcttat acggaaggct ctgggatctc cccttgtgg gggcaggctc    4560 ttggggccag cctaagatca tggtttaggg tgatcagtgc tggcagataa attgaaaagg    4620
cacgctggct tgtgatctta aatgaggaca atcccccag ggctgggcac tcctcccctc    4680
ccctcacttc tcccacctgc agagccagtg tccttgggtg ggctagatag gatatactgt    4740
atgccggctc cttcaagctg ctgactcact ttatcaatag ttccatttaa attgacttca    4800
gtggtgagac tgtatcctgt ttgctattgc ttgttgtgct atgggggag ggggaggaa    4860 tgtgtaagat agttaacatg ggcaaaggga gatcttgggg tgcagcactt aaactgcctc    4920
gtaacccttt tcatgatttc aaccacattt gctagaggga gggagcagcc acggagttag    4980
aggcccttgg ggtttctctt ttccactgac aggctttccc aggcagctgg ctagttcatt    5040
ccctccccag ccaggtgcag gcgtaggaat atggacatct ggttgctttg gcctgctgcc    5100
ctctttcagg ggtcctaagc ccacaatcat gcctccctaa gaccttggca tccttccctc    5160
taagccgttg gcacctctgt gccacctctc acactggctc cagacacaca gcctgtgctt    5220
ttggagctga gatcactcgc ttcaccctcc tcatctttgt tctccaagta aagccacgag    5280
gtcggggcga gggcagaggt gatcacctgc gtgtcccatc tacagacctg cggcttcata    5340
aaacttctga tttctcttca gctttgaaaa gggttaccct gggcactggc ctagagcctc    5400
acctcctaat agacttagcc ccatgagttt gccatgttga gcaggactat ttctggcact    5460
tgcaagtccc atgatttctt cggtaattct gagggtgggg ggaggacat gaaatcatct    5520 tagcttagct ttctgtctgt gaatgtctat atagtgtatt gtgtgtttta acaaatgatt    5580
```
tacactgact gttgctgtaa aagtgaattt ggaaataaag ttattactct gattaaa    5637

<210> SEQ ID NO 4
<211> LENGTH: 5544
<212> TYPE: DNA
<213> ORGANISM: Homo Sapiens

<400> SEQUENCE: 4
acggccgagc ggcagggcgc tcgcgcgcgc ccactagtgg ccggaggaga aggctcccgc      60
ggaggccgcg ctgcccgccc cctcccctgg ggaggctcgc gttcccgctg ctcgcgcctg     120
cgccgcccgc cggcctcagg aacgcgccct cttcgccggc gcgcgccctc gcagtcaccg     180
ccacccacca gctccggcac aacagcagc gccgctgcca ccgcccacct tctgccgccg      240
ccaccacagc caccttctcc tcctccgctg tcctctcccg tcctcgcctc tgtcgactat     300
caggtgaact ttgaaccagg atggctgagc ccgccaggag gttcgaagtg atggaagatc     360
acgctgggac gtacggggttg ggggacagga aagatcaggg gggctacacc atgcaccaag     420
accaagaggg tgacacggac gctggcctga agctgaagaa agcaggcatt ggagacaccc      480
ccagcctgga agacgaagct gctggtcacg tgacccaagc tcgcatggtc agtaaaagca     540
aagacgggac tggaagcgat gacaaaaaag ccaagggggc tgatggtaaa acgaagatcg     600
ccacaccgcg gggagcagcc cctccaggcc agaagggcca ggccaacgcc accaggattc     660
cagcaaaaac cccgcccgct ccaaagacac cacccagctc tggtgaacct ccaaaatcag     720
gggatcgcag cggctacagc agcccccggct ccccaggcac tcccggcagc cgctcccgca     780
ccccgtccct tccaaccccca cccacccggg agcccaagaa ggtggcagtg gtccgtactc     840
cacccaagtc gccgtcttcc gccaagagcc gcctgcagac agcccccgtg cccatgccag     900
acctgaagaa tgtcaagtcc aagatcggcc ccactgagaa cctgaagcac cagccgggag     960
gcgggaaggt gcaaatagtc tacaaaccag ttgacctgag caaggtgacc tccaagtgtg    1020
gctcattagg caacatccat cataaaccag gaggtggcca ggtggaagta aaatctgaga    1080
agcttgactt caaggacaga gtccagtcga agattgggtc cctggacaat atcacccacg    1140
tccctggcgg aggaaataaa aagattgaaa cccacaagct gaccttccgc gagaacgcca    1200
aagccaagac agaccacggg gcggagatcg tgtacaagtc gccagtggtg tctggggaca    1260
cgtctccacg gcatctcagc aatgtctcct ccaccggcag catcgacatg gtagactcgc    1320
cccagctcgc cacgctagct gacgaggtgt ctgcctccct ggccaagcag ggtttgtgat    1380
caggcccctg gggcggtcaa taattgtgga gaggagagaa tgagagagtg tggaaaaaaa    1440
aagaataatg accggccccc cgccctctgc ccccagctgc tcctcgcagt tcggttaatt    1500
ggttaatcac ttaacctgct tttgtcactc ggctttggct cgggacttca aaatcagtga    1560
tgggagtaag agcaaatttc atctttccaa attgatgggt gggctagtaa taaaatattt    1620
aaaaaaaaac attcaaaaac atggccacat ccaacatttc ctcaggcaat tccttttgat    1680
tcttttttct tcccctcca tgtagaagag ggagaaggag aggctctgaa agctgcttct    1740
gggggatttc aagggactgg gggtgccaac cacctctggc cctgttgtgg gggtgtcaca    1800
gaggcagtgg cagcaacaaa ggatttgaaa cttggtgtgt tcgtggagcc acaggcagac    1860
gatgtcaacc ttgtgtgagt gtgacggggg ttggggtggg gcgggaggcc acgggggagg    1920
ccgaggcagg ggctgggcag aggggagagg aagcacaaga agtgggagtg ggagaggaag    1980
ccacgtgctg gagagtagac atcccctcc ttgccgctgg gagagccaag gcctatgcca    2040
cctgcagcgt ctgagcggcc gcctgtcctt ggtggccggg ggtgggggcc tgctgtgggt    2100

```
cagtgtgcca ccctctgcag ggcagcctgt gggagaaggg acagcgggta aaaagagaag    2160
gcaagctggc aggagggtgg cacttcgtgg atgacctcct tagaaaagac tgaccttgat    2220
gtcttgagag cgctggcctc ttcctccctc cctgcagggt aggggcctg agttgagggg     2280 cttccctctg ctccacagaa accctgtttt attgagttct gaaggttgga actgctgcca    2340
tgattttggc cactttgcag acctgggact ttagggctaa ccagttctct ttgtaaggac    2400
ttgtgcctct tgggagacgt ccacccgttt ccaagcctgg ccactggca tctctggagt     2460 gtgtggggt ctggaggca ggtcccgagc ccctgtcct tcccacggcc actgcagtca       2520
cccctgtctg cgccgctgtg ctgttgtctg ccgtgagagc ccaatcactg cctatacccc    2580
tcatcacacg tcacaatgtc ccgaattccc agcctcacca ccccttctca gtaatgaccc    2640
tggttggttg caggaggtac ctactccata ctgagggtga aattaaggga aggcaaagtc    2700
caggcacaag agtgggaccc cagcctctca ctctcagttc cactcatcca actgggaccc    2760
tcaccacgaa tctcatgatc tgattcggtt ccctgtctcc tcctcccgtc acagatgtga    2820
gccagggcac tgctcagctg tgaccctagg tgtttctgcc ttgttgacat ggagagagcc    2880 cttt ccctg agaaggcctg gccccttcct gtgctgagcc cacagcagca ggctgggtgt    2940
cttggttgtc agtggtggca ccaggatgga agggcaaggc acccagggca ggcccacagt    3000
cccgctgtcc cccacttgca ccctagcttg tagctgccaa cctccagac agcccagccc     3060 gctgctcagc tccacatgca tagtatcagc cctccacacc cgacaaaggg gaacacaccc    3120
ccttggaaat ggttctttc ccccagtccc agctggaagc catgctgtct gttctgctgg     3180
agcagctgaa catatacata gatgttgccc tgccctcccc atctgcaccc tgttgagttg    3240
tagttggatt tgtctgttta tgcttggatt caccagagtg actatgatag tgaaaagaaa    3300
aaaaaaaaaa aaaaaggacg catgtatctt gaaatgcttg taaagaggtt tctaacccac    3360
cctcacgagg tgtctctcac ccccacactg ggactcgtgt ggcctgtgtg gtgccaccct    3420
gctggggcct cccaagttttt gaaaggcttt cctcagcacc tgggacccaa cagagaccag    3480
cttctagcag ctaaggaggc cgttcagctg tgacgaaggc ctgaagcaca ggattaggac    3540
tgaagcgatg atgtcccctt ccctacttcc ccttggggct ccctgtgtca gggcacagac    3600
taggtcttgt ggctggtctg gcttgcggcg cgaggatggt tctctctggt catagcccga    3660
agtctcatgg cagtcccaaa ggaggcttac aactcctgca tcacaagaaa aaggaagcca    3720
ctgccagctg gggggatctg cagctcccag aagctccgtg agcctcagcc accccctcaga   3780 ctgggttcct ctccaagctc gccctctgga ggggcagcgc agcctccac caagggccct     3840 gcgaccacag cagggattgg gatgaattgc ctgtcctgga tctgctctag aggcccaagc    3900
tgcctgcctg aggaaggatg acttgacaag tcaggagaca ctgttcccaa agccttgacc    3960
agagcacctc agcccgctga ccttgcacaa actccatctg ctgccatgag aaaagggaag    4020
ccgcctttgc aaaacattgc tgcctaaaga aactcagcag cctcaggccc aattctgcca    4080
cttctggttt gggtacagtt aaaggcaacc ctgagggact tggcagtaga aatccagggc    4140
ctcccctggg gctggcagct tcgtgtgcag ctagagcttt acctgaaagg aagtctctgg    4200
gcccagaact ctccaccaag agcctccctg ccgttcgctg agtcccagca attctcctaa    4260
gttgaaggga tctgagaagg agaaggaaat gtggggtaga tttggtggtg gttagagata    4320 tgcccctc attactgcca acagtttcgg ctgcatttct tcacgcacct cggttcctct     4380
tcctgaagtt cttgtgccct gctcttcagc accatgggcc ttcttatacg gaaggctctg    4440
```

| | | |
|---|---|---|
| ggatctcccc cttgtgggggg caggctcttg gggccagcct aagatcatgg tttagggtga | 4500 | |
| tcagtgctgg cagataaatt gaaaaggcac gctggcttgt gatcttaaat gaggacaatc | 4560 | |
| cccccagggc tgggcactcc tcccctcccc tcacttctcc cacctgcaga gccagtgtcc | 4620 | |
| ttgggtgggc tagataggat atactgtatg ccggctcctt caagctgctg actcacttta | 4680 | |
| tcaatagttc catttaaatt gacttcagtg gtgagactgt atcctgtttg ctattgcttg | 4740 | |
| ttgtgctatg ggggggagggg ggaggaatgt gtaagatagt taacatgggc aaagggagat | 4800 | |
| cttggggtgc agcacttaaa ctgcctcgta accctttca tgatttcaac cacatttgct | 4860 | |
| agagggaggg agcagccacg gagttagagg cccttggggt ttctcttttc cactgacagg | 4920 | |
| ctttcccagg cagctggcta gttcattccc tccccagcca ggtgcaggcg taggaatatg | 4980 | |
| gacatctggt tgctttggcc tgctgccctc tttcaggggt cctaagccca caatcatgcc | 5040 | |
| tccctaagac cttggcatcc ttccctctaa gccgttggca cctctgtgcc acctctcaca | 5100 | |
| ctggctccag acacacagcc tgtgcttttg gagctgagat cactcgcttc accctcctca | 5160 | |
| tctttgttct ccaagtaaag ccacgaggtc ggggcgaggg cagaggtgat cacctgcgtg | 5220 | |
| tcccatctac agacctgcgg cttcataaaa cttctgattt ctcttcagct ttgaaaaggg | 5280 | |
| ttaccctggg cactggccta gagcctcacc tcctaataga cttagcccca tgagtttgcc | 5340 | |
| atgttgagca ggactatttc tggcacttgc aagtcccatg atttcttcgg taattctgag | 5400 | |
| ggtgggggga gggacatgaa atcatcttag cttagctttc tgtctgtgaa tgtctatata | 5460 | |
| gtgtattgtg tgttttaaca aatgatttac actgactgtt gctgtaaaag tgaatttgga | 5520 | |
| aataaagtta ttactctgat taaa | 5544 | |

<210> SEQ ID NO 5
<211> LENGTH: 5724
<212> TYPE: DNA
<213> ORGANISM: Homo Sapiens

<400> SEQUENCE: 5

| | | |
|---|---|---|
| acggccgagc ggcagggcgc tcgcgcgcgc ccactagtgg ccggaggaga aggctcccgc | 60 | |
| ggaggccgcg ctgcccgccc cctccctgg ggaggctcgc gttcccgctg ctcgcgcctg | 120 | |
| cgccgcccgc cggcctcagg aacgcgccct cttcgccggc gcgcgccctc gcagtcaccg | 180 | |
| ccacccacca gctccggcac caacagcagc gccgctgcca ccgcccacct tctgccgccg | 240 | |
| ccaccacagc caccttctcc tcctccgctg tcctctcccg tcctcgcctc tgtcgactat | 300 | |
| caggtgaact ttgaaccagg atggctgagc ccgccagga gttcgaagtg atggaagatc | 360 | |
| acgctgggac gtacggggttg ggggacagga aagatcaggg gggctacacc atgcaccaag | 420 | |
| accaagaggg tgacacggac gctggcctga agaatctcc cctgcagacc cccactgagg | 480 | |
| acggatctga ggaaccgggc tctgaaacct ctgatgctaa gagcactcca acagcggaag | 540 | |
| ctgaagaagc aggcattgga gacacccca gcctggaaga cgaagctgct ggtcacgtga | 600 | |
| cccaagctcg catggtcagt aaaagcaaag acgggactgg aagcgatgac aaaaaagcca | 660 | |
| aggggggctga tggtaaaacg aagatcgcca caccgcgggg agcagcccct ccaggccaga | 720 | |
| agggccaggc caacgccacc aggattccag caaaaaccccc gccgctccaa aagacaccac | 780 | |
| ccagctctgg tgaacctcca aaatcagggg atcgcagcgg ctacagcagc cccggctccc | 840 | |
| caggcactcc cggcagccgc tcccgcaccc cgtcccttcc aacccacccc acccgggagc | 900 | |
| ccaagaaggt ggcagtggtc cgtactccac ccaagtcgcc gtcttccgcc aagagccgcc | 960 | |
| tgcagacagc ccccgtgccc atgccagacc tgaagaatgt caagtccaag atcggctcca | 1020 | |

```
ctgagaacct gaagcaccag ccgggaggcg ggaaggtgca gataattaat aagaagctgg    1080
atcttagcaa cgtccagtcc aagtgtggct caaaggataa tatcaaacac gtcccgggag    1140
gcggcagtgt gcaaatagtc tacaaaccag ttgacctgag caaggtgacc tccaagtgtg    1200
gctcattagg caacatccat cataaaccag gaggtggcca ggtggaagta aaatctgaga    1260
agcttgactt caaggacaga gtccagtcga agattgggtc cctggacaat atcacccacg    1320
tccctggcgg aggaaataaa aagattgaaa cccacaagct gaccttccgc gagaacgcca    1380
aagccaagac agaccacggg gcggagatcg tgtacaagtc gccagtggtg tctggggaca    1440
cgtctccacg gcatctcagc aatgtctcct ccaccggcag catcgacatg gtagactcgc    1500
cccagctcgc cacgctagct gacgaggtgt ctgcctccct ggccaagcag ggtttgtgat    1560
caggcccctg gggcggtcaa taattgtgga gaggagagaa tgagagagtg tggaaaaaaa    1620
aagaataatg acccggcccc cgccctctgc cccagctgc tcctcgcagt tcggttaatt    1680
ggttaatcac ttaacctgct tttgtcactc ggctttggct cgggacttca aaatcagtga    1740
tgggagtaag agcaaatttc atctttccaa attgatgggt gggctagtaa taaaatattt    1800
aaaaaaaaac attcaaaaac atggccacat ccaacatttc ctcaggcaat cctttttgat    1860 tctttttttct tccccctcca tgtagaagag ggagaaggag aggctctgaa agctgcttct    1920
gggggatttc aagggactgg gggtgccaac cacctctggc cctgttgtgg gggtgtcaca    1980
gaggcagtgg cagcaacaaa ggatttgaaa cttggtgtgt tcgtggagcc acaggcagac    2040
gatgtcaacc ttgtgtgagt gtgacggggg ttggggtggg gcgggaggcc acggggagg    2100 ccgaggcagg ggctgggcag aggggagagg aagcacaaga agtgggagtg ggagaggaag    2160
ccacgtgctg gagagtagac atcccccctcc ttgccgctgg gagagccaag gcctatgcca    2220
cctgcagcgt ctgagcggcc gcctgtcctt ggtggccggg ggtgggggcc tgctgtgggt    2280
cagtgtgcca ccctctgcag ggcagccgt gggagaaggg acagcgggta aaagagaag    2340 gcaagctggc aggagggtgg cacttcgtgg atgacctcct tagaaaagac tgaccttgat    2400
gtcttgagag cgctggcctc ttcctccctc cctgcagggt aggggcctg agttgagggg    2460 cttccctctg ctccacagaa accctgtttt attgagttct gaaggttgga actgctgcca    2520
tgattttggc cactttgcag acctgggact ttagggctaa ccagttctct ttgtaaggac    2580
ttgtgcctct tgggagacgt ccacccgttt ccaagcctgg ccactggca tctctggagt    2640 gtgtggggt ctgggaggca ggtcccgagc ccctgtcct tcccacggcc actgcagtca    2700
cccctgtctg cgccgctgtg ctgttgtctg ccgtgagagc caatcactg cctataccc    2760 tcatcacacg tcacaatgtc ccgaattccc agcctcacca cccttctca gtaatgaccc    2820 tggttggttg caggaggtac ctactccata ctgagggtga aattaaggga aggcaaagtc    2880
caggcacaag agtgggaccc cagcctctca ctctcagttc cactcatcca actgggaccc    2940
tcaccacgaa tctcatgatc tgattcggtt ccctgtctcc cctcccgtc acagatgtga    3000 gccagggcac tgctcagctg tgaccctagg tgtttctgcc ttgttgacat ggagagagcc    3060
ctttcccctg agaaggcctg gccccttcct gtgctgagcc acagcagca ggctgggtgt    3120 cttggttgtc agtggtggca ccaggatgga agggcaaggc acccagggca ggcccacagt    3180
cccgctgtcc cccacttgca ccctagcttg tagctgccaa cctcccagac agcccagccc    3240
gctgctcagc tccacatgca tagtatcagc cctccacacc cgacaaaggg gaacacaccc    3300
ccttggaaat ggttcttttc ccccagtccc agctggaagc catgctgtct gttctgctgg    3360
```

```
agcagctgaa catatacata gatgttgccc tgccctcccc atctgcaccc tgttgagttg   3420
tagttggatt tgtctgttta tgcttggatt caccagagtg actatgatag tgaaaagaaa   3480
aaaaaaaaaa aaaaaggacg catgtatctt gaaatgcttg taaagaggtt tctaacccac   3540
cctcacgagg tgtctctcac ccccacactg ggactcgtgt ggcctgtgtg gtgccaccct   3600
gctggggcct cccaagtttt gaaaggcttt cctcagcacc tgggacccaa cagagaccag   3660
cttctagcag ctaaggaggc cgttcagctg tgacgaaggc ctgaagcaca ggattaggac   3720
tgaagcgatg atgtccccct ccctacttcc ccttggggct ccctgtgtca gggcacagac   3780
taggtcttgt ggctggtctg gcttgcggcg cgaggatggt tctctctggt catagcccga   3840
agtctcatgg cagtcccaaa ggaggcttac aactcctgca tcacaagaaa aaggaagcca   3900
ctgccagctg gggggatctg cagctcccag aagctccgtg agcctcagcc acccctcaga   3960
ctgggttcct ctccaagctc gccctctgga ggggcagcgc agcctccac caagggccct   4020 gcgaccacag cagggattgg gatgaattgc ctgtcctgga tctgctctag aggcccaagc   4080
tgcctgcctg aggaaggatg acttgacaag tcaggagaca ctgttcccaa gccttgacc   4140 agagcacctc agcccgctga ccttgcacaa actccatctg ctgccatgag aaaagggaag   4200
ccgcctttgc aaaacattgc tgcctaaaga aactcagcag cctcaggccc aattctgcca   4260
cttctggttt gggtacagtt aaaggcaacc ctgagggact tggcagtaga aatccagggc   4320
ctcccctggg gctggcagct tcgtgtgcag ctagagcttt acctgaaagg aagtctctgg   4380
gcccagaact ctccaccaag agcctccctg ccgttcgctg agtcccagca attctcctaa   4440
gttgaaggga tctgagaagg agaaggaaat gtggggtaga tttggtggtg gttagagata   4500
tgcccccctc attactgcca acagtttcgg ctgcatttct tcacgcacct cggttcctct   4560
tcctgaagtt cttgtgccct gctcttcagc accatgggcc ttcttatacg gaaggctctg   4620
ggatctcccc cttgtggggg caggctcttg ggccagcct aagatcatgg tttagggtga   4680
tcagtgctgg cagataaatt gaaaaggcac gctggcttgt gatcttaaat gaggacaatc   4740
cccccagggc tgggcactcc tccctccc tcacttctcc cacctgcaga gccagtgtcc   4800
ttgggtgggg tagataggat atactgtatg ccggctcctt caagctgctg actcacttta   4860
tcaatagttc catttaaatt gacttcagtg gtgagactgt atcctgtttg ctattgcttg   4920
ttgtgctatg gggggagggg ggaggaatgt gtaagatagt taacatgggc aaagggagat   4980
cttggggtgc agcacttaaa ctgcctcgta acccttttca tgatttcaac cacatttgct   5040
agagggaggg agcagccacg gagttagagg cccttgtgggt ttctcttttc cactgacagg   5100 cttttcccagg cagctggcta gttcattccc tccccagcca ggtgcaggcg taggaatatg   5160
gacatctggt tgctttggcc tgctgccctc tttcaggggt cctaagccca caatcatgcc   5220
tccctaagac cttggcatcc ttccctctaa gccgttggca cctctgtgcc acctctcaca   5280
ctggctccag acacacagcc tgtgcttttg gagctgagat cactcgcttc accctcctca   5340
tctttgttct ccaagtaaag ccacgaggtc ggggcgaggg cagaggtgat cacctgcgtg   5400
tcccatctac agacctgcgg cttcataaaa cttctgattt ctcttcagct ttgaaaaggg   5460
ttaccctggg cactggccta gagcctcacc tcctaataga cttagcccca tgagtttgcc   5520
atgttgagca ggactatttc tggcacttgc aagtcccatg atttcttcgg taattctgag   5580
ggtgggggga gggacatgaa atcatcttag cttagctttc tgtctgtgaa tgtctatata   5640
gtgtattgtg tgttttaaca aatgatttac actgactgtt gctgtaaaag tgaatttgga   5700
aataaagtta ttactctgat taaa                                         5724
```

<210> SEQ ID NO 6
<211> LENGTH: 6816
<212> TYPE: DNA
<213> ORGANISM: Homo Sapiens

<400> SEQUENCE: 6

| | | | | | | |
|---|---|---|---|---|---|---|
| acggccgagc | ggcagggcgc | tcgcgcgcgc | ccactagtgg | ccggaggaga | aggctcccgc | 60 |
| ggaggccgcg | ctgcccgccc | cctcccctgg | ggaggctcgc | gttcccgctg | ctcgcgcctg | 120 |
| cgccgcccgc | cggcctcagg | aacgcgccct | cttcgccggc | gcgcgccctc | gcagtcaccg | 180 |
| ccacccacca | gctccggcac | caacagcagc | gccgctgcca | ccgcccacct | tctgccgccg | 240 |
| ccaccacagc | caccttctcc | tcctccgctg | tcctctcccg | tcctcgcctc | tgtcgactat | 300 |
| caggtgaact | ttgaaccagg | atggctgagc | ccgccaggga | gttcgaagtg | atggaagatc | 360 |
| acgctgggac | gtacggggttg | ggggacagga | aagatcaggg | gggctacacc | atgcaccaag | 420 |
| accaagaggg | tgacacggac | gctggcctga | agaatctccc | cctgcagacc | cccactgagg | 480 |
| acggatctga | ggaaccgggc | tctgaaacct | ctgatgctaa | gagcactcca | acagcggaag | 540 |
| atgtgacagc | cccttagtg | gatgaggag | ctcccggcaa | gcaggctgcc | gcgcagcccc | 600 |
| acacggagat | cccagaagga | accacagctg | aagaagcagg | cattggagac | accccagcc | 660 |
| tggaagacga | agctgctggt | cacgtgaccc | aagagcctga | agtggtaag | gtggtccagg | 720 |
| aaggcttcct | ccgagagcca | ggccccccag | gtctgagcca | ccagctcatg | tccggcatgc | 780 |
| ctggggctcc | cctcctgcct | gagggcccca | gagaggccac | acgccaacct | tcggggacag | 840 |
| gacctgagga | cacagagggc | ggccgccacg | cccctgagct | gctcaagcac | cagcttctag | 900 |
| gagacctgca | ccaggagggg | ccgccgctga | aggggcagg | gggcaaagag | aggccggga | 960 |
| gcaaggagga | ggtggatgaa | gaccgcgacg | tcgatgagtc | ctccccccaa | gactcccctc | 1020 |
| cctccaaggc | ctccccagcc | caagatgggc | ggcctcccca | gacagccgcc | agagaagcca | 1080 |
| ccagcatccc | aggcttccca | gcggagggtg | ccatcccccct | ccctgtggat | ttcctctcca | 1140 |
| aagtttccac | agagatccca | gcctcagagc | ccgacgggcc | cagtgtaggg | cgggccaaag | 1200 |
| ggcaggatgc | ccccctggag | ttcacgtttc | acgtggaaat | cacacccaac | gtgcagaagg | 1260 |
| agcaggcgca | ctcggaggag | catttgggaa | gggctgcatt | tccagggcc | cctggagagg | 1320 |
| ggccagaggc | ccggggcccc | tctttgggag | aggacacaaa | agaggctgac | cttccagagc | 1380 |
| cctctgaaaa | gcagcctgct | gctgctccgc | ggggaagcc | cgtcagccgg | gtccctcaac | 1440 |
| tcaaagctcg | catggtcagt | aaaagcaaag | acgggactgg | aagcgatgac | aaaaaagcca | 1500 |
| agacatccac | acgttcctct | gctaaaacct | tgaaaaatag | gccttgcctt | agccccaaac | 1560 |
| accccactcc | tggtagctca | gaccctctga | tccaaccctc | cagccctgct | gtgtgcccag | 1620 |
| agccaccttc | ctctcctaaa | acgtctcttt | ctgtcacttc | ccgaactggc | agttctggag | 1680 |
| caaaggagat | gaaactcaag | ggggctgatg | gtaaaacgaa | gatcgccaca | ccgcggggag | 1740 |
| cagcccctcc | aggccagaag | ggccaggcca | acgccaccag | gattccagca | aaaacccgc | 1800 |
| ccgctccaaa | gacaccaccc | agctctgcga | ctaagcaagt | ccagagaaga | ccacccctg | 1860 |
| cagggccag | atctgagaga | ggtgaacctc | caaaatcagg | ggatcgcagc | ggctacagca | 1920 |
| gccccggctc | cccaggcact | cccggcagcc | gctcccgcac | ccgtcccctt | ccaaccccac | 1980 |
| ccaccccggga | gccaagaag | gtggcagtgg | tccgtactcc | acccaagtcg | ccgtcttccg | 2040 |
| ccaagagccg | cctgcagaca | gccccgtgc | ccatgccaga | cctgaagaat | gtcaagtcca | 2100 |

```
agatcggctc cactgagaac ctgaagcacc agccgggagg cgggaaggtg cagataatta    2160
ataagaagct ggatcttagc aacgtccagt ccaagtgtgg ctcaaaggat aatatcaaac    2220
acgtcccggg aggcggcagt gtgcaaatag tctacaaacc agttgacctg agcaaggtga    2280
cctccaagtg tggctcatta ggcaacatcc atcataaacc aggaggtggc caggtggaag    2340
taaaatctga gaagcttgac ttcaaggaca gagtccagtc gaagattggg tccctggaca    2400
atatcaccca cgtccctggc ggaggaaata aaaagattga aacccacaag ctgaccttcc    2460
gcgagaacgc caaagccaag acagaccacg gggcggagat cgtgtacaag tcgccagtgg    2520
tgtctgggga cacgtctcca cggcatctca gcaatgtctc ctccaccggc agcatcgaca    2580
tggtagactc gccccagctc gccacgctag ctgacgaggt gtctgcctcc ctggccaagc    2640
agggtttgtg atcaggcccc tggggcggtc ataattgtg gagaggagag aatgagagag    2700
tgtggaaaaa aaagaataa tgacccggcc cccgccctct gccccagct gctcctcgca    2760 gttcggttaa ttggttaatc acttaacctg cttttgtcac tcggctttgg ctcgggactt    2820
caaaatcagt gatgggagta agagcaaatt tcatctttcc aaattgatgg gtgggctagt    2880
aataaaatat ttaaaaaaaa acattcaaaa acatggccac atccaacatt tcctcaggca    2940 attcctttg attctttttt cttccccctc catgtagaag agggagaagg agaggctctg    3000
aaagctgctt ctgggggatt tcaagggact gggggtgcca accacctctg gccctgttgt    3060
gggggtgtca cagaggcagt ggcagcaaca aaggatttga aacttggtgt gttcgtggag    3120
ccacaggcag acgatgtcaa ccttgtgtga gtgtgacggg ggttggggtg gggcgggagg    3180
ccacggggga ggccgaggca ggggctgggc agaggggaga ggaagcacaa gaagtgggag    3240
tgggagagga agccacgtgc tggagagtag acatccccct ccttgccgct gggagagcca    3300
aggcctatgc cacctgcagc gtctgagcgg ccgcctgtcc ttggtggccg ggggtggggg    3360
cctgctgtgg gtcagtgtgc caccctctgc agggcagcct gtgggagaag ggacagcggg    3420
taaaaagaga aggcaagctg gcaggagggt ggcacttcgt ggatgacctc cttagaaaag    3480
actgaccttg atgtcttgag agcgctggcc tcttcctccc tccctgcagg gtaggggcc    3540 tgagttgagg ggcttccctc tgctccacag aaaccctgtt ttattgagtt ctgaaggttg    3600
gaactgctgc catgattttg gccactttgc agacctggga ctttagggct aaccagttct    3660
ctttgtaagg acttgtgcct cttgggagac gtccacccgt ttccaagcct gggccactgg    3720
catctctgga gtgtgtgggg gtctgggagg caggtcccga gcccctgtc cttcccacgg    3780 ccactgcagt caccccctgtc tgcgccgctg tgctgttgtc tgccgtgaga gcccaatcac    3840
tgcctatacc cctcatcaca cgtcacaatg tcccgaattc ccagcctcac caccccttct    3900
cagtaatgac cctggttggt tgcaggaggt acctactcca tactgagggt gaaattaagg    3960
gaaggcaaag tccaggcaca agagtgggac cccagcctct cactctcagt tccactcatc    4020
caactgggac cctcaccacg aatctcatga tctgattcgg ttccctgtct cctcctcccg    4080
tcacagatgt gagccagggc actgctcagc tgtgacccta ggtgtttctg ccttgttgac    4140
atggagagag ccctttcccc tgagaaggcc tggcccttc ctgtgctgag cccacagcag    4200
caggctgggt gtcttggttg tcagtggtgg caccaggatg gaaggcaag gcacccaggg    4260 caggcccaca gtcccgctgt cccccacttg caccctagct tgtagctgcc aacctcccag    4320
acagcccagc ccgctgctca gctccacatg catagtatca gccctccaca cccgacaaag    4380
gggaacacac ccccttggaa atggttcttt tcccccagtc ccagctggaa gccatgctgt    4440
ctgttctgct ggagcagctg aacatataca tagatgttgc cctgccctcc ccatctgcac    4500
```

```
cctgttgagt tgtagttgga tttgtctgtt tatgcttgga ttcaccagag tgactatgat    4560
agtgaaaaga aaaaaaaaaa aaaaaaagga cgcatgtatc ttgaaatgct tgtaaagagg    4620
tttctaaccc accctcacga ggtgtctctc accccacac  tgggactcgt gtggcctgtg    4680
tggtgccacc ctgctggggc ctcccaagtt ttgaaaggct ttcctcagca cctgggaccc    4740
aacagagacc agcttctagc agctaaggag gccgttcagc tgtgacgaag gcctgaagca    4800
caggattagg actgaagcga tgatgtcccc ttccctactt cccttgggg  ctccctgtgt    4860 cagggcacag actaggtctt gtggctggtc tggcttgcgg cgcgaggatg gttctctctg    4920
gtcatagccc gaagtctcat ggcagtccca aggaggctt  acaactcctg catcacaaga    4980
aaaaggaagc cactgccagc tgggggggatc tgcagctccc agaagctccg tgagcctcag    5040 ccaccccctca gactgggttc ctctccaagc tcgccctctg gaggggcagc gcagcctccc    5100
accaagggcc ctgcgaccac agcagggatt gggatgaatt gcctgtcctg gatctgctct    5160
agaggcccaa gctgcctgcc tgaggaagga tgacttgaca agtcaggaga cactgttccc    5220
aaagccttga ccagagcacc tcagcccgct gaccttgcac aaactccatc tgctgccatg    5280
agaaaaggga agccgccttt gcaaaacatt gctgcctaaa gaaactcagc agcctcaggc    5340
ccaattctgc cacttctggt ttgggtacag ttaaaggcaa cctgaggga  cttggcagta    5400 gaaatccagg gcctcccctg gggctggcag cttcgtgtgc agctagagct ttacctgaaa    5460
ggaagtctct gggcccagaa ctctccacca agagcctccc tgccgttcgc tgagtcccag    5520
caattctcct aagttgaagg gatctgagaa ggagaaggaa atgtggggta gatttggtgg    5580
tggttagaga tatgcccccc tcattactgc caacagtttc ggctgcattt cttcacgcac    5640
ctcggttcct cttcctgaag ttcttgtgcc ctgctcttca gcaccatggg ccttcttata    5700
cggaaggctc tgggatctcc cccttgtggg ggcaggctct tggggccagc ctaagatcat    5760
ggtttagggt gatcagtgct ggcagataaa ttgaaaaggc acgctggctt gtgatcttaa    5820
atgaggacaa tcccccaggg gctgggcact cctcccctcc cctcacttct cccacctgca    5880
gagccagtgt ccttgggtgg gctagatagg atatactgta tgccggctcc ttcaagctgc    5940
tgactcactt tatcaatagt tccatttaaa ttgacttcag tggtgagact gtatcctgtt    6000
tgctattgct tgttgtgcta tggggggagg gggaggaat  tgtaagata  gttaacatgg    6060 gcaaagggag atcttggggt gcagcactta aactgcctcg taaccctttt catgatttca    6120
accacatttg ctagagggag ggagcagcca cggagttaga ggcccttggg gtttctcttt    6180
tccactgaca ggctttccca ggcagctggc tagttcattc cctccccagc caggtgcagg    6240
cgtaggaata tggacatctg gttgctttgg cctgctgccc tctttcaggg gtcctaagcc    6300
cacaatcatg cctccctaag accttggcat ccttccctct aagccgttgg cacctctgtg    6360
ccacctctca cactggctcc agacacacag cctgtgcttt tggagctgag atcactcgct    6420
tcaccctcct catctttgtt ctccaagtaa agccacgagg tcgggcgag  ggcagaggtg    6480 atcacctgcg tgtcccatct acagacctgc ggcttcataa aacttctgat ttctcttcag    6540
ctttgaaaag ggttaccctg ggcactggcc tagagcctca cctcctaata gacttagccc    6600
catgagtttg ccatgttgag caggactatt tctggcactt gcaagtccca tgatttcttc    6660
ggtaattctg agggtggggg gagggacatg aaatcatctt agcttagctt tctgtctgtg    6720
aatgtctata tagtgtattg tgtgttttaa caaatgattt acactgactg ttgctgtaaa    6780
agtgaatttg gaaataaagt tattactctg attaaa                              6816
```

<210> SEQ ID NO 7
<211> LENGTH: 212
<212> TYPE: DNA
<213> ORGANISM: Homo Sapiens

<400> SEQUENCE: 7

```
catgagtttg ccatgttgag caggactatt tctggcactt gcaagtccca tgatttcttc      60
ggtaattctg agggtggggg gagggacatg aaatcatctt agcttagctt tctgtctgtg     120
aatgtctata tagtgtattg tgtgttttaa caaatgattt acactgactg ttgctgtaaa     180
agtgaatttg gaaataaagt tattactctg at                                    212
```

<210> SEQ ID NO 8
<211> LENGTH: 240
<212> TYPE: DNA
<213> ORGANISM: Homo Sapiens

<400> SEQUENCE: 8

```
acggccgagc ggcagggcgc tcgcgcgcgc ccactagtgg ccggaggaga aggctcccgc      60
ggaggccgcg ctgcccgccc cctcccctgg ggaggctcgc gttccgcctg ctcgcgcctg     120
cgccgcccgc cggcctcagg aacgcgccct cttcgccggc gcgcgccctc gcagtcaccg     180
ccacccacca gctccggcac caacagcagc gccgctgcca ccgcccacct tctgccgccg     240
```

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

```
Tyr Gly Arg Lys Lys Arg Arg Gln Arg Arg Arg
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 10

```
Arg Arg Gln Arg Arg Thr Ser Lys Leu Met Lys Arg
1               5                   10
```

<210> SEQ ID NO 11
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 11

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 12
<211> LENGTH: 33
<212> TYPE: PRT
<213> ORGANISM: Artificial Sequence

```
<220> FEATURE:
<223> OTHER INFORMATION: Synthetic polypeptide

<400> SEQUENCE: 12

Lys Ala Leu Ala Trp Glu Ala Lys Leu Ala Lys Ala Leu Ala Lys Ala
1               5                   10                  15
Leu Ala Lys His Leu Ala Lys Ala Leu Ala Lys Ala Leu Lys Cys Glu
            20                  25                  30
Ala

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 14

Arg Lys Lys Arg Arg Gln Arg Arg Arg
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 15

Tyr Ala Arg Ala Ala Ala Arg Gln Ala Arg Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 16

Thr His Arg Leu Pro Arg Arg Arg Arg Arg
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 17

Gly Gly Arg Arg Ala Arg Arg Arg Arg Arg
1               5                   10
```

METHODS FOR TREATING APOLIPOPROTEIN E4-ASSOCIATED DISORDERS

CROSS-REFERENCE

This application is a Continuation of U.S. patent application Ser. No. 14/668,909, filed Mar. 25, 2015, now U.S. Pat. No. 9,885,039, which application is a Continuation of U.S. patent application Ser. No. 12/958,057, filed Dec. 1, 2010, which application claims the benefit of U.S. Provisional Patent Application No. 61/266,449, filed Dec. 3, 2009, and U.S. Provisional Patent Application No. 61/356,977, filed Jun. 21, 2010, which applications are incorporated herein by reference in their entirety.

STATEMENT REGARDING FEDERALLY SPONSORED RESEARCH

This invention was made with government support under Grant No. P01 AG022074 awarded by the National Institutes of Health. The government has certain rights in the invention.

BACKGROUND

Apolipoprotein (apo) E, a polymorphic protein with three isoforms (apoE2, apoE3, and apoE4), is essential for lipid homeostasis. Carriers of apoE4 are at higher risk for developing Alzheimer's disease (AD). The hippocampus is one of the first regions of the brain damaged in AD, and memory deficits and disorientation are among the early symptoms.

Tau protein is expressed in central nervous system and plays a critical role in the neuronal architecture by stabilizing intracellular microtubule network. Impairment of the physiological role of the tau protein either by truncation, hyperphosphorylation or by disturbing the balance between the six naturally occurring tau isoforms leads to the formation of neurofibrillary tangles (NFT), dystrophic neurites and neuropil threads. These structures represent ultrastructural hallmarks of Alzheimer's disease (AD). The major protein subunit of these structures is microtubule associated protein Tau. The amount of NFT found in autopsies of AD patients correlates with clinical symptoms including intellectual decline. Therefore, Tau protein plays a critical role in AD pathology.

LITERATURE

Roberson et al. (2007) *Science* 316:750; Brunden et al. (Oct. 1, 2009) *Nature Reviews Drug Discovery* 8:783.

SUMMARY

The present disclosure provides a method of increasing the functionality of a GABAergic interneuron in the hilus of the hippocampus of an individual having at least one apolipoprotein E4 (apoE4) allele. The method generally involves reducing tau levels in the interneuron.

BRIEF DESCRIPTION OF THE DRAWINGS

FIGS. 11A and 11B depict exemplary tau target sequences (SEQ ID NOs:7 and 8).

DEFINITIONS

Figure 1:
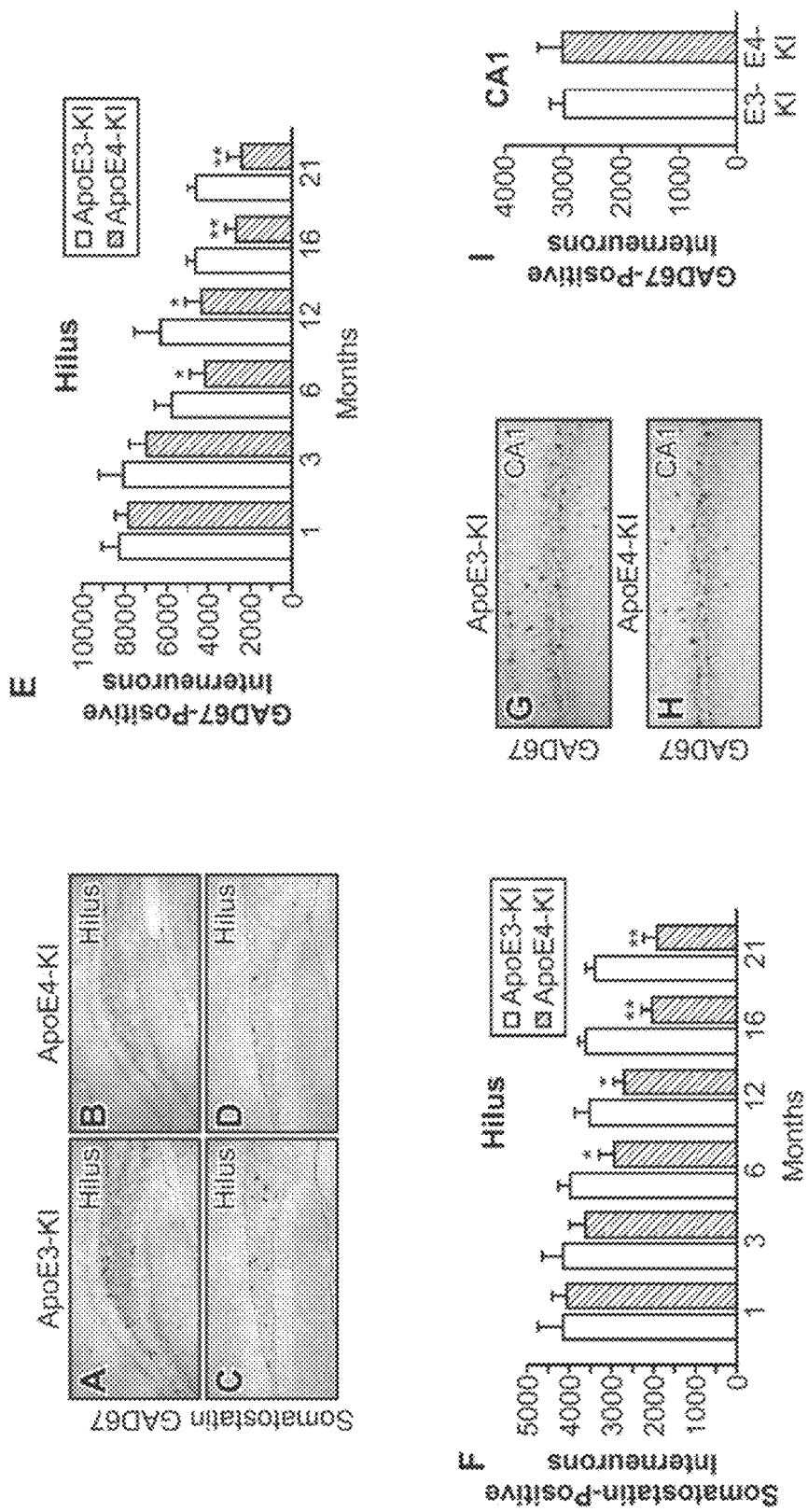
FIG. 1, panels A-I, depict age-dependent decrease in numbers of GABAergic interneurons in the hilus of dentate gyrus of female ApoE4-KI mice.

As used herein, an "apoE4-associated disorder" is any disorder that is caused by the presence of apoE4 in a cell, in the serum, in the interstitial fluid, in the cerebrospinal fluid, or in any other bodily fluid of an individual; any physiological process or metabolic event that is influenced by apoE4 domain interaction; any disorder that is characterized by the presence of apoE4; a symptom of a disorder that is caused by the presence of apoE4 in a cell or in a bodily fluid; a phenomenon associated with a disorder caused by the presence in a cell or in a bodily fluid of apoE4; and the sequelae of any disorder that is caused by the presence of apoE4. ApoE4-associated disorders include apoE4-associated neurological disorders and disorders related to high serum lipid levels. ApoE4-associated neurological disorders include, but are not limited to, sporadic Alzheimer's disease; familial Alzheimer's disease; poor outcome following a stroke; poor outcome following traumatic head injury; and cerebral ischemia. Phenomena associated with apoE4-associated neurological disorders include, but are not limited to, neurofibrillary tangles; amyloid deposits; memory loss; and a reduction in cognitive function. ApoE4-related disorders associated with high serum lipid levels include, but are not limited to, atherosclerosis, and coronary artery disease. Phenomena associated with such apoE4-associated disorders include high serum cholesterol levels.

The term "Alzheimer's disease" (abbreviated herein as "AD") as used herein refers to a condition associated with formation of neuritic plaques comprising amyloid protein primarily in the hippocampus and cerebral cortex, as well as impairment in both learning and memory. "AD" as used herein is meant to encompass both AD as well as AD-type pathologies.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

As used herein, the term "neural stem cell" (NSC) refers to an undifferentiated neural cell that can proliferate, self-renew, and differentiate into the main adult neural cells of the brain. NSCs are capable of self-maintenance (self-renewal), meaning that with each cell division, one daughter cell will also be a stem cell. The non-stem cell progeny of NSCs are termed neural progenitor cells. Neural progenitors cells generated from a single multipotent NSC are capable of differentiating into neurons, astrocytes (type I and type II), and oligodendrocytes. Hence, NSCs are "multipotent" because their progeny have multiple neural cell fates. Thus, NSCs can be functionally defined as a cell with the ability to: 1) proliferate, 2) self-renew, and 3) produce functional progeny that can differentiate into the three main cell types found in the central nervous system: neurons, astrocytes and oligodendrocytes.

As used herein, the terms "neural progenitor cell" or "neural precursor cell" refer to a cell that can generate progeny such as neuronal cells (e.g., neuronal precursors or mature neurons), glial precursors, mature astrocytes, or mature oligodendrocytes. Typically, the cells express some of the phenotypic markers that are characteristic of the neural lineage. A "neuronal progenitor cell" or "neuronal precursor cell" is a cell that can generate progeny that are mature neurons. These cells may or may not also have the capability to generate glial cells.

A "neurosphere" is a group of cells derived from a single neural stem cell as the result of clonal expansion. A method for culturing neural stem cells to form neurospheres has been described in, for example, U.S. Pat. No. 5,750,376.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Nucleic acid sequence identity (as well as amino acid sequence identity) is calculated based on a reference sequence, which may be a subset of a larger sequence, such as a conserved motif, coding region, flanking region, etc. A reference sequence will usually be at least about 18 residues long, more usually at least about 30 residues long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17).

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-59 is used.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a compound, the amount of a recombinant expression vector, or a number of cells that, when administered to a mammal or other subject for treating a disease, is sufficient to effect such treatment for the disease. The "therapeutically effective amount" will vary depending on the compound, the expression vector, or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a tau polypeptide" includes a plurality of such tau polypeptides and reference to "the GABAergic interneuron" includes reference to one or more GABAergic interneurons and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of increasing the functionality of a GABAergic interneuron (an interneuron that produces γ-aminobutyric acid (GABA)) in the hilus of the hippocampus of an individual having at least one apolipoprotein E4 (apoE4) allele. The method generally involves reducing tau levels in the interneuron. The present disclosure provides a method of increasing cognitive function in an individual having at least one apoE4 allele.

In some embodiments, a subject method involves administering to an individual in need thereof an effective amount of an interfering nucleic acid that specifically reduces the level of tau polypeptide in a GABAergic interneuron. In other embodiments, a subject method involves administering to an individual in need thereof an effective number of stem cells that have been genetically modified to reduce the level of tau polypeptide produced by the stem cell, or by a neuron (e.g., a GABAergic neuron) generated from the stem cell.

In some embodiments, a subject method is effective to increase the number of GAD67-positive interneurons in the hippocampus (e.g., in the hilus of the dentate gyrus of the hippocampus) of an individual by at least about 5%, at least about 10%, at least about 15%, at least about 20%, at least about 25%, at least about 30%, at least about 40%, at least about 50%, or more than 50%, compared with the number of GAD67-positive interneurons in the absence of treatment, or before treatment, with the method. In some embodiments, a GAD67-positive interneuron is also somatostatin-positive. In other embodiments, a GAD67-positive interneuron is also neuropeptide Y-positive.

Thus, for example, an effective amount of an interfering nucleic acid that reduces the level of tau polypeptide in a GABAergic interneuron is an amount that is effective, when administered in one or more doses, in monotherapy or in combination therapy, to increase the number of GAD67-positive interneurons in the hippocampus of an individual by at least about 5%, at least about 10%, at least about 15%, at least about 20%, at least about 25%, at least about 30%, at least about 40%, at least about 50%, or more than 50%, compared with the number of GAD67-positive interneurons in the absence of treatment, or before treatment, with the interfering nucleic acid.

As another example, an effective number of genetically modified stem cells (e.g., stem cells that have been genetically modified to reduce the level of tau polypeptide produced by the stem cell, or by a neuron (e.g., a GABAergic neuron) generated from the stem cell of genetically modified stem cell) is a number that is effective, when administered in one or more doses, in monotherapy or in combination therapy, to increase the number of GAD67-positive interneurons in the hippocampus of an individual by at least about 5%, at least about 10%, at least about 15%, at least about 20%, at least about 25%, at least about 30%, at least about 40%, at least about 50%, or more than 50%, compared with the number of GAD67-positive interneurons in the absence of treatment, or before treatment, with the genetically modified stem cells.

GAD67 (glutamic acid decarboxylase, 67 kDa isoform) has been described in the literature; see, e.g., Lariviere et al. (2002) *Mol. Biol. Evol.* 19:2325; GenBank Accession No. AAB26937; and Yamashita et al. (1993) *Biochem. Biophys. Res. Comm.* 192:1347.

In some embodiments, a subject method is effective to increase the functionality of a GABAergic interneuron in the hippocampus of an individual by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the functionality of the GABAergic interneuron in the hippocampus of the individual in the absence of treatment, or before treatment, with the subject method. The functionality of a GABAergic interneuron includes basal GABA release, KCl-evoked GABA release, and neuregulin-evoked GABA release.

For example, in some embodiments, an effective amount of an interfering nucleic acid that reduces the level of tau polypeptide in a GABAergic interneuron is an amount that is effective, when administered in one or more doses, in monotherapy or in combination therapy (e.g., in combination with stem cell therapy or in combination therapy with at least one additional therapeutic agent), to increase the functionality of a GABAergic interneuron in the hippocampus of an individual by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the functionality of the GABAergic interneuron in the hippocampus of the individual in the absence of treatment, or before treatment, with the interfering nucleic acid.

As another example, an effective number of genetically modified stem cells (e.g., stem cells that have been genetically modified to reduce the level of tau polypeptide produced by the stem cell, or by a neuron (e.g., a GABAergic neuron) generated from the stem cell of genetically modified stem cell) is a number that is effective, when administered in one or more doses, in monotherapy or in combination therapy, to increase the functionality of a GABAergic interneuron in the hippocampus of an individual by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the functionality of the GABAergic interneuron in the hippocampus of the individual in the absence of treatment, or before treatment, with the genetically modified stem cells.

In some embodiments, a subject method is effective to ameliorate at least one phenomenon associated with an apoE4-associated neurological disorder, where such phenomena include, e.g., neurofibrillary tangles; amyloid deposits; memory loss; and a reduction in cognitive function. Thus, for example, in some embodiments, a subject method is effective to reduce memory loss and at least slow the reduction in cognitive function. For example, in some embodiments, a subject method is effective to increase memory function and/or to increase cognitive function. Thus, for example, an effective amount of an interfering nucleic acid that reduces the level of tau polypeptide in a GABAergic interneuron is an amount that is effective, when administered in one or more doses, in monotherapy or in combination therapy, to reduce memory loss, to increase memory functions, to reduce loss of cognitive function, or to increase cognitive function. As another example, an effective number of genetically modified stem cells (e.g., stem cells that have been genetically modified to reduce the level of tau polypeptide produced by the stem cell, or by a neuron (e.g., a GABAergic neuron) generated from the stem cell of genetically modified stem cell) is a number that is effective, when administered in one or more doses, in monotherapy or in combination therapy, to reduce memory loss, to increase memory functions, to reduce loss of cognitive function, or to increase cognitive function.

Interfering Nucleic Acid

As noted above, in some embodiments, an interfering nucleic acid is used to interfere with production of tau transcripts and production of tau polypeptide. Interfering nucleic acids include small nucleic acid molecules, such as a short interfering nucleic acid (siNA), a short interfering RNA (siRNA), a double-stranded RNA (dsRNA), a microRNA (miRNA), and a short hairpin RNA (shRNA).

The terms "short interfering nucleic acid," "siNA," "short interfering RNA," "siRNA," "short interfering nucleic acid molecule," "short interfering oligonucleotide molecule," and "chemically-modified short interfering nucleic acid molecule" as used herein refer to any nucleic acid molecule capable of inhibiting or down regulating gene expression, for example by mediating RNA interference "RNAi" or gene silencing in a sequence-specific manner. Design of RNAi molecules, given a target gene, is routine in the art. See also US 2005/0282188 (which is incorporated herein by reference) as well as references cited therein. See, e.g., Pushparaj et al. Clin Exp Pharmacol Physiol. 2006 May-June; 33(5-6):504-10; Lutzelberger et al. Handb Exp Pharmacol. 2006; (173):243-59; Aronin et al. Gene Ther. 2006 March; 13(6): 509-16; Xie et al. Drug Discov Today. 2006 January; 11(1-2):67-73; Grunweller et al. Curr Med Chem. 2005; 12(26): 3143-61; and Pekaraik et al. Brain Res Bull. 2005 Dec. 15; 68(1-2):115-20. Epub 2005 Sep. 9.

Methods for design and production of siRNAs to a desired target are known in the art, and their application to tau genes for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., US 2005/0282188; US 2005/0239731; US 2005/0234232; US 2005/0176018; US 2005/0059817; US 2005/0020525; US 2004/0192626; US 2003/0073640; US 2002/0150936; US 2002/0142980; and US2002/0120129, each of which are incorporated herein by reference.

Publicly available tools to facilitate design of siRNAs are available in the art. See, e.g., DEQOR: Design and Quality Control of RNAi (available on the internet at cluster-1.mpi-cbg.de/Deqor/deqor.html). See also, Henschel et al. Nucleic Acids Res. 2004 Jul. 1; 32 (Web Server issue):W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Suitable tau gene targets include, e.g., a contiguous stretch of from about 10 nucleotides (nt) to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, of nucleotides 6547-6758 of SEQ ID NO:1 (tau isoform 1 mRNA; GenBank NM_016835), nucleotides 5596-5807 of SEQ ID NO:2 (tau isoform 2 mRNA; GenBank NM_005910); nucleotides 5596-5807 of SEQ ID NO:3 (tau isoform 3 mRNA; GenBank NM_016834), nucleotides 5329-5540 of SEQ ID NO:4 (tau isoform 4 mRNA; GenBank NM_016841), nucleotides 5509-5720 of SEQ ID NO:5 (tau isoform 5 mRNA; GenBank NM_001123067), or nucleotides 6601-6812 of SEQ ID NO:6 (tau isoform 6 mRNA; GenBank NM_001123066). SEQ ID NOs:1-6 provide nucleotide sequences of tau isoform 1-6 mRNA.

Suitable tau gene targets include, e.g., a contiguous stretch of from about 10 nucleotides (nt) to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, of nucleotides 1-240 of tau isoform 1 mRNA (GenBank NM_016835). Nucleotides 1-240 of tau isoform 1 mRNA (GenBank NM_016835) are shown in FIG. 11B (SEQ ID NO:8).

Suitable tau gene targets include, e.g., nucleotides 6547-6758 of SEQ ID NO:1 (tau isoform 1 mRNA; GenBank NM_016835), nucleotides 5596-5807 of SEQ ID NO:2 (tau isoform 2 mRNA; GenBank NM_005910); nucleotides 5596-5807 of SEQ ID NO:3 (tau isoform 3 mRNA; GenBank NM_016834), nucleotides 5329-5540 of SEQ ID NO:4 (tau isoform 4 mRNA; GenBank NM_016841), nucleotides 5509-5720 of SEQ ID NO:5 (tau isoform 5 mRNA; GenBank NM_001123067), and nucleotides 6601-6812 of SEQ ID NO:6 (tau isoform 6 mRNA; GenBank NM_001123066). Suitable tau gene targets include, e.g., SEQ ID NO:7 (nucleotides 6547-6758 of tau1 mRNA); and SEQ ID NO:8 (nucleotides 1-240 of tau1 mRNA).

Other suitable target sequences will be readily apparent upon inspection of a sequence alignment of, e.g., SEQ ID NO:1 (tau isoform 1 mRNA; GenBank NM_016835), SEQ ID NO:2 (tau isoform 2 mRNA; GenBank NM_005910); SEQ ID NO:3 (tau isoform 3 mRNA; GenBank NM_016834), SEQ ID NO:4 (tau isoform 4 mRNA; GenBank NM_016841), SEQ ID NO:5 (tau isoform 5 mRNA; GenBank NM_001123067), and SEQ ID NO:6 (tau isoform 6 mRNA; GenBank NM_001123066).

It should be understood that the sequences provided above are the target sequences of the mRNAs encoding the target gene, and that the siRNA oligonucleotides used would comprise a sequence complementary to the target.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, Cell., 110, 563-574 and Schwarz et al., 2002, Molecular Cell, 10, 537-568), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at the post-transcriptional level or the pre-transcriptional level. In a non-limiting example, epigenetic regulation of gene expression by siNA molecules of the invention can result from siNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, for example, two regions of tau.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Eamshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; each of which are hereby incorporated in their totality by reference herein). In view of such teachings, similar modifications can be used as described herein to modify the siNA nucleic acid molecules of disclosed herein so long as the ability of siNA to promote RNAi in cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, Nucleic Acids Res. 23, 2677; Caruthers et al., 1992, Methods in Enzymology 211, 3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enhanced affinity and specificity to nucleic acid targets (see, e.g., Lin et al. 1998, J. Am. Chem. Soc., 120, 8531-8532). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., Wengel et al., WO 00/66604 and WO 99/14226).

siNA molecules can be provided as conjugates and/or complexes, e.g., to facilitate delivery of siNA molecules into a cell. Exemplary conjugates and/or complexes include those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, polymerase chain reaction (PCR)-generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Minis, Madison, Wis.).

An interfering RNA can be delivered in a delivery system that provides tissue targetable delivery. In addition, a suitable formulation for an interfering nucleic acid can include one or more additional properties: 1) nucleic acid binding into a core that can release the siRNA into the cytoplasm; 2) protection from non-specific interactions; 3) and tissue targeting that provides cell uptake. In some embodiments, the composition comprises a modular polymer conjugate targeting hippocampal neurons (e.g., interneurons) by coupling a peptide ligand specific for those cells to one end of a protective polymer, coupled at its other end to a cationic carrier for nucleic acids. For example, a suitable polymer conjugate can have three functional domains: peptide ligand specific for a target cell; protective polymer; and cationic carrier for nucleic acids. Another suitable formulation includes surface coatings attached to a preformed nanoparticle.

Suitable formulations for delivery of an interfering nucleic acid include polymers, polymer conjugates, lipids, micelles, self-assembly colloids, nanoparticles, sterically stabilized nanoparticles, and ligand-directed nanoparticles.

Recombinant Expression Vector

In some embodiments, a subject method involves administering to an individual in need thereof an effective amount of a recombinant expression vector that provides for production of a nucleic acid that reduces the level of tau polypeptide in a GABAergic interneuron, e.g., a recombinant expression vector comprising a nucleotide sequence that encodes an interfering nucleic acid that selectively reduces the level of a tau polypeptide in a cell that produces tau. Thus, in some embodiments, a recombinant expression vector is administered to an individual in need thereof, where the recombinant expression vector comprises a nucleotide sequence encoding an interfering RNA that specifically reduces a tau transcript and/or polypeptide in a cell (e.g., in a GABAergic interneuron). In some embodiments, the nucleotide sequence encoding an interfering RNA that specifically reduces a tau transcript and/or polypeptide in a cell is operably linked to a transcriptional control element (e.g., a promoter) that is active in a GABAergic interneuron.

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

Non-limiting examples of suitable eukaryotic promoters (promoters functional in a eukaryotic cell) include cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A recombinant vector will in some embodiments include one or more selectable markers. In addition, the expression vectors will in many embodiments contain one or more selectable marker genes to provide a phenotypic trait for selection of transformed host cells such as dihydrofolate reductase or neomycin resistance for eukaryotic cell culture.

Other gene delivery vehicles and methods may be employed, including polycationic condensed DNA linked or unlinked to killed adenovirus alone, for example Curiel (1992) Hum. Gene Ther. 3:147-154; ligand linked DNA, for example see Wu (1989) J. Biol. Chem. 264:16985-16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) Mol. Cell Biol. 14:2411-2418, and in Woffendin (1994) Proc. Natl. Acad. Sci. 91:1581-1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 524 968.

Liposome or lipid nucleic acid delivery vehicles can also be used. Liposome complexes for gene delivery are described in, e.g., U.S. Pat. No. 7,001,614. For example, liposomes comprising DOTAP and at least one cholesterol and/or cholesterol-derivative, present in a molar ratio range of 2.0 mM 10 mM provide an effective delivery system, e.g., where the molar ratio of DOTAP to cholesterol is 1:1 3:1. The cationic lipid N-[(2,3-dioleoyloxy)propyl]-L-lysinamide (LADOP) can be used in a composition for delivering a polynucleotide, where LADOP-containing liposomes are described in, e.g., U.S. Pat. No. 7,067,697. Liposome formulations comprising amphipathic lipids having a polar headgroup and aliphatic components capable of promoting transfection are suitable for use and are described in, e.g., U.S. Pat. No. 6,433,017. Lipid-conjugated polyamide compounds can be used to deliver nucleic acid; see, e.g., U.S. Pat. No. 7,214,384.

Suitable synthetic polymer-based carrier vehicles are described in, e.g., U.S. Pat. No. 6,312,727. Further non-viral delivery suitable for use includes mechanical delivery systems such as the approach described in Woffendin et al. (1994) Proc. Natl. Acad. Sci. USA 91:11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Genetically Modified Stem Cells

A stem cell used in a subject method is genetically modified in such a way as to reduce the level of tau polypeptide produced by the stem cell or a progeny of the stem cell. A parent (or "host") stem cell is genetically modified with an exogenous nucleic acid. The exogenous nucleic acid will in some embodiments comprise a nucleotide sequence that has sufficient homology to an endogenous tau polypeptide-encoding nucleic acid such that the exogenous nucleic acid will undergo homologous recombination with the endogenous tau polypeptide-encoding nucleic acid and will functionally disable the endogenous tau polypeptide-encoding nucleic acid. The term "functionally disabled," as used herein, refers to a genetic modification of a nucleic acid, which modification results in production of a gene product encoded by the nucleic acid that is produced at below normal levels, and/or is non-functional.

In some embodiments, the endogenous tau gene of a genetically modified stem cell is deleted. Any method for deleting a gene can be used. For example, a recombinase-mediated knockout method can be used, e.g., using a Cre/Lox system (the Cre/lox site-specific recombination system known in the art employs the bacteriophage P1 protein Cre recombinase and its recognition sequence loxP; see Rajewsky et al., J. Clin. Invest., 98:600-603 (1996); Sauer, Methods, 14:381-392 (1998); Gu et al., Cell, 73:1155-1164 (1993); Araki et al., Proc. Natl. Acad. Sci. USA, 92:160-164 (1995); Lakso et al., Proc. Natl. Acad. Sci. USA, 89:6232-6236 (1992); and Orban et al., Proc. Natl. Acad. Sci. USA, 89:6861-6865 (1992)); a FLP/FRT recombination system (see, e.g., Brand and Perrimon, 1993, Development 118:401-415); and the like. As another example, a deletion-based conditional knockout method can be used. As another example, e.g., as described in U.S. Pat. No. 7,625,755, an inducible gene silencer comprising: a splice acceptor sequence; an internal ribosomal entry site (IRES) sequence; a nucleotide sequence coding for a reporter protein; a polyadenylation sequence; and a pair of oppositely oriented recombination site sequences, which cause single cycle inversions in the presence of a suitable recombinase enzyme, flanking the aforementioned elements, can be used.

Alternatively, mutations that can cause reduced expression level (e.g., reduced transcription and/or translation efficiency, and decreased mRNA stability) of an endogenous tau-encoding nucleic acid may also be introduced into an endogenous tau gene by homologous recombination.

In addition, cells that have been genetically altered with recombinant genes or by antisense technology, to provide a gain or loss of genetic function, may be utilized with the invention. Methods for generating genetically modified cells are known in the art, see for example "Current Protocols in Molecular Biology", Ausubel et al., eds, John Wiley & Sons, New York, N.Y., 2000. The genetic alteration may be a knock-out, usually where homologous recombination results in a deletion that knocks out expression of a targeted gene; or a knock-in, where a genetic sequence not normally present in the cell is stably introduced.

A variety of methods can be used to achieve a knock-out, including site-specific recombination, expression of antisense or dominant negative mutations, and the like. Knock-outs have a partial or complete loss of function in one or both alleles of the endogenous gene in the case of gene targeting. In some embodiments, expression of the targeted gene product is undetectable or insignificant in the cells being analyzed; this may be achieved by introduction of a disruption of the coding sequence, e.g. insertion of one or more stop codons, insertion of a DNA fragment, etc., deletion of coding sequence, substitution of stop codons for coding sequence, etc. In some cases the introduced sequences are ultimately deleted from the genome, leaving a net change to the native sequence.

Different approaches may be used to achieve the "knockout". A chromosomal deletion of all or part of the native gene may be induced, including deletions of the non-coding regions, particularly the promoter region, 3' regulatory sequences, enhancers, or deletions of gene that activate expression of the targeted genes. A functional knock-out may also be achieved by the introduction of an anti-sense construct that blocks expression of the native genes (for example, see Li and Cohen (1996) Cell 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration.

The genetic construct may be introduced into tissues or host cells by any number of routes, including calcium phosphate transfection, viral infection, microinjection, electroporation or fusion of vesicles. Jet injection may also be used for intramuscular administration, as described by Furth et al. (1992), Anal. Biochem. 205:365-368. The DNA may be coated onto gold microparticles, and delivered intradermally by a particle bombardment device, or "gene gun" as described in the literature (see, for example, Tang et al. (1992), Nature 356:152-154), where gold microprojectiles are coated with the DNA, then bombarded into cells.

A number of selection systems can be used for introducing the genetic changes, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻; hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

The stem cells used for transplantation can be allogeneic, autologous, or xenogeneic, relative to the individual being treated (e.g., the recipient individual into whom the stem cells are being transplanted). For example, in some cases, the stem cells (e.g., NSC or iNSC) are obtained from a human donor individual who is the same as the human individual being treated (the recipient). As another example, in some cases the stem cells (e.g., NSC or iNSC) are obtained from a human donor individual who is other than the human individual being treated (the recipient).

Neural stem cells of various species have been described. See, e.g., WO 93/01275, WO 94/09119, WO 94/10292, WO 94/16718, and Cattaneo et al., Mol. Brain Res., 42, pp. 161-66 (1996). In some embodiments, NSCs, when maintained in certain culture conditions (e.g., a mitogen-containing (e.g., epidermal growth factor or epidermal growth factor plus basic fibroblast growth factor), serum-free culture medium), grow in suspension culture to form aggregates of cells known as "neurospheres."

NSCs can be generated from somatic cells (where the NSCs are referred to as "induced NSCs"); pluripotent stem cells; induced pluripotent stem cells (iPS); or fetal or adult tissue that contains NSCs. Suitable tissue sources of NSCs include, but are not limited to, hippocampus, septal nuclei, cortex, cerebellum, ventral mesencephalon, and spinal cord.

A suitable NSC exhibits one or more of the following properties: 1) expression of Nestin; 2) expression of Sox2; 3) expression of Musashi1; 4) ability to undergo self-renewal, either as a monolayer or in suspension cultures as neurospheres; 5) ability to differentiate into neurons, specific subtypes of neurons, astrocytes, and oligodendrocytes; and 6) morphological characteristics typical for NSCs. A suitable iNSC can also express CD133 and Vimentin. Nestin, Sox2, and Musashi1 are well described in the literature as hallmark genes expressed in NSCs. See, e.g., GenBank Accession Nos. NP_006608, CAA46780, and CAI16338 for Nestin. For Musashi1, see, e.g., GenBank Accession No. BAB69769; and Shu et al. (2002) Biochem. Biophys. Res. Comm. 293:150.

A suitable NSC is generally negative for markers that identify mature neurons, astrocytes, and oligodendrocytes. Thus, e.g., a suitable NSC is generally microtubule-associated protein-2 (MAP2) negative, neuron-specific nuclear protein (NeuN) negative, Tau negative, S100β negative, oligodendrocyte marker O4 negative, and oligodendrocyte lineage transcription factor Olig2 negative. These markers of mature neural markers are well described in the literature. For MAP2, see, e.g., GenBank Accession Nos. AAA59552, AAB48098, AAI43246, and AAH38857. For NeuN, see, e.g., Wolf et al. (1996) J. Histochem. & Cytochem. 44:1167. For S100β, see, e.g., GenBank Accession Nos. NP_006263.1 (H. sapiens S100β); NP_033141 (Mus musculus S100β); CAG46920.1 (Homo sapiens S100β); and see also, Allore et al. (1990) J Biol. Chem. 265:15537. For 04, see, e.g., Schachner et al. (1981) Dev. Biol. 83:328; Bansal et al. (1989) J. Neurosci. Res. 24:548; and Bansal and Pfeiffer (1989) Proc. Natl. Acad. Sci. USA 86:6181. For Olig2, see, e.g., Lu et al. (2001) Proc. Natl. Acad. Sci. USA 98:10851; Ligon et al. (2004) J Neuropathol. Exp. Neurol. 63:499.

Tissue Sources

Suitable tissue sources of neural stem cells include the CNS, including the cerebral cortex, cerebellum, midbrain, brainstem, spinal cord and ventricular tissue; and areas of the peripheral nervous system (PNS) including the carotid body and the adrenal medulla. Exemplary areas include regions in the basal ganglia, e.g., the striatum which consists of the caudate and putamen, or various cell groups, such as the globus pallidus, the subthalamic nucleus, the nucleus basalis, or the substantia nigra pars compacta. In some embodiments, the neural tissue is obtained from ventricular tissue that is found lining CNS ventricles (e.g., lateral ventricles, third ventricle, fourth ventricle, central canal, cerebral aqueduct, etc.) and includes the subependyma.

Non-autologous human neural stem cells can be derived from fetal tissue following elective abortion, or from a post-natal, juvenile or adult organ donor. Autologous neural tissue can be obtained by biopsy, or from patients undergoing neurosurgery in which neural tissue is removed, for example, during epilepsy surgery, temporal lobectomies and hippocampalectomies. Neural stem cells have been isolated from a variety of adult CNS ventricular regions, including the frontal lobe, conus medullaris, thoracic spinal cord, brain stem, and hypothalamus. In each of these cases, the neural stem cell exhibits self-maintenance and generates a large number of progeny which include neurons, astrocytes and oligodendrocytes.

Induced NSCs

Suitable NSCs include induced NSCs (iNSCs). An iNSC can be generated by introducing into a somatic cell one or more of: an exogenous Sox2 polypeptide, an Oct-3/4 polypeptide, an exogenous c-Myc polypeptide, an exogenous Klf4 polypeptide, an exogenous Nanog polypeptide, and an exogenous Lin28 polypeptide.

Sox2 polypeptides, Oct-3/4 polypeptides, c-Myc polypeptides, and Klf4 polypeptides, are known in the art and are described in, e.g., U.S. Patent Publication No. 2009/0191159. Nanog polypeptides and Lin28 polypeptides are known in the art and are described in, e.g., U.S. Patent Publication No. 2009/0047263. See also the following GenBank Accession Nos.: 1) GenBank Accession Nos. NP_002692, NP_001108427; NP_001093427; NP_001009178; and NP_038661 for Oct-3/4; 2) GenBank Accession Nos. NP_004226, NP_001017280, NP_057354, AAP36222, NP_034767, and NP_446165for Klf4 and Klf4 family members; 3) GenBank Accession Nos. NP_002458, NP_001005154, NP_036735, NP_034979, P0C0N9, and NP_001026123 for c-Myc; 4) GenBank Accession Nos. AAP49529 and BAC76999, for Nanog; 5) GenBank Accession Nos. AAH28566 and NP_078950, for Lin28; and 6) GenBank Accession Nos: NP_003097, NP_001098933, NP_035573, ACA58281, BAA09168, NP_001032751, and NP_648694 for Sox2 amino acid sequences.

A multipotent iNSC can be induced from a wide variety of mammalian somatic cells. Examples of suitable mammalian cells include, but are not limited to: fibroblasts (including dermal fibroblasts, human foreskin fibroblasts, etc.), bone marrow-derived mononuclear cells, skeletal muscle cells, adipose cells, peripheral blood mononuclear cells, macrophages, hepatocytes, keratinocytes, oral keratinocytes, hair follicle dermal cells, gastric epithelial cells, lung epithelial cells, synovial cells, kidney cells, skin epithelial cells, and osteoblasts.

A somatic cell can also originate from many different types of tissue, e.g., bone marrow, skin (e.g., dermis, epidermis), muscle, adipose tissue, peripheral blood, foreskin, skeletal muscle, or smooth muscle. The cells can also be derived from neonatal tissue, including, but not limited to: umbilical cord tissues (e.g., the umbilical cord, cord blood, cord blood vessels), the amnion, the placenta, or other various neonatal tissues (e.g., bone marrow fluid, muscle, adipose tissue, peripheral blood, skin, skeletal muscle etc.

A somatic cell can be obtained from any of a variety of mammals, including, e.g., humans, non-human primates, murines (e.g., mice, rats), ungulates (e.g., bovines, equines, ovines, caprines, etc.), felines, canines, etc.

A somatic cell can be derived from neonatal or post-natal tissue collected from a subject within the period from birth, including cesarean birth, to death. For example, the tissue may be from a subject who is >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the tissue is from a human of age 2, 5, 10 or 20 hours. In other examples, the tissue is from a human of age 1 month, 2 months, 3 months, 4 months, 5 months, 6 months, 9 months or 12 months. In some cases, the tissue is from a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 63 years, 65 years, 70 years, 77 years, or 85 years old.

The cells can be from non-embryonic tissue, e.g., at a stage of development later than the embryonic stage. In other cases, the cells may be derived from an embryo. In some cases, the cells may be from tissue at a stage of development later than the fetal stage. In other cases, the cells may be derived from a fetus.

The cells to be induced or reprogrammed can be obtained from a single cell or a population of cells. The population may be homogeneous or heterogeneous. The cells can be a population of cells found in a human cellular sample, e.g., a biopsy or blood sample.

Methods for obtaining human somatic cells are well established, as described in, e.g., Schantz and Ng (2004), A Manual for Primary Human Cell Culture, World Scientific Publishing Co., Pte, Ltd. In some cases, the methods include obtaining a cellular sample, e.g., by a biopsy (e.g., a skin sample), blood draw, or alveolar or other pulmonary lavage. It is to be understood that initial plating densities of cells prepared from a tissue can vary, due to a variety of factors, e.g., expected viability or adherence of cells from that particular tissue.

An exogenous polypeptide can be introduced into a somatic cell by contacting the somatic cell with the exogenous polypeptide (e.g., a Sox2 polypeptide, as described above) wherein the exogenous polypeptide is taken up into the cell.

In some embodiments, an exogenous polypeptide (e.g., a Sox2 polypeptide) comprises a protein transduction domain, e.g., an exogenous polypeptide is linked, covalently or non-covalently, to a protein transduction domain.

"Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an exogenous polypeptide (e.g., a Sox2 polypeptide). In some embodiments, a PTD is covalently linked to the carboxyl terminus of an exogenous polypeptide (e.g., a Sox2 polypeptide). Exemplary protein transduction domains include but are not limited to a minimal undecapeptide protein transduction domain (corresponding to residues 47-57 of HIV-1 TAT comprising YGRKKRRQRRR; SEQ ID NO:9); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an Drosophila Antennapedia protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:10); Transportan GWTLNSAGYLLGKINLKALAALAKKIL (SEQ ID NO:11); KALAWEAKLAKALAKALAKHLAKALAKA-LKCEA (SEQ ID NO:12); and RQIKIWFQNRRMKWKK (SEQ ID NO:13). Exemplary PTDs include but are not limited to, YGRKKRRQRRR (SEQ ID NO:9), RKKRRQRRR (SEQ ID NO:14); an arginine homopolymer of from 3 arginine residues to 50 arginine residues; Exemplary PTD domain amino acid sequences include, but are not limited to, any of the following: YGRKKRRQRRR (SEQ ID NO:9); RKKRRQRR (SEQ ID NO:14); YARAAARQARA (SEQ ID NO:15); THRLPRRRRRR (SEQ ID NO:16); and GGRRARRRRRR (SEQ ID NO:17).

In some embodiments, introduction of an exogenous polypeptide (e.g., an exogenous Sox2 polypeptide) into a somatic cell is achieved by genetic modification of the somatic cell with an exogenous nucleic acid comprising a nucleotide sequence encoding the polypeptide. Exogenous nucleic acids include a recombinant expression vector comprising a nucleotide sequence encoding an exogenous polypeptide (e.g., an exogenous Sox2 polypeptide). Suitable recombinant expression vectors include plasmids, as well as viral-based expression vectors, e.g., lentivirus vectors, adenovirus vectors, adeno-associated virus vectors, etc., which are well known in the art.

iPS Cells

In some embodiments, NSCs are generated from induced pluripotent stem (iPS) cells. iPS cells are generated from somatic cells, including skin fibroblasts, using, e.g., known methods. iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT. iPS can be induced to differentiate into neural cells that express one or more of: βIII-tubulin, tyrosine hydroxylase, AADC, DAT, ChAT, LMX1B, and MAP2. Methods of generating iPS are known in the art, and any such method can be used to generate iPS. See, e.g., Takahashi and Yamanaka (2006) Cell 126:663-676; Yamanaka et. al. (2007) Nature 448:313-7; Wernig et. al. (2007) Nature 448:318-24; Maherali (2007) Cell Stem Cell 1:55-70.

iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28.

iPS cells can be induced to differentiate into neural cells using any of a variety of published protocols (see, e.g., Muotri et al., 2005, Proc. Natl. Acad. Sci. USA. 102:18644; Takahashi et al, 2007, Cell 131:861). For example, in some embodiments, iPS cells are cultured on mitotically inactivated (e.g., mitomycin C-treated or irradiated) mouse embryonic fibroblasts (Specialty Media, Lavellette, N.J.) in DMEM/F12 Glutamax (GIBCO), 20% knockout serum replacement (GIBCO), 0.1 mM nonessential amino acids (GIBCO), 0.1 mM 2-mercaptoethanol (GIBCO), and 4 ng/ml bFGF-2 (R & D Systems). iPS cell neuronal differentiation can be induced by coculturing the iPS cells with PA6 cells for 3-5 weeks under the following differentiation conditions: DMEM/F12 Glutamax (GIBCO), 10% knockout serum replacement (GIBCO), 0.1 mM nonessential amino acids (GIBCO), and 0.1 mM 2-mercaptoethanol (GIBCO). Alkaline phosphatase activity can be measured using the Vector Red Alkaline Phosphatase substrate kit I from Vector Laboratories. Neuronal differentiation can be monitored by immunostaining with various neuronal cell markers.

Combination Therapies

In some embodiments, a subject method further includes administering at least one additional therapeutic agent. Suitable additional therapeutic agents include, but are not limited to, acetylcholinesterase inhibitors, including, but not limited to, Aricept (donepezil), Exelon (rivastigmine), metrifonate, and tacrine (Cognex); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept is generally administered at 50 mg orally per day for 6 weeks, and, if well tolerated by the individual, at 10 mg per day thereafter.

Another suitable additional therapeutic agent is an apoE4 "structure corrector" that reduces apoE4 domain interaction. Agents that reduce apoE4 domain interaction include, e.g., an agent as described in U.S. Patent Publication No. 2006/0073104); and in Ye et al. (2005) Proc. Natl. Acad. Sci. USA 102:18700.

Another suitable additional therapeutic agent is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

Formulations, Dosages, and Routes of Delivery

An agent active agent (e.g., an interfering nucleic acid; a recombinant expression vector; a population of genetically modified stem cells; at least a second therapeutic agent) can be provided together with a pharmaceutically acceptable excipient. Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins. In the discussion, below, of formulations, dosages, and routes of delivery, an "active agent" will refer to an agent discussed herein, e.g., a recombinant expression vector, a population of genetically modified stem cells, or at least a second therapeutic agent, unless otherwise specified.

Nucleic Acids

Nucleic acids can be formulated in a variety of ways in order to facilitate delivery to the surface of the intestinal cells. The form (e.g., liquid, solid, pill, capsule) and composition of the formulation will vary according to the method of administration used. For example, where the formulation is administered orally, the nucleic acid can be formulated as a tablet, pill, capsule, solution (e.g., gel, syrup, slurry, or suspension), or other suitable form.

The formulation can contain components in addition to nucleic acid, where the additional components aid in the delivery of the nucleic acid to the target intestinal cell. The nucleic acid can be present in a pharmaceutical composition of the invention with additional components such as, but not limited to, stabilizing compounds and/or biocompatible pharmaceutical-carriers, e.g., saline, buffered saline, dextrose, or water. The nucleic acid can also be administered alone or in combination with other agents, including other therapeutic agents. The formulation can also contain organic and inorganic compounds to, for example, facilitate nucleic acid delivery to and uptake by the target cell (e.g., detergents, salts, chelating agents, etc.).

Where the nucleic acid formulation is administered orally, the formulation can contain buffering agents or comprise a coating to protect the nucleic acid from stomach acidity and/or facilitate swallowing. In addition or alternatively, the oral formulation can be administered during an interdigestive period (between meals or at bedtime) when stomach pH is less acidic or with the administration of inhibitors of acid secretion such as H2 blockers (e.g., cimetidine) or proton pump inhibitors (e.g., PROLISEC™) The formulation can also comprise a time-release capsule designed to release the nucleic acid upon reaching the surface of the target intestinal cells.

A nucleic acid can be formulated in a complex with a liposome. Such complexes comprise a mixture of lipids which bind to nucleic acid, providing a hydrophobic core and hydrophilic coat which allows the genetic material to be delivered into cells. Suitable liposomes include DOPE (dioleyl phosphatidyl ethanol amine), CUDMEDA (N-(5-cholestrum-3-β-ol 3-urethanyl)-N',N'-dimethylethylene diamine).

Other formulations can also be used for nucleic acids. Such formulations include RNA coupled to a carrier molecule (e.g., an antibody or a, receptor ligand) which facilitates delivery to a target cell. An RNA can be chemically modified. By the term "chemical modification" is meant modifications of nucleic acids to allow, for example, coupling of the nucleic acid compounds to a carrier molecule such as a protein or lipid, or derivative thereof. Exemplary protein carrier molecules include antibodies specific to target cells.

A nucleic acid can be formulated with any of a variety of natural polymers, synthetic polymers, synthetic co-polymers, and the like. Generally, the polymers are biodegradable, or can be readily eliminated from the subject. Naturally occurring polymers include polypeptides and polysaccharides. Suitable synthetic polymers include, but are not limited to, polylysines, and polyethyleneimines (PEI; Boussif et al., PNAS 92:7297-7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

A nucleic acid can be formulated in a lipid-based vehicle. Lipid-based vehicles include cationic liposomes such as disclosed by Felgner et al (U.S. Pat. Nos. 5,264,618 and 5,459,127; PNAS 84:7413-7417, 1987; Annals N.Y. Acad. Sci. 772:126-139, 1995); they may also consist of neutral or negatively charged phospholipids or mixtures thereof including artificial viral envelopes as disclosed by Schreier et al. (U.S. Pat. Nos. 5,252,348 and 5,766,625). Nucleic acid/liposome complexes are suitable, and can comprise a mixture of lipids which bind to nucleic acid by means of cationic charge (electrostatic interaction). Cationic liposomes that are suitable for use include 3β-[N—(N',N'-dimethyl-aminoethane)-carbamoyl]-cholesterol (DC-Chol), 1,2-bis(oleoyloxy-3-trimethylammonio-propane (DOTAP) (see, for example, WO 98/07408), lysinylphosphatidylethanolamine (L-PE), lipopolyamines such as lipospermine, N-(2-hydroxyethyl)-N,N-dimethyl-2,3-bis(dodecyloxy)-1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy) propyl-N,N,N-triethylammonium (DOTMA), DOSPA, DMRIE, GL-67, GL-89, Lipofectin, and Lipofectamine (Thiery et al. (1997) Gene Ther. 4:226-237; Felgner et al., Annals N.Y. Acad. Sci. 772:126-139, 1995; Eastman et al., Hum. Gene Ther. 8:765-773, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also suitable are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

Stem Cells

For administration to a mammalian host, a genetically modified stem cell population (e.g., a genetically modified NSC population) can be formulated as a pharmaceutical composition. A pharmaceutical composition can be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in a subject pharmaceutical composition. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

For example, a genetically modified stem cell population (e.g., a genetically modified NSC population) can be supplied in the form of a pharmaceutical composition comprising an isotonic excipient prepared under sufficiently sterile conditions for human administration. For general principles in medicinal formulation, see, e.g., Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

In some embodiments, a genetically modified stem cell population (e.g., a genetically modified NSC population) is encapsulated, according to known encapsulation technologies, including microencapsulation (see, e.g., U.S. Pat. Nos. 4,352,883; 4,353,888; and 5,084,350). Where the NSCs are encapsulated, in some embodiments the NSCs are encapsulated by macroencapsulation, as described in U.S. Pat. Nos. 5,284,761; 5,158,881; 4,976,859; 4,968,733; 5,800,828 and published PCT patent application WO 95/05452.

A unit dosage form of a genetically modified stem cell population (e.g., a genetically modified NSC population) can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

A genetically modified stem cell population (e.g., a genetically modified NSC population) will in some embodiments be transplanted into a patient according to conventional techniques, into the CNS, as described for example, in U.S. Pat. Nos. 5,082,670 and 5,618,531, or into any other suitable site in the body. In one embodiment, a population of NSCs is transplanted directly into the CNS. Parenchymal and intrathecal sites are also suitable. It will be appreciated that the exact location in the CNS will vary according to the disease state. Cells may be introduced by, for example, stereotaxic implantation or intracerebral grafting into the CNS of a patient.

In some embodiments, a genetically modified NSC population is administered as a cell suspension. In other embodiments, a genetically modified NSC population is administered as neurospheres. In other embodiments, a genetically modified NSC population is administered in an encapsulated form. In other embodiments, a genetically modified NSC population is contained with a reservoir, and the reservoir is implanted into the individual.

A single dose of a genetically modified NSC population can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells. In some embodiments, multiple doses of a genetically modified NSC population are administered to an individual in need of such treatment. Doses can be administered at regular intervals (e.g., once a week, once a month, once every 6 weeks, once every 8 weeks, once every 6 months, etc.). Alternatively doses beyond an initial dose can be administered according to need, as determined by a medical professional, e.g., based on reappearance of symptoms associated with an apoE4-associated neurodegenerative disorder.

Genetically Modified Stem Cells

The present disclosure provides genetically modified stem cells and progeny thereof, where the stem cells (and/or progeny of such stem cells, such as NSCs, etc.) are genetically modified with one or more nucleic acids, and where the genetic modification results in a reduced level of tau polypeptide produced by the genetically modified cell, compared to a parent host cell or compared to a cell (e.g., a neuron) that normally produces tau.

Tau amino acid sequences are known in the art, as are nucleotide sequences encoding tau polypeptides. See, e.g., the nucleotide and amino acid sequences found under the GenBank accession numbers in parentheses in the following: Human Tau transcript variant 1 mRNA (NM_016835.3) and isoform 1 protein (NP_058519.2); human Tau transcript variant 2 mRNA (NM_005910.4) and isoform 2 protein (NP_005901.2); human Tau transcript variant 3 mRNA (NM_016834.3) and isoform 3 protein (NP_058518.1); human Tau transcript variant 4 mRNA (NM_016841.3) and isoform 4 protein (NP_058525.1); human Tau transcript variant 5 mRNA (NM_001123067.2) and isoform 5 protein (NP_001116539.1); and human Tau transcript variant 6 mRNA (NM_001123066.2) and isoform 6 protein (NP_001116539.1).

A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence set forth in any one of GenBank Accession Nos. NP_058519, NP_005901, NP_058518, NP_058525, NP_001116539, and NP_001116539.

A tau polypeptide can comprise an amino acid sequence having at least about 75%, at least about 80%, at least about 85%, at least about 90%, at least about 95%, at least about 98%, at least about 99%, or 100%, amino acid sequence identity with an amino acid sequence encoded by any one of SEQ ID NOs:1-6. A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence encoded by SEQ ID NO:1. A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence encoded by SEQ ID NO:2. A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence encoded by SEQ ID NO:3. A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence encoded by SEQ ID NO:4. A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence encoded by SEQ ID NO:5. A tau polypeptide can comprise an amino acid sequence having at least about 75%, at least about 80%, at least about 85%, at least about 90%, at least about 95%, at least about 98%, at least about 99%, or 100%, amino acid sequence identity with the amino acid sequence encoded by SEQ ID NO:6.

A subject genetically modified stem cell and/or a progeny thereof, can synthesize less than about 80%, less than about 70%, less than about 50%, less than about 25%, less than about 10%, less than about 5%, or less than about 1%, of the amount of tau polypeptides synthesized by a parent (control) stem cell or progeny thereof that has not been genetically modified so as to reduce the level of tau transcript and/or polypeptide.

Methods of generating a subject genetically modified stem cell are described above.

The present disclosure provides a composition comprising a subject genetically modified stem cell, or progeny thereof.

A subject composition various components in addition to the genetically modified stem cells. For example, a subject composition can include a subject genetically modified stem cell and a culture medium. In some cases, the culture medium comprises one or more growth factors. In some embodiments, the culture medium is a serum-free culture medium. In some cases, the composition comprises genetically modified stem cells and a cryopreservative agent, e.g., a cryopreservation medium.

A subject composition can include a subject genetically modified stem cell and a matrix, e.g., a matrix component. Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly (propylene glycol) flanked by two hydrophilic blocks of poly(ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

The cell density in a subject iNSC/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a sphere, etc.

Subjects Suitable for Treatment

A variety of subjects are suitable for treatment with a subject method. Suitable subjects include any individual, particularly a human, who has an apoE4-associated disorder, who is at risk for developing an apoE-associated disorder, who has had an apoE-associated disorder and is at risk for recurrence of the apoE4-associated disorder, or who is recovering from an apoE4-associated disorder.

Subjects suitable for treatment with a subject method include individuals who have one apoE4 allele; and individuals who have two apoE4 alleles. In other words, suitable subjects include those who are homozygous for apoE4 and those who are heterozygous for apoE4. For example, an individual can have an apoE3/apoE4 genotype, or an apoE4/apoE4 genotype. In some embodiments, the subject has been diagnosed as having Alzheimer's disease.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: GABAergic Interneuron Dysfunction Impairs Hippocampal Neurogenesis in Adult Apolipoprotein E4 Knockin Mice It is shown that apoE4-KI mice have a significant age-dependent decrease in hilar GABAergic interneurons that correlates with the extent of apoE4-induced learning and memory deficits in aged mice. In neurotoxic apoE4 fragment transgenic mice, the interneuron loss was even more pronounced and correlated with the extent of learning and memory deficits. The interneuron loss and learning and memory deficits in these mice were prevented by tau removal, and the prevention was abolished by blocking GABA signaling with picrotoxin. In both groups of mice, the GABAA receptor potentiator pentobarbital rescued the learning and memory deficits. Thus, apoE4 causes age- and tau-dependent hilar GABAergic interneuron impairment, leading to learning and memory deficits in mice.

Materials and Methods

Reagents and Cell Culture.

Minimal essential medium (MEM), Opti-MEM, and fetal bovine serum were from Invitrogen. Primary hippocampal neuronal cultures were prepared from P0 pups of apoE4 (Δ272-299)mE$^{-/-}$Tau$^{+/+}$, apoE4(Δ272-299)mE$^{-/-}$ Tau$^{-/-}$, mE$^{-/-}$Tau$^{+/+}$, mE$^{-/-}$Tau$^{-/-}$ and wildtype mice, as reported (Li et al., 2009). Hippocampi were isolated on postnatal day 0, and dissociated cells were plated at 125,000 cells/ml in Neurobasal medium supplemented with B27, 100 U/ml penicillin G, and 100 μg/ml streptomycin. The genotypes of cultures were determined by polymerase chain reaction (PCR) analysis of the tails of the pups from which the cells were obtained. After 14 days in vitro, the cultures were fixed in 4% paraformaldehyde in phosphate-buffered saline (135 mM NaCl, 2.7 mM KCl, 43 mM Na$_2$HPO$_4$, 14 mM KH$_2$PO$_4$, pH 7.4) for 30 min at room temperature. After permeabilization in phosphate-buffered saline with 0.1% Triton for 10 min, cells were placed in blocking buffer (phosphate-buffered saline with 10% normal serum from the same species that produced the secondary antibody and 0.01% Triton) for 30 min. Primary anti-GAD67 (1:250; Chemicon) were applied overnight at 4° C. and visualized with anti-mouse (GAD67) IgG conjugated with Alexa Fluor 488. Cells were counter-stained with 4',6-diamidino-2-phenylindole (DAPI). To measure GABAergic neuronal survival in hippocampal neuron cultures, GAD67-positive neurons were counted in 15-30 random fields under a fluorescence microscope at 200× magnification (Li et al., 2009).

Mice and Treatments.

Human apoE3-KI and apoE4-KI mice (Sullivan et al., 2004) were from Taconic. Tau−/− mice (Dawson et al., 2001) were backcrossed onto the mE−/− background, and mE−/−Tau−/− mice were crossed with apoE4(Δ272-299) mE−/− Tau+/+ mice. Studies were conducted on female mice at 1, 3, 6, 12, 16, or 21 months of age. All mice were on a C57BL/6 genetic background. Some apoE4-KI and apoE4(Δ272-299)mE−/−Tau+/+ mice received daily intraperitoneal injections of pentobarbital (20 mg/kg) or saline in their home cages for 21 days before the first day of Morris Water Maze (MWM) training and 1 h after daily training. Some apoE4(Δ272-299)mE−/−Tau−/− mice were given daily injections of picrotoxin (1 mg/kg) or saline intraperitoneally in their home cages for 3 days before MWM training and 30 min before daily training. Brain tissues were collected after a 1-min transcardial perfusion with 0.9% NaCl. One hemibrain from each mouse was fixed in 4% paraformaldehyde, sectioned (30 μm) with a microtome, and immunostained as described below. All experiments were performed in accordance with NIH and institutional guidelines.

Immunohistochemistry and Image Collection.

Sliding microtome sections (30 μm) were immunostained with the following primary antibodies: polyclonal goat anti-human apoE (1:8000 for fluorescence; Calbiochem), rabbit anti-neuropeptide Y (1:8000 for gamma-diamino butyric acid (DAB); ImmunoStar), rat anti-somatostatin (1:100 for DAB; Chemicon), mouse anti-GAD67 (1:1000 for DAB; Chemicon), mouse anti-MAP2 (1:500 for fluorescence; Sigma), mouse anti-synaptophysin (1:500 for fluorescence; DakoCytomation), and phosphorylation-dependent monoclonal antibody AT8 (p-Ser202; 1:100 for DAB; Endogen). Primary antibodies were detected with biotinylated goat anti-rabbit or goat anti-rat IgG (both 1:200; Vector Laboratories), Alexa Fluor 488-labeled goat anti-rabbit IgG (1:2000; Invitrogen), or Alexa Fluor 594-labeled donkey anti-mouse IgG (1:2000; Invitrogen). Stained sections were examined with a Radiance 2000 laser-scanning confocal system (Bio-Rad) mounted on a Nikon Optiphot-2 microscope. Images were processed with Photoshop CS (Adobe Systems).

Quantitative Analyses of Immunostained Brain Sections.

GABAergic interneurons in the hilus of the dentate gyrus were quantified by counting GAD67−, neuropeptide Y (NPY)−, and somatostatin-positive cells in every tenth serial coronal section throughout the rostrocaudal extent of the hippocampus by an investigator blinded to genotype and treatment (Li et al., 2009). Results are presented as the total number of positive cells counted per hemibrain, multiplied by two (for both hemibrains), and then by 10 (for every tenth serial section).

Morris Water Maze.

The water maze pool (diameter, 122 cm) contained opaque water (22-23° C.) with a platform 10 cm in diameter. The platform was submerged 1.5 cm during hidden platform sessions (Harris et al., 2003; Raber et al., 1998; Roberson et al., 2007) and marked with black-and-white-striped mast (15 cm high) during cued training sessions. Mice were trained to locate the hidden platform (hidden days 1-5) and the cued platform (visible days 1-3) in two daily sessions (3.5 h apart), each consisting of two 60-s trials (hidden and cued training) with a 15-min intertrial interval. The platform location remained constant in the hidden platform sessions but was changed for each cued platform session. Entry points were changed semirandomly between trials. Twenty-four, 72, and 96 hours after the last hidden platform training, a 60-s probe trial (platform removed) was performed. Entry points for the probe trial were in the west quadrant, and the target quadrant was in the southeast quadrant. Performance was monitored with an EthoVision video-tracking system (Noldus Information Technology).

Elevated Plus Maze.

The elevated plus maze tests "emotionality" and unconditioned anxiety-related behaviors that involve a conflict between the rodent's desire to explore a novel environment and anxiogenic elements such as elevation and an unfamiliar, brightly illuminated area (Roberson et al., 2007). The maze consists of two open arms and two closed arms equipped with rows of infrared photo-cells interfaced with a computer (Hamilton). Mice were placed individually into the center of the maze and allowed to explore for 10 min. The number of beam breaks was recorded to calculate the amount of time spent and distance moved in each arm and the number of entries into the open and closed arms. After each mouse was tested, the maze was cleaned with 70% ethanol to standardize odors.

Electrophysiology.

ApoE3-KI and apoE4-KI mice were sacrificed and processed for slice preparation as described (Li et al., 2009). Brains were quickly removed into an ice-cold solution containing (in mM) 110 choline chloride, 2.5 KCl, 1.3 $KH_2PO_4$, 25 $NaHCO_3$, 0.5 $CaCl_2$, 7 $MgCl_2$, 10 dextrose, 1.3 sodium ascorbate, and 0.6 sodium pyruvate (300-305 mOsm). Horizontal slices (350 μm thick) were cut with a Vibratome, maintained in continuously oxygenated external solution (in mM: 125 NaCl, 2.5 KCl, 1.3 $KH_2PO_4$, 25 $NaHCO_3$, 2 $CaCl_2$, 1.3 $MgCl_2$, 1.3 sodium ascorbate, 0.6 sodium pyruvate, 10 dextrose, pH 7.4) at 30° C. for at least 40 min, and incubated at room temperature for at least 60 min before recording. Whole-cell voltage-clamp recordings from dentate gyrus granule cells were obtained with an infrared differential interference contrast video microscopy system. Patch electrodes (3-6 MΩ) were pulled from borosilicate glass capillary tubing (World Precision Instruments) on a horizontal Flaming-Brown microelectrode puller (model P-97, Sutter Instruments). Intracellular patch pipette solution contained (in mM) 120 Cs-gluconate, 10 HEPES, 0.1 EGTA, 15 $CsCl_2$, 4 $MgCl_2$, 4 Mg-ATP, and 0.3 $Na_2$-GTP, pH 7.25 (285-290 mOsm). To measure mIPSCs, slices were perfused with artificial cerebrospinal fluid containing 20 μM DNQX, 50 μM D-AP5, and 1 μM TTX. Whole-cell voltage-clamp data were low-pass filtered at 6 kHz (−3 dB, eight-pole Bessel), digitally sampled at 10 kHz with a Multiclamp 700 A amplifier (Axon Instruments), and acquired with a Digidata-1322 digitizer and pClamp 9.2 software (Axon Instruments). Whole-cell access resistance was monitored throughout the recording, and cells were rejected if values changed by >25%. mIPSCs were analyzed with a program provided by Dr. John Huguenard (Stanford University).

Statistical Analyses.

Values are expressed as mean±SEM or mean±SD. Statistical analyses were performed with GraphPad Prism, Statview 5.0 (SAS Institute) or SPSS-10 (SPSS). Differences between means were assessed by t test, Mann-Whitney U test, one-factor ANOVA, or two-factor ANOVA, followed by Bonferroni, Tukey-Kramer or Fisher's PLSD post hoc tests. $P<0.05$ was considered statistically significant.

Results

Age-Dependent Decrease in GABAergic Interneurons in the Hilus of Dentate Gyrus of Female ApoE4-KI Mice.

To assess the effect of aging and apoE4 on GABAergic interneurons in the hippocampus, their numbers were quantified in the hilus of dentate gyrus of female apoE3-KI and apoE4-KI mice at 1, 3, 6, 12, 16, and 21 months of age. Female mice were studied because they are susceptible to apoE4-induced learning and memory deficits (Raber et al., 1998; Raber et al., 2000). Anti-GAD67 and anti-somatostatin immunostaining, as shown representatively in 16-month-old apoE3-KI and apoE4-KI mice (FIG. 1, panels A-D), revealed a significantly greater age-dependent decrease in GABAergic interneurons in the hilus of the dentate gyrus of female apoE4-KI mice than in age- and sex-matched apoE3-KI mice (FIG. 1, panels E and F). The significant difference between apoE4-KI and apoE3-KI mice was first observed at 6 months and was most pronounced at 16 and 21 months (FIG. 1, panels E and F). ApoE3-KI mice had a milder age-dependent decrease in hilar GABAergic interneurons (FIG. 1, panels E and F). Interestingly, the number of GABAergic interneurons in the hippocampal CA1 area did not differ in apoE3-KI and apoE4-KI mice at 16 months (FIG. 1, panels G-I), suggesting a region-specific detrimental effect of apoE4 on GABAergic interneurons.

Presynaptic GABAergic Input onto Granule Cells is Reduced in Female ApoE4-KI Mice.

Figure 2:
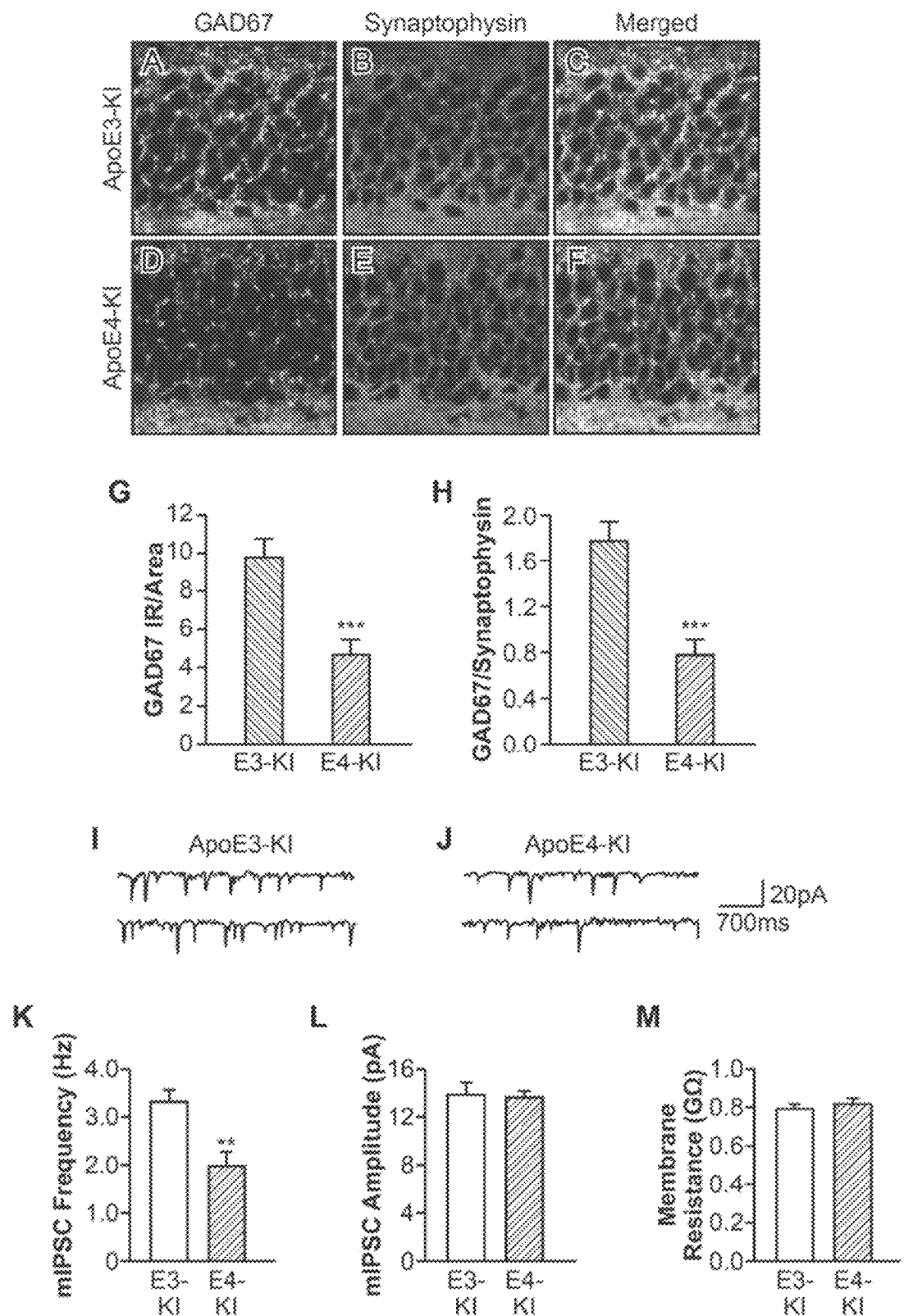
FIG. 2, panels A-M, illustrate that presynaptic GABAergic input onto granule cells is reduced in female ApoE4-KI mice.

The axonal termini of GABAergic interneurons on granule cells in the dentate gyrus of female apoE3-KI and apoE4-KI mice at 16 months of age were assessed by anti-GAD67 and anti-synaptophysin double immunofluorescence staining and confocal imaging analysis. The GABAergic axonal termini on granule cells were significantly decreased at the absolute level (GAD67 fluorescence intensity) and relative to the presynaptic marker synaptophysin (GAD67/synaptophysin ratio) in apoE4-KI mice (FIG. 2, panels A-H). To assess the functional consequence of this finding, whole-cell patch-clamp recordings from granule cells were performed; glutamate currents were blocked with 6,7-dinitroquinoxaline-2,3-dione (DNQX) (20 µM) and D-(-)-2-amino-5-phosphonovaleric acid (D-AP5) (50 µM), and action potential-mediated GABA release was blocked with tetrodotoxin (TTX) (1 µM). Consistent with the above findings, the frequency of miniature inhibitory postsynaptic currents (mIPSCs) was ~40% lower in apoE4-KI mice than in apoE3-KI mice (FIG. 2, panels I-K). The mIPSC amplitude and membrane resistance were not altered significantly (FIG. 2, panels L and M). These results suggest that apoE4-KI mice have fewer functional GABAergic synapses onto granule cells.

Hilar GABAergic Interneuron Impairment Precedes Learning and Memory Deficits in Female ApoE4-KI Mice.

Figure 3:
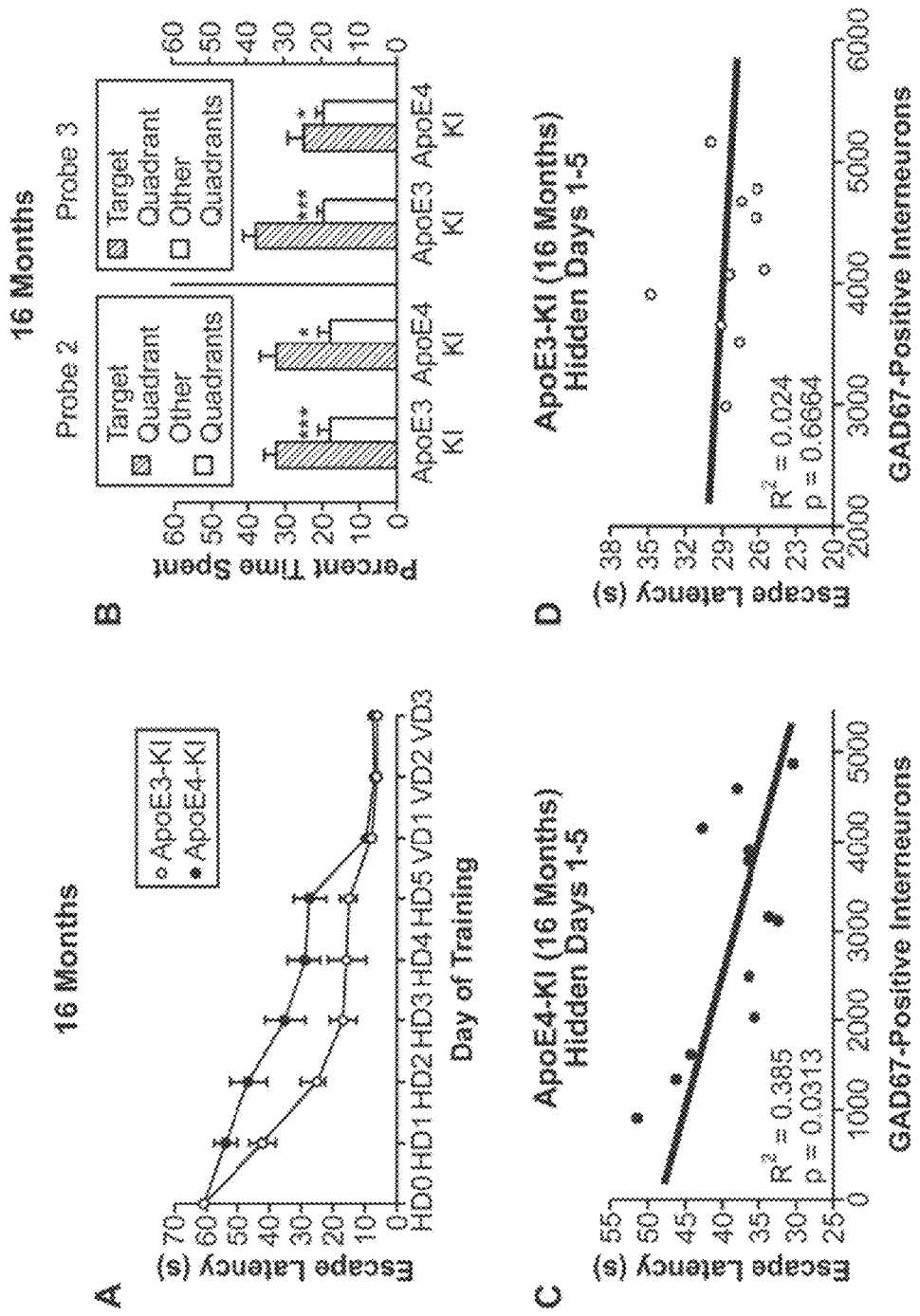
FIG. 3, panels A-H, depict the correlation of hilar GABAergic interneuron impairment with spatial learning deficits in ApoE4-KI mice.
Figure 3:
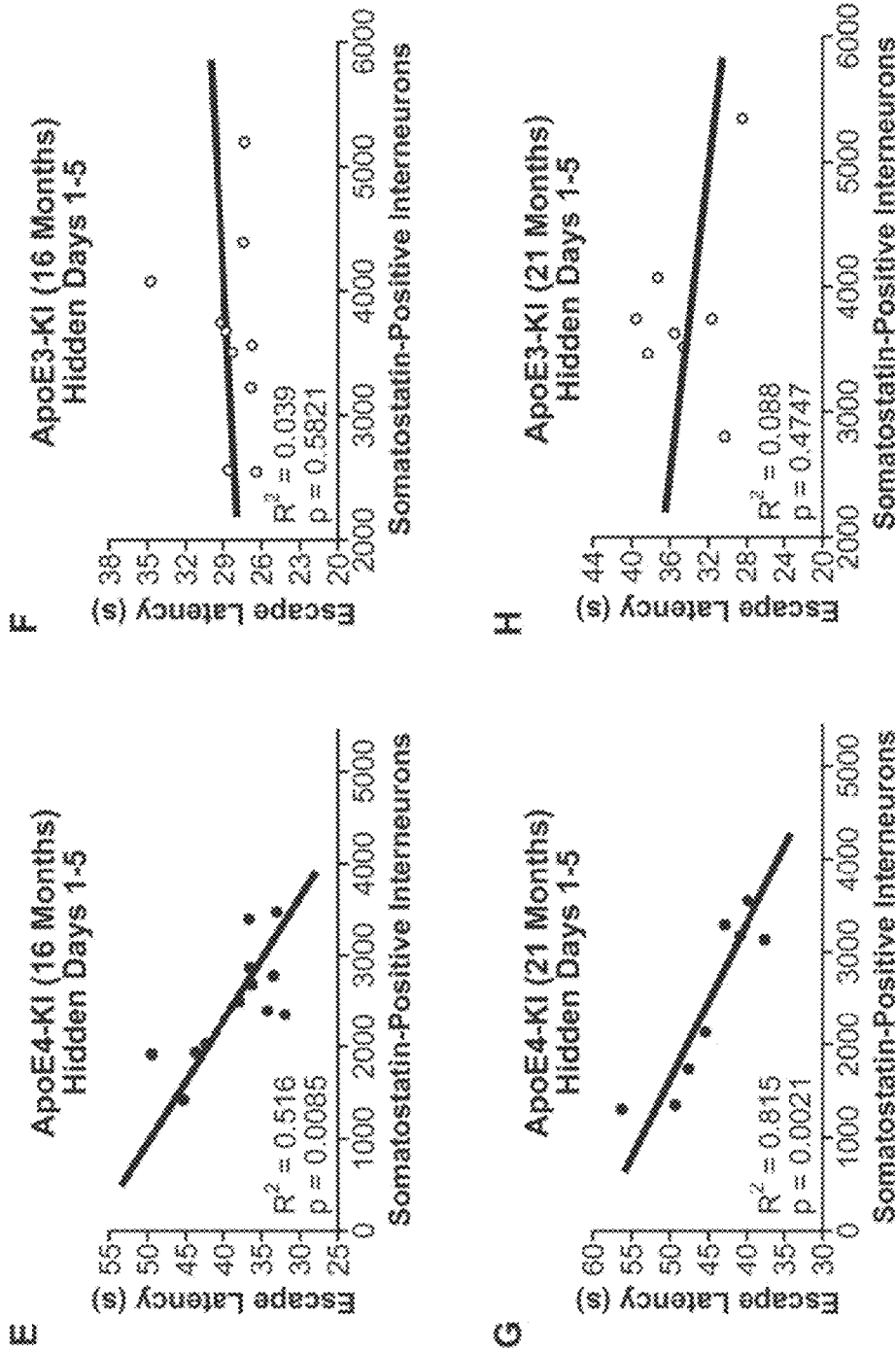
Figure 4:
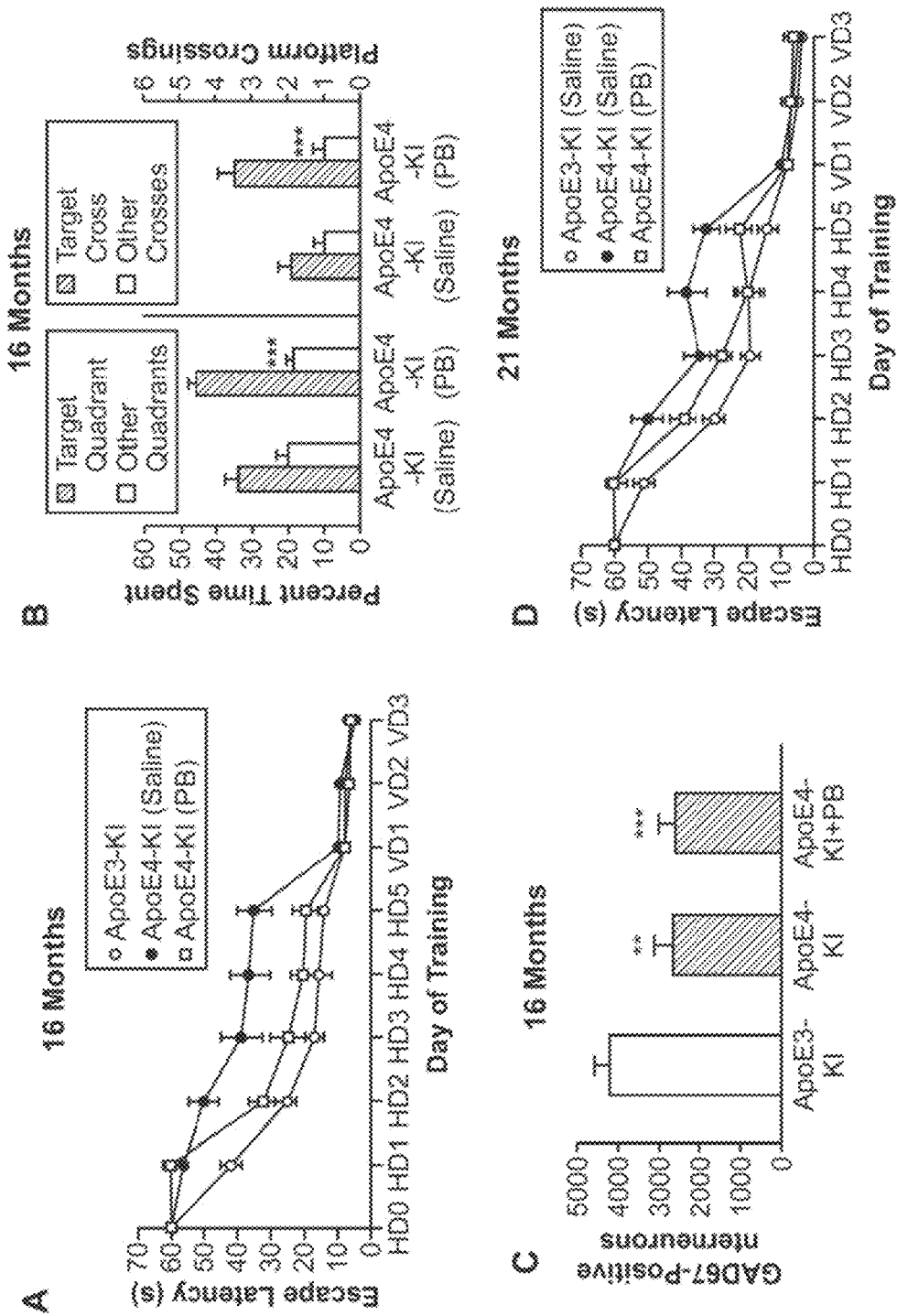
FIG. 4, panels A-D, illustrate that GABAA receptor potentiator pentobarbital rescues spatial learning and memory deficits in ApoE4-KI mice.

Next, the spatial learning and memory of female apoE3-KI and apoE4-KI mice at 12, 16, and 21 months of age was tested in the Morris water maze (MWM). At 12 months, apoE3-KI and apoE4-KI mice performed equally well in the hidden platform and probe trials, suggesting normal learning and memory in both groups. At 16 (FIG. 3, panel A) and 21 (FIG. 4, panel D) months, apoE3-KI mice quickly learned to find the hidden platform, which requires spatial learning, but apoE4-KI mice showed deficits. Swim speeds did not differ, indicating that the impairment was not due to motor deficits. ApoE3-KI and apoE4-KI mice performed equally well in visible platform trials, which test general performance deficits (FIG. 3, panel A and FIG. 4, panel D). In the probe trial 96 h after the last hidden platform trial, 16-month-old apoE4-KI mice had a deficit in memory retention (FIG. 3, panel B, probe 3), although they performed as well as apoE3-KI mice in probe trials at 24 and 72 h (FIG. 3, panel B, probe 2). Thus, hilar GABAergic interneuron impairment, first observed at 6 months of age, precedes the learning and memory deficits, which were first observed at 16 months of age, in apoE4-KI mice.

Hilar GABAergic Interneuron Impairment Correlates with Spatial Learning Deficits in Female ApoE4-KI Mice.

Figure 9:
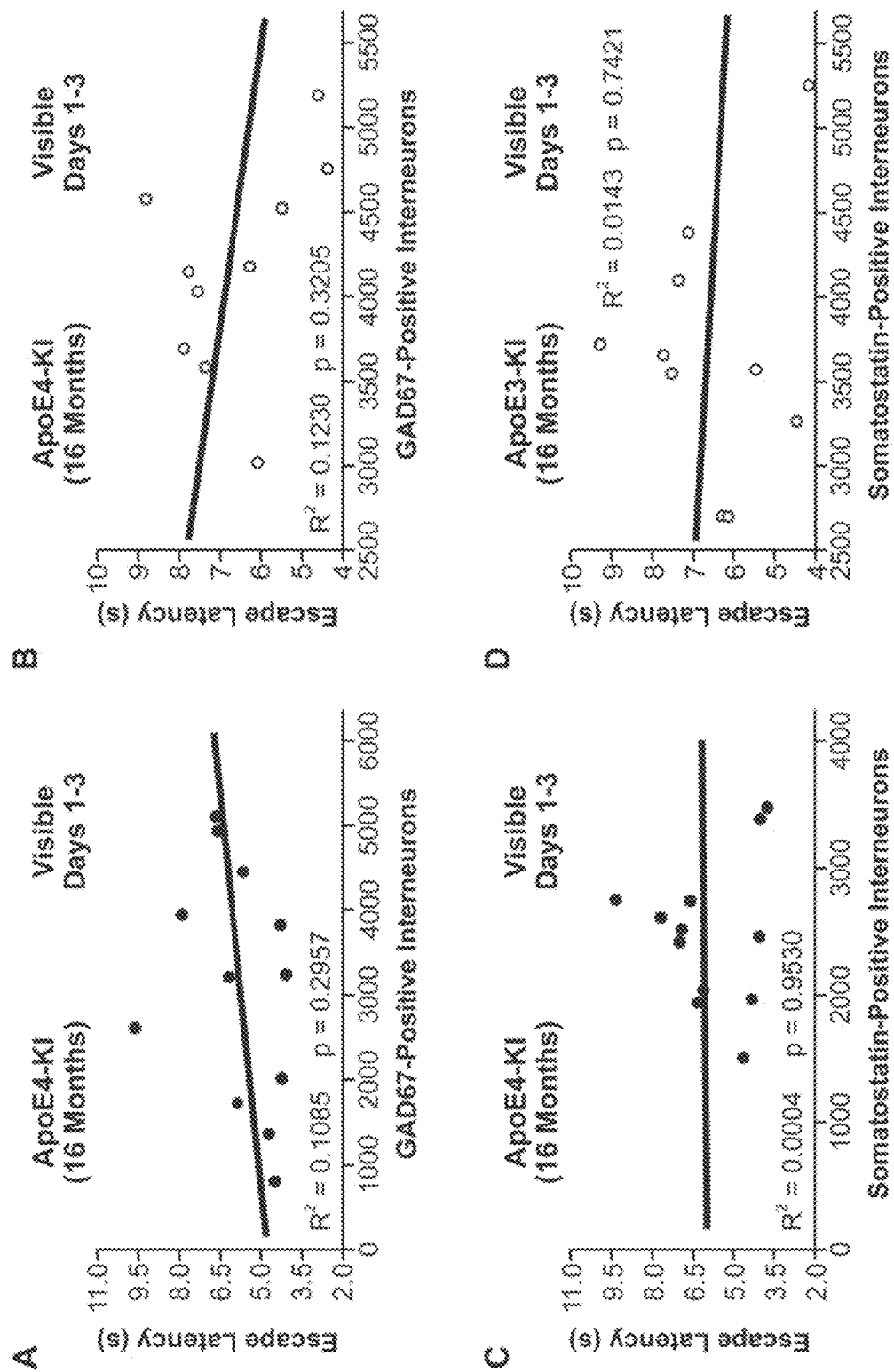
FIG. 9, panels A-F, illustrate the performance in the cued platform trial does not correlate with the number of hilar GABAergic interneurons in apoE3-KI and apoE4-KI mice.
Figure 9:
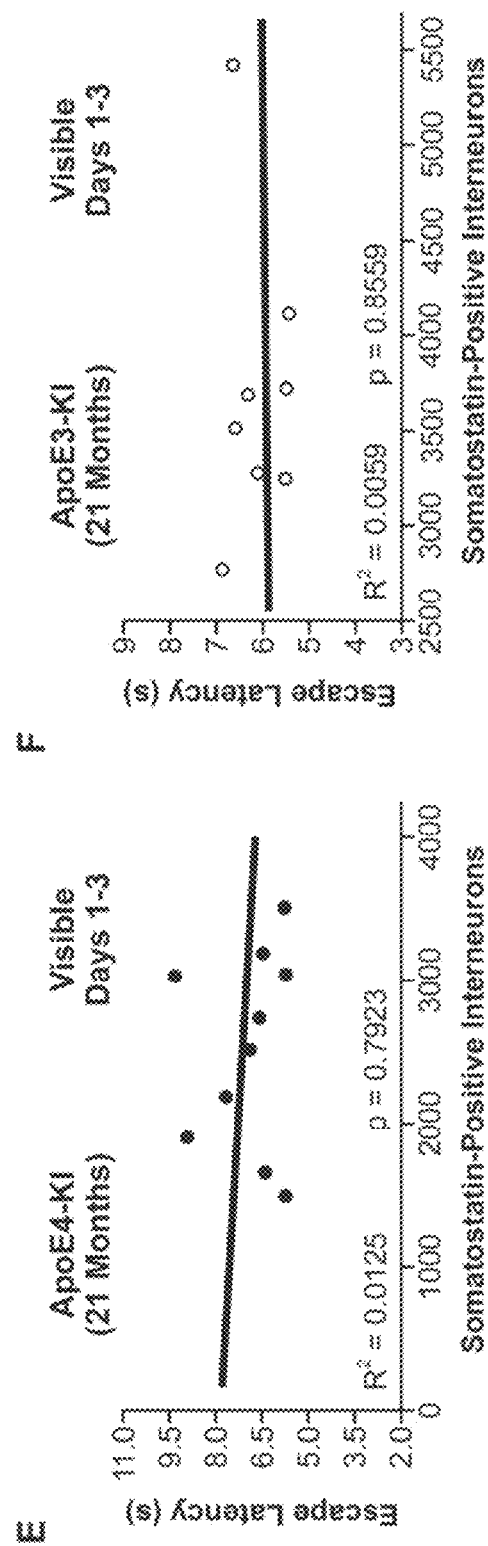

In days 1-5 of the hidden platform trials, the number of hilar GABAergic interneurons correlated inversely with escape latency of apoE4-KI, but not apoE3-KI, mice at 16 months of age (FIG. 3, panels C-F); no correlation was observed in visible platform trials (FIG. 9, panels A-D). Similar results were obtained at 21 months of age (FIG. 3, panels G and H, and FIG. 9, panels E and F). Interestingly, at both ages, all apoE3-KI mice had more than 2500 hilar GABAergic interneurons (FIG. 3, panels D, F, and H), whereas ~50% of the apoE4-KI mice had fewer than 2500 (FIG. 3, panels C, E, and G) and had greater learning deficits in the hidden platform trials (FIG. 3, panels C, E, and G).

The individual numbers of hilar GABAergic interneurons was looked at in female apoE4-KI mice at 6 or 12 months of age, when they also had, on average, significantly fewer hilar GABAergic interneurons than apoE3-KI mice at similar ages (FIG. 1, panels E and F). Interestingly, none of those mice had fewer than 2500 hilar GABAergic interneurons, and none of those mice had learning and memory deficits at 12 months, as mentioned above. Thus, 2500 might be the threshold number of hilar GABAergic interneurons that determines normal versus impaired learning performance of female mice in the MWM.

Pentobarbital Rescues Spatial Learning and Memory Deficits in Female ApoE4-KI Mice.

To determine whether the loss of GABAergic interneurons contributes directly to the learning and memory deficits, 16-month-old female apoE4-KI mice were treated with the GABAA receptor potentiator pentobarbital for 4 weeks. This treatment rescued the learning and memory deficits (FIG. 4, panels A and B) but did not alter the number of hilar GABAergic interneurons (FIG. 4, Panel C). The learning deficit was also rescued in 21-month-old female apoE4-KI mice (FIG. 4, Panel D).

AD-Like Neurodegeneration Occurs in Transgenic Mice Expressing Low Levels of ApoE4(Δ272-299).

It was reported that neurons under stress, including neurons cultured in vitro (Harris et al., 2004b; Xu et al., 2008), express apoE and that neuronal apoE undergoes proteolytic cleavage to generate neurotoxic fragments, with apoE4 being more susceptible to the cleavage than apoE3 (Brecht et al., 2004; Harris et al., 2003; Huang et al., 2001). In primary hippocampal neuronal cultures, apoE4 impairs the survival of GABAergic interneurons by generating more neurotoxic apoE fragments and increasing the levels of phosphorylated tau (p-tau) (Li et al., 2009).

To assess the contributions of apoE4 fragments and p-tau to hilar GABAergic interneuron impairment and behavioral deficits in vivo, transgenic mice were studied expressing low levels of apoE4(Δ272-299), a major neurotoxic fragment in mouse and AD brains (Brecht et al., 2004; Harris et al., 2003), under the control of the neuron-specific Thy-1 promoter. These mice develop AD-like neurodegeneration and spatial learning and memory deficits (Harris et al., 2003). To eliminate confounding effects of mouse apoE, the original apoE4(Δ272-299) transgenic line was crossed with apoE knockout (mE-/-) mice to generate apoE4(Δ272-299) mE-/-Tau+/+ mice. To assess the effect of tau removal on AD-like neuronal and behavioral deficits caused by apoE4 fragments, apoE4(Δ272-299)mE-/-Tau+/- mice were crossed with mE-/-Tau+/- mice to generate littermates of apoE4(Δ272-299)mE-/-Tau+/+, apoE4(Δ272-299)mE-/-Tau-/-, mE-/-Tau+/+, and mE-/-Tau-/- mice. Eliminating endogenous tau did not alter the expression levels of apoE4 (Δ272-299). Age- and sex-matched wildtype mice were included as controls.

Figure 5:
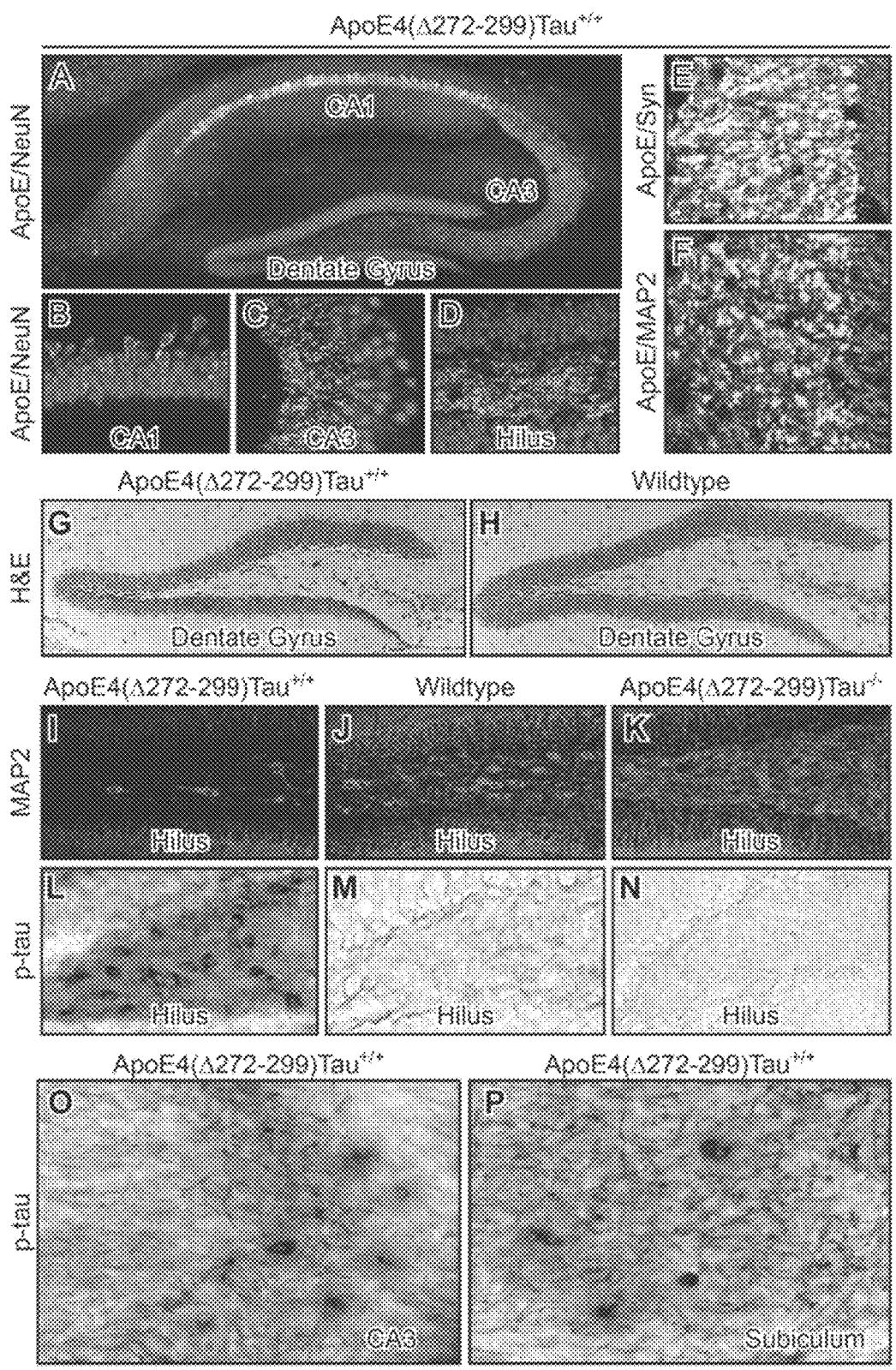
FIG. 5, panels A-P depict localization of apoE4(Δ272-299) in the hippocampus and its effects on neurodegeneration and tau pathology in the presence and absence of Tau.

Morphological studies revealed neuronal deficits in the hippocampus of 12-month-old apoE4(Δ272-299)mE–/–Tau+/+ mice, including presynaptic accumulation of apoE4 fragments as determined by anti-apoE and anti-synaptophysin (a presynaptic marker) or anti-MAP2 (a dendritic marker) double immunostaining (FIG. 5, panels A-F), neurodegeneration as determined by hematoxylin/eosin and anti-MAP2 immunostaining (FIG. 5, panels G-J), and tau pathology as determined by anti-p-tau (AT8 monoclonal antibody) immunostaining (FIG. 5, panels L, M, O, and P) in the hilus of the dentate gyrus, the hippocampal CA3 area, and the subiculum. Neurodegeneration and tau pathology occurred earliest in the hilus (FIG. 5, panels G, J, and L).

Tau Removal Prevents Loss of Hilar GABAergic Interneurons in Female ApoE4(Δ272-299) Mice.

Figure 6:
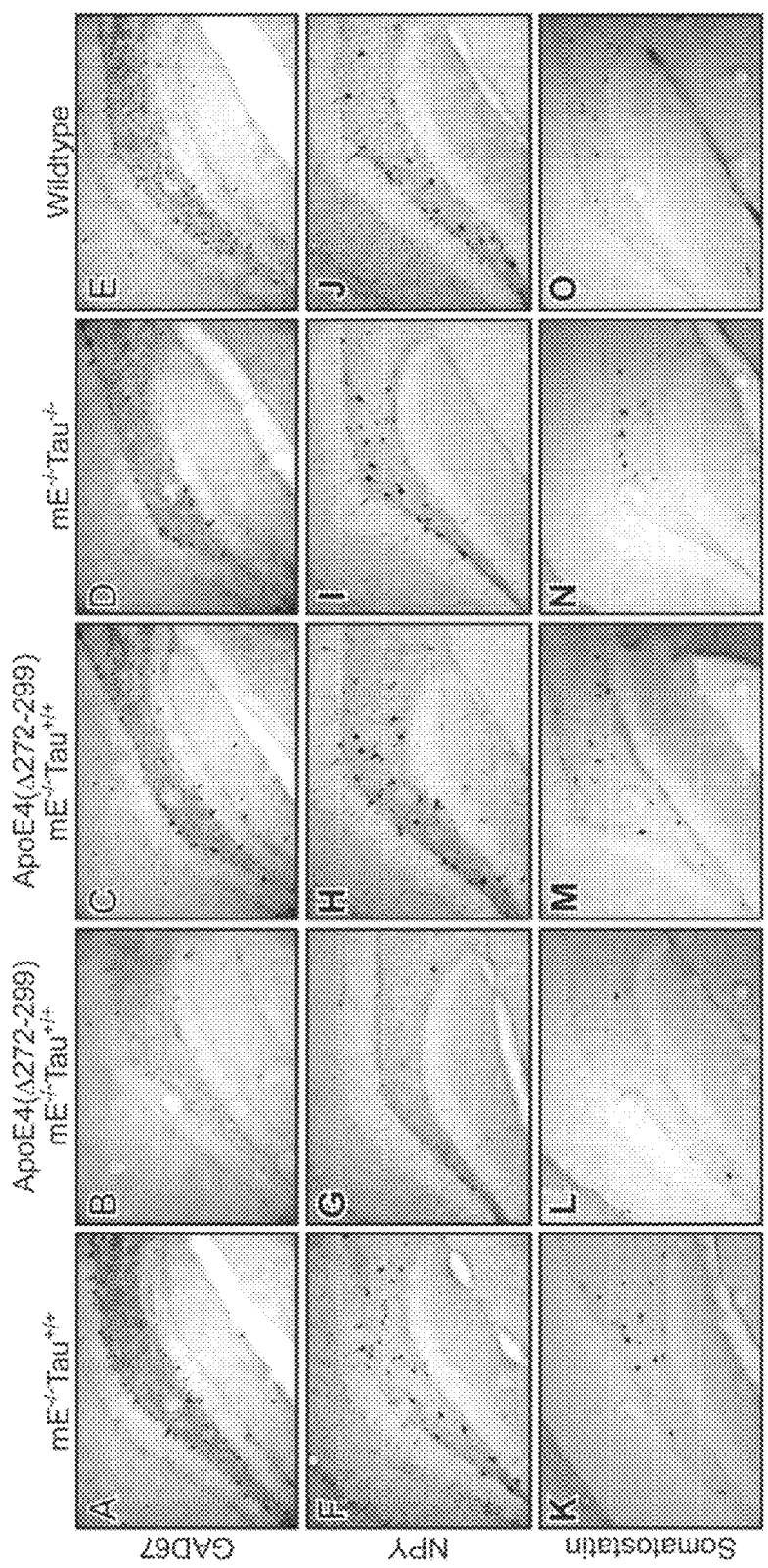
FIG. 6, panels A-R, depict loss of GABAergic interneurons in the hilus of the dentate gyrus of ApoE4(Δ272-299) mE$^{-/-}$Tau$^{+/+}$ mice and rescue by tau removal.
Figure 6:
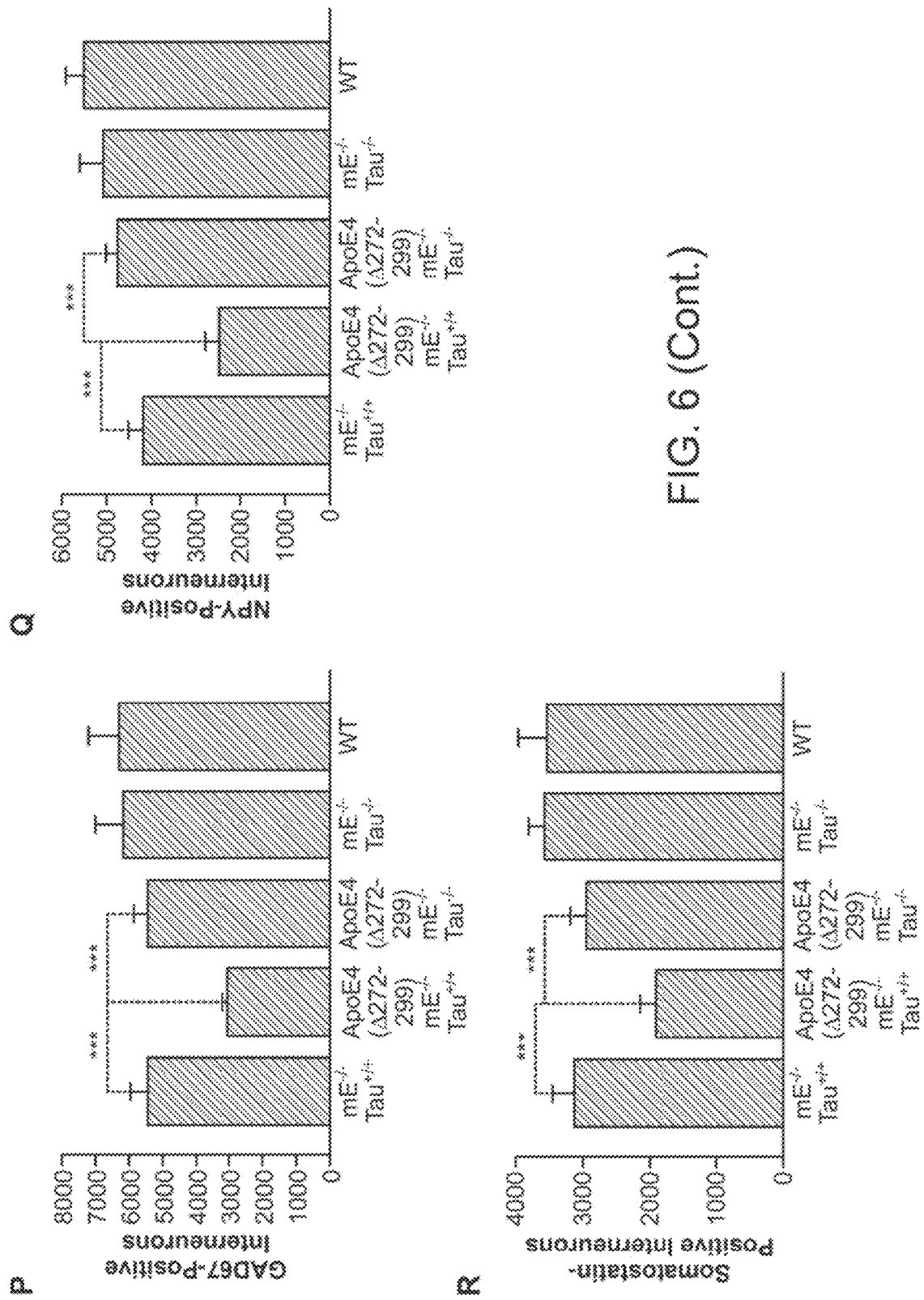

Immunostaining for GAD67 (FIG. 6, panels A-E), neuropeptide Y (NPY) (FIG. 6, panels F-J), and somatostatin (FIG. 6, panels K-0) revealed 40-50% fewer GABAergic interneurons in the hilus of apoE4(Δ272-299)mE–/–Tau+/+ mice than in mE–/–Tau+/+ or wildtype controls (FIG. 6, panels P-R). Eliminating tau prevented neuronal deficits in apoE4 fragment transgenic mice, including loss of GABAergic interneurons in the hilus (FIG. 6), neurodegeneration (compare FIG. 5, panel K to FIG. 5, panel I and FIG. 5, panel J), and tau pathology in hilar interneurons (compare FIG. 5, panel N to FIG. 5, panel L and FIG. 5, panel M).

Figure 7:
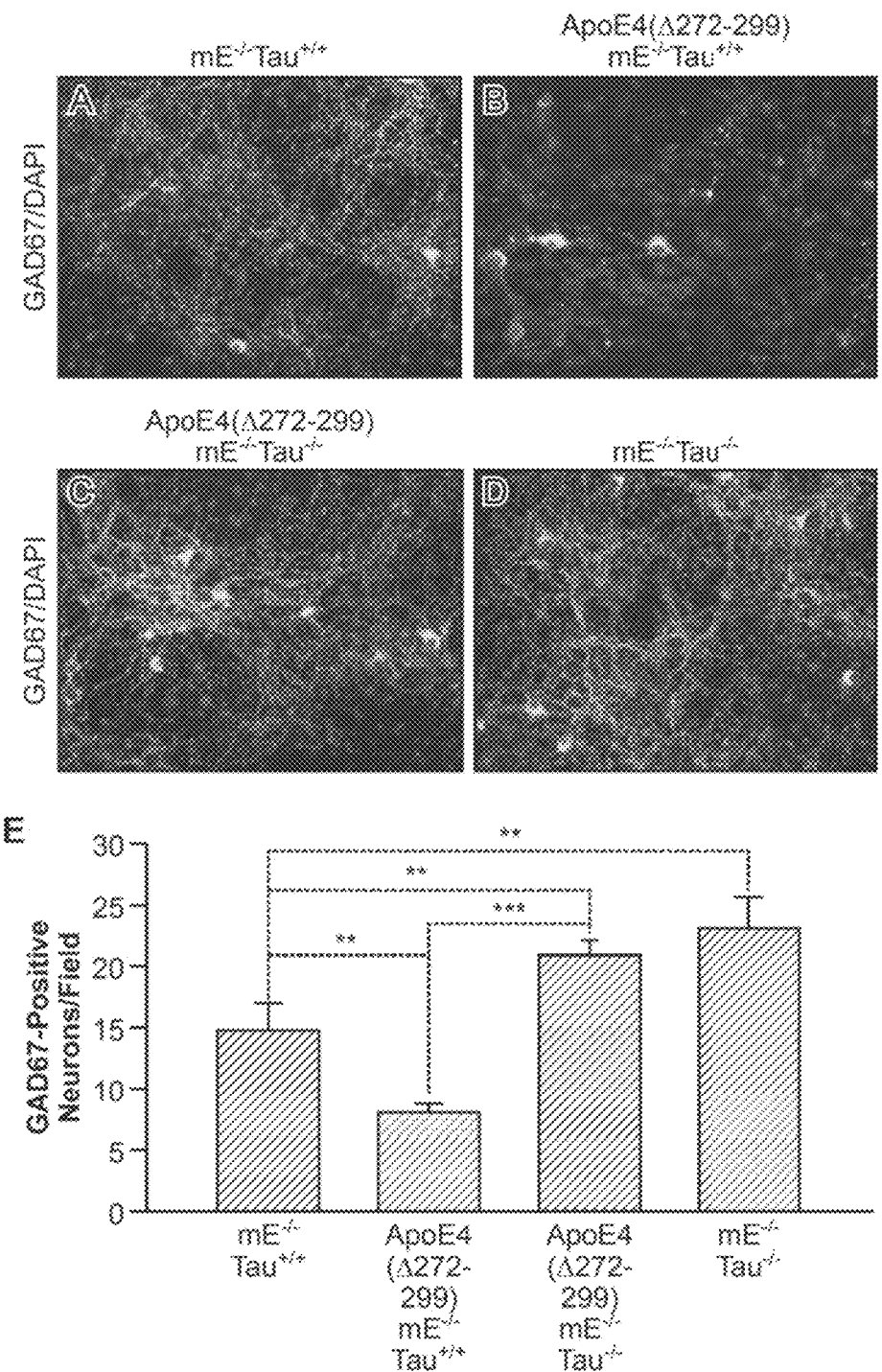
FIG. 7, panels A-E, illustrate that eliminating Tau prevents the neurotoxic effect of ApoE4 fragments on primary hippocampal GABAergic neurons FIG. 8, panels A-H, depict spatial learning and memory deficits in ApoE4(Δ272-299) mE$^{-/-}$Tau$^{+/+}$ mice and rescue by Tau removal.

In 14-day primary hippocampal neuronal cultures, immunostaining for GAD67 (FIG. 7, panel A and FIG. 7, panel B) revealed ~50% fewer GABAergic neurons in cultures from apoE4(Δ272-299)mE–/–Tau+/+ mice than from mE–/–Tau+/+ controls (FIG. 7, panel E) and markedly lower GAD67 immunoreactivity in neurites of surviving GABAergic neurons (compare FIG. 7, panel B to FIG. 7, panel A). Tau removal increased the survival of GABAergic neurons from apoE4(Δ272-299)mE–/– Tau–/– mice to levels higher than in mE–/–Tau+/+ mice (FIG. 7, panels A, C, and E). Removing tau also increased the survival of GABAergic neurons from mE–/–Tau–/– mice to levels higher than those of neurons from mE–/–Tau+/+ mice (FIG. 7, panels A, D, and E). Thus, eliminating endogenous tau rescues apoE4 fragment-caused GABAergic interneuron impairment both in mice and in primary hippocampal neuronal cultures.

Tau Removal Prevents Spatial Learning and Memory Deficits in Female ApoE4(Δ272-299) Mice.

Figure 8:
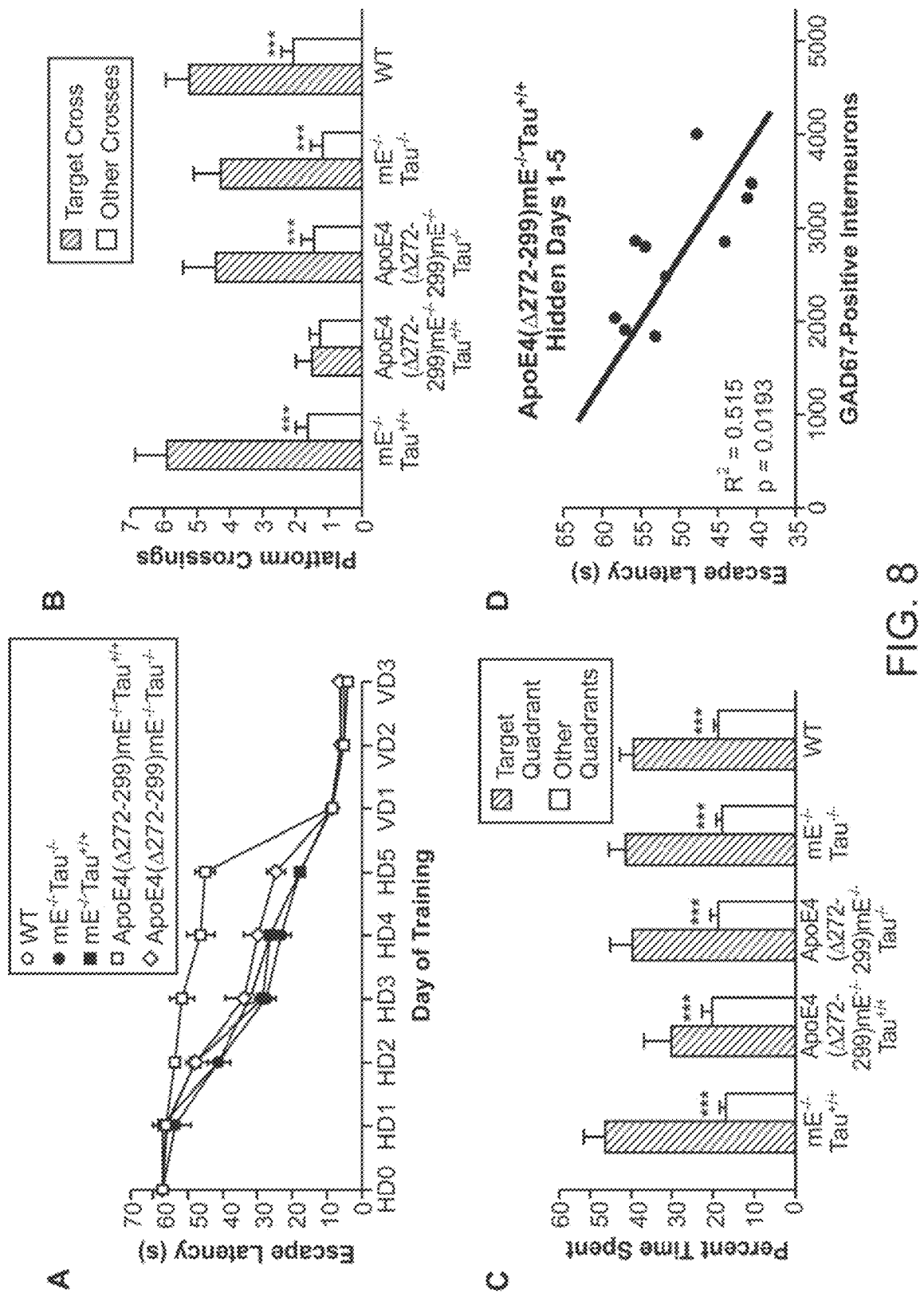
Figure 8:
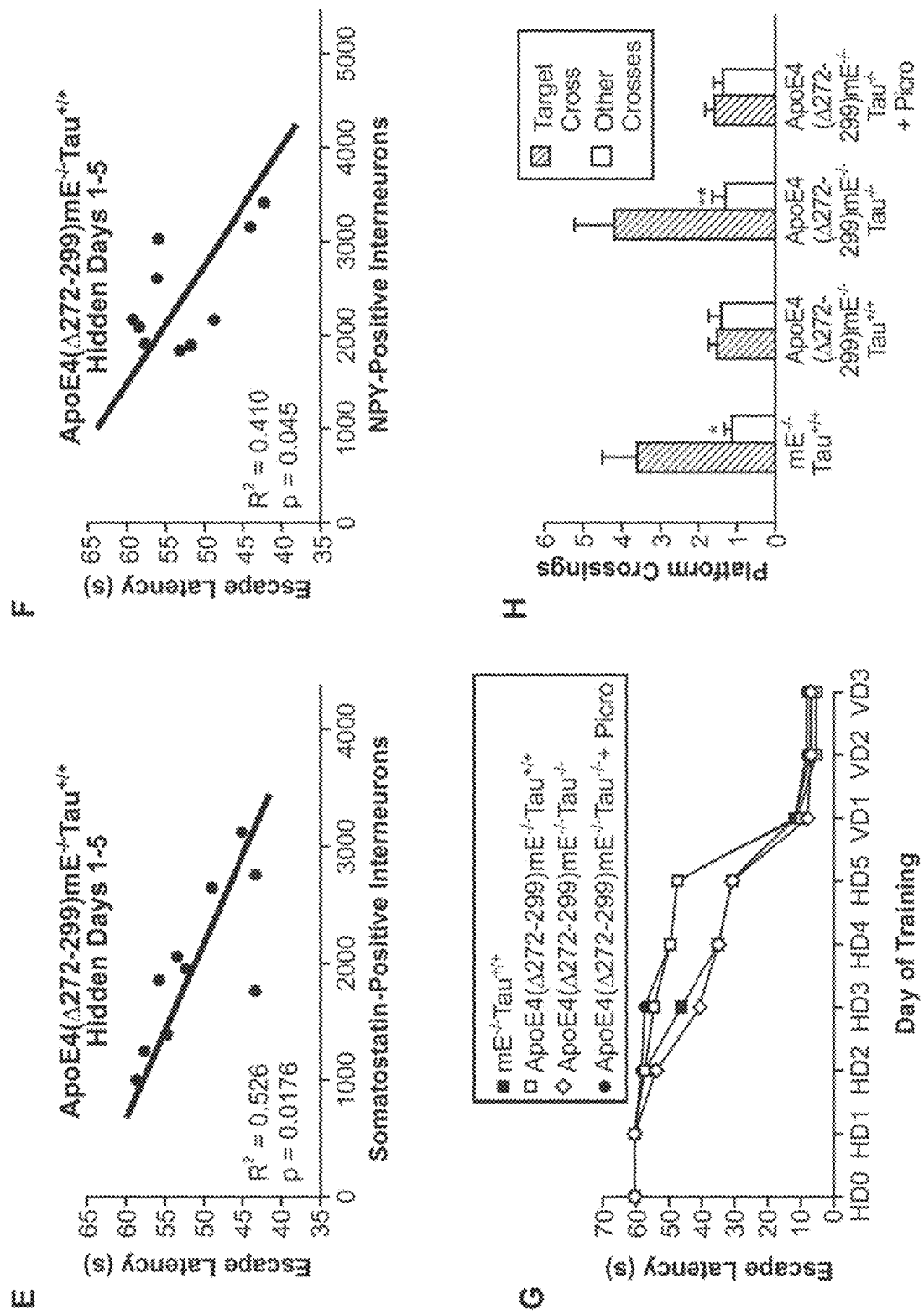

To assess effects of tau removal on learning and memory deficits induced by apoE4 fragments, 12-month-old female mice were tested in the MWM. In the hidden platform trial, mE–/–Tau+/+ and wildtype mice quickly learned the task, but apoE4(Δ272-299)mE–/–Tau+/+ mice showed a deficit (FIG. 8, panel A). Swim speeds of the mice did not differ. ApoE4(Δ272-299)mE–/–Tau–/– mice performed as well as mE–/–Tau+/+ and wildtype mice in the hidden platform trial (FIG. 8, panel A). Thus, tau removal prevented the apoE4 fragment-induced learning deficit. In subsequent visible platform trials, all groups of mice performed equally well (FIG. 8, panel A). In the probe trial 24 h after the last hidden platform trial, apoE4(Δ272-299)mE–/–Tau+/+ mice had deficits in the target crossing and target quadrant tests that were eliminated by tau removal (FIG. 8, panels B and C). Interestingly, in the elevated plus maze, which assesses hippocampus-independent anxiety, apoE4(Δ272-299) mE–/–Tau+/+ mice had increased anxiety that was unaffected by tau removal (FIG. 10, panel A), suggesting that elimination of tau specifically affects hippocampus-dependent learning and memory performance.

Hilar GABAergic Interneuron Impairment Correlates with Spatial Learning Deficits in Female ApoE4(Δ272-299) Mice with Tau.

Figure 10:
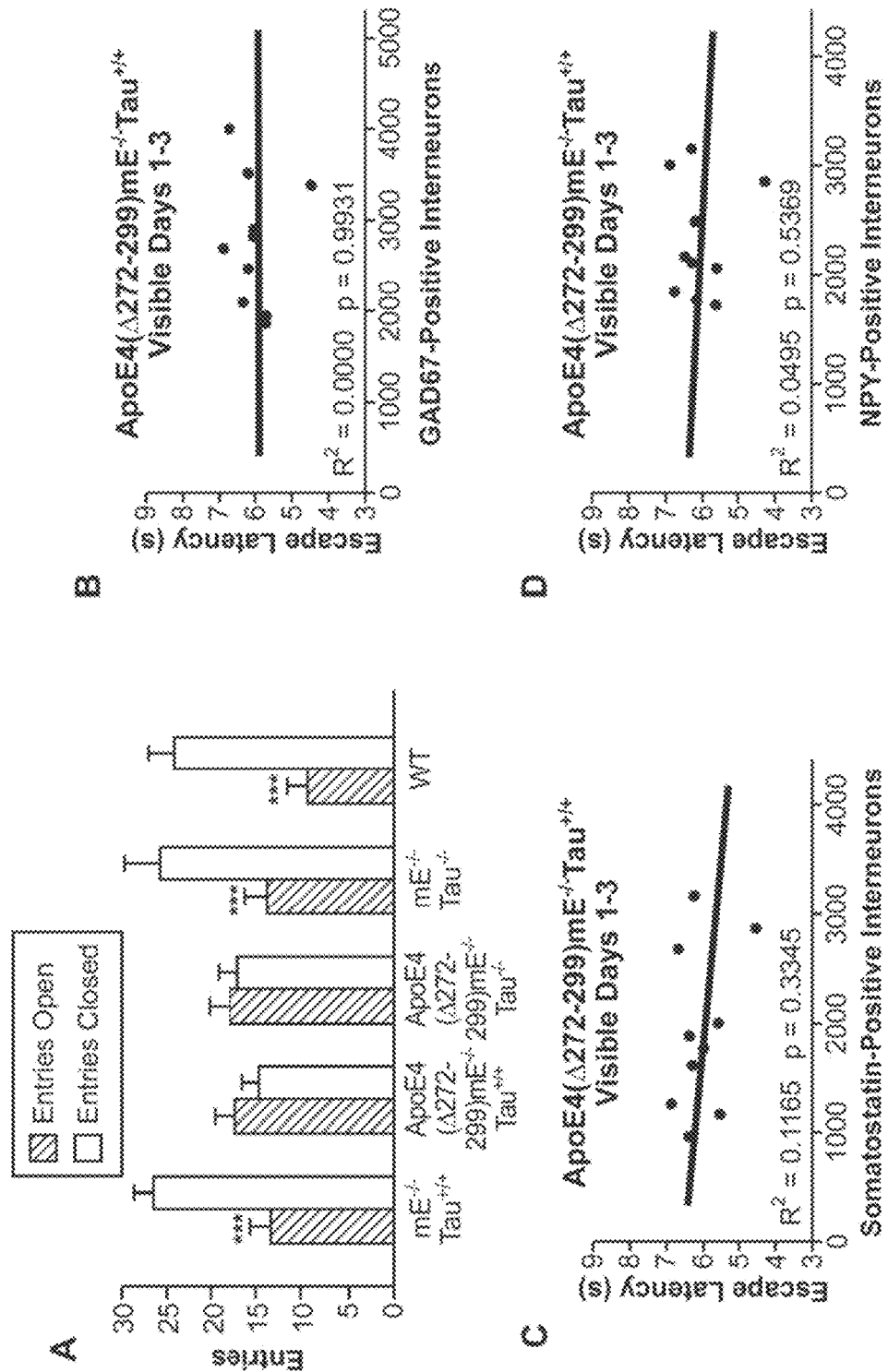
FIG. 10, panels A-H, depict: (A) the effect of eliminating tau on apoE4 fragment-caused abnormal anxiety in apoE4 (Δ272-299) mE$^{-/-}$Tau$^{+/+}$ mice; (B-D) performance in the cued platform trial and the number of hilar GABAergic interneurons in apoE4(Δ272-299) mE$^{-/-}$Tau$^{+/+}$ mice; (E) the effect of treatment with the GABAA receptor antagonist picrotoxin (Picro) on the number of hilar GABAergic interneurons in ApoE4(Δ272-299)mE$^{-/-}$Tau$^{-/-}$ mice; (F and G) the effect of treatment with a low dose of picrotoxin on the learning and memory performance in wildtype and mE$^{-/-}$Tau$^{+/+}$ mice; and (H) the effect of the GABAA receptor potentiator pentobarbital on the learning deficit in apoE4 (Δ272-299) mE$^{-/-}$Tau$^{+/+}$ mice.
Figure 10:
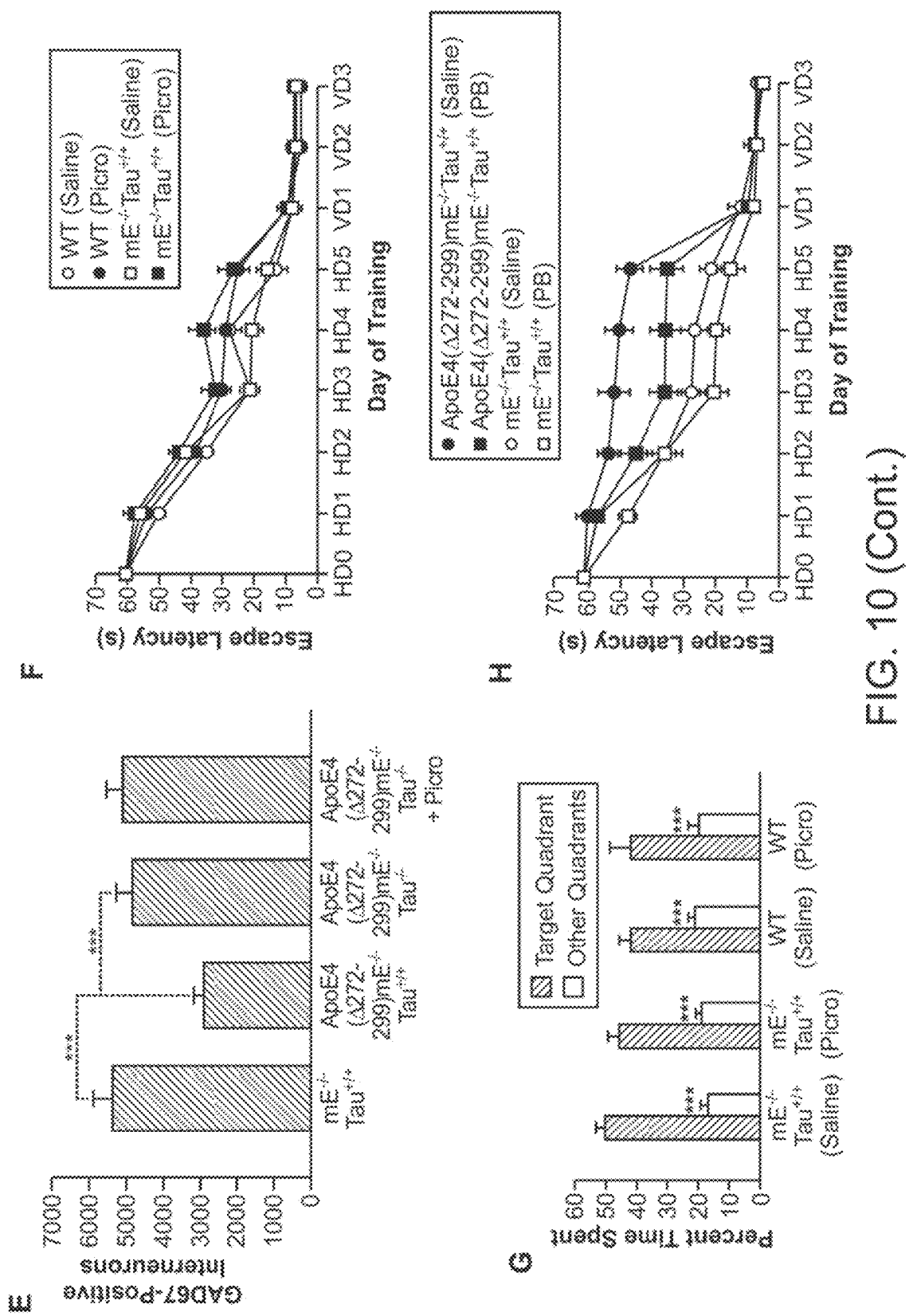

In apoE4(Δ272-299)mE–/–Tau+/+ mice, the number of GABAergic interneurons in the hilus correlated inversely with escape latency on days 1-5 of the hidden platform test (FIG. 8, panels D-F). Importantly, as in apoE4-KI mice (FIG. 3, panels C, E, and G), apoE4(Δ272-299)mE–/–Tau+/+ mice with fewer than 2500 hilar GABAergic interneurons had greater learning deficits in the hidden platform trials (FIG. 8, panels D-F), consistent with a threshold of 2500 hilar GABAergic interneurons for normal versus impaired learning performance in the MWM. The number of hilar GABAergic interneurons did not correlate with performance in visible platform trials in apoE4(Δ272-299)mE–/–Tau+/+ mice (FIG. 10, panels B-D).

Tau Removal Prevents ApoE4-Induced Learning and Memory Deficits by Protecting Against Hilar GABAergic Interneuron Impairment.

Finally, whether the rescue of learning and memory deficits by tau removal reflects protection against GABAergic interneuron impairment was determined. ApoE4(Δ272-299)mE–/–Tau–/– mice were treated with a subthreshold dose (1 mg/kg) of picrotoxin, a GABAA receptor antagonist, to block GABA signaling. The rescue was abolished (FIG. 8, panel G and H), but the number of hilar GABAergic interneurons was unaltered (FIG. 10, panel E). Picrotoxin at this dose did not alter learning and memory in wildtype or mE–/–Tau+/+ mice (FIG. 10, panels F and G). In contrast, treatment of apoE4(Δ272-299)mE–/– Tau+/+ mice with pentobarbital, a GABAA receptor potentiator, rescued the learning deficit (FIG. 10, panel H). Evidently, tau removal rescues apoE4 fragment-induced learning and memory deficits by preventing the loss of GABAergic interneurons.

FIG. 1. Age-Dependent Significant Decrease in Numbers of GABAergic Interneurons in the Hilus of Dentate Gyrus of Female ApoE4-KI Mice.

(A-D) Representative photomicrographs (200×) from female apoE3-KI and apoE4-KI mice at 16 months of age show GABAergic interneurons in the hilus after staining with anti-GAD67 (A and B) and anti-somatostatin (C and D). (E and F) Hilar GABAergic interneurons positive for GAD67 (E) or somatostatin (F) in female apoE3-KI and apoE4-KI mice at 1, 3, 6, 12, 16, and 21 months of age (n=4-12 mice per group) were quantified as described in Experimental Procedures. Values are mean±SEM. *p<0.05; **p<0.01 (t test). (G and H) Representative photomicrographs (200×) show GABAergic interneurons in CA1 region of the hippocampus after staining with anti-GAD67. (I) Quantification of GAD67-positive GABAergic interneurons in CA1 region of the hippocampus in 16-month-old female apoE3-KI (n=10) and apoE4-KI (n=12) mice. Values are mean±SEM.

FIG. 2. Presynaptic GABAergic Input onto Granule Cells is Reduced in Female ApoE4-KI Mice.

(A-F) Representative confocal images of the granule cell layer of the dentate gyrus of female apoE3-KI (A-C) and apoE4-KI (D-F) mice at 16 months of age stained with anti-GAD67 (A and D) and anti-synaptophysin (B and E). Merged images are shown in panels C and F. (G) GAD67 immunoreactivity (IR) of sections from different mice was quantified and normalized by area. Values are mean±SEM (four images per mouse and 4-5 mice per genotype). *p<0.005 versus apoE3-KI mice (t test). (H) The ratio of GAD67-IR to synaptophysin-IR (a general presynaptic marker) in sections from different mice. Values are mean±SEM (four images per mouse and 4-5 mice per genotype). *p<0.005 vs. apoE3-KI mice (t test). (I and J) Traces of miniature inhibitory postsynaptic currents (mIPSCs) in granule cells from apoE3-KI (I) or apoE4-KI (J) mice during whole-cell voltage clamp recording in the presence of DNQX (20 µM), D-AP5 (50 µM), and TTX (1 µM). Scale bars, 20 pA and 700 ms. (K) Average mIPSC frequency in granule cells was lower in apoE4-KI mice than in apoE3-KI mice. Values are mean±SEM (n=9-10 cells per genotype). **p<0.01 versus apoE3-KI mice (t test). (L) Average mIPSC amplitude in granule cells was similar in apoE3-KI and apoE4-KI mice. Values are mean±SEM (n=9-10 cells per genotype). (M) Average membrane resistance of granule cells was similar in apoE3-KI and apoE4-KI mice. Values are mean±SEM (n=8-11 cells per genotype).

FIG. 3. Correlation of Hilar GABAergic Interneuron Impairment with Spatial Learning Deficits in ApoE4-KI Mice.

(A) Ten apoE3-KI and 12 apoE4-KI female mice were tested at 16 months of age in the MWM. Points represent averages of daily trials. HD, hidden platform day (two trials/session, two sessions/day); HD0, first trial on HD1; VD, visible platform day (two trials/session, two sessions/day). Y-axis indicates time to reach the target platform (escape latency, mean±SEM). In the hidden platform days, learning curves differed significantly by genotypes (p<0.01, repeated-measures ANOVA). (B) The probe trials of female apoE3-KI and apoE4-KI mice at 16 months of age were performed 72 h (probe 2) and 96 h (probe 3) after the last hidden platform training. Percent time spent in the target quadrant versus the other quadrants differed by genotype in probe 3 (p<0.05). Values are mean±SEM. *p<0.05, ***p<0.005 (t test). (C and D) Escape latency in hidden platform days 1-5 correlated inversely with the number of GAD67-positive hilar GABAergic interneurons in apoE4-KI mice (C, n=12) but not apoE3-KI mice (D, n=10) at 16 months of age. (E and F) Escape latency in hidden platform days 1-5 correlated inversely with the number of somatostatin-positive hilar GABAergic interneurons in apoE4-KI mice (E, n=12) but not apoE3-KI mice (F, n=10) at 16 months of age. (G and H) Eight apoE3-KI and eight apoE4-KI female mice were tested at 21 months of age in the MWM. Escape latency in hidden platform days 1-5 correlated inversely with the number of somatostatin-positive hilar GABAergic interneurons in apoE4-KI mice (G, n=8) but not apoE3-KI mice (H, n=8) at 21 months of age.

FIG. 4. GABAA Receptor Potentiator Pentobarbital Rescues Spatial Learning and Memory Deficits in ApoE4-KI Mice.

(A) Female 16-month-old apoE4-KI mice were treated with pentobarbital (PB, 20 mg/kg i.p.) or saline (n=6-13 per group) for 21 days before and daily during the MWM test. Untreated apoE3-KI mice (n=10) served as controls. The learning curve of pentobarbital-treated apoE4-KI mice differed from that of saline-treated apoE4-KI mice (p<0.05, repeated-measures ANOVA) but resembled that of untreated apoE3-KI mice. Values are mean±SEM. HD, hidden day; VD, visible day. (B) In the probe trial 96 h after the last hidden session, pentobarbital treatment rescued memory deficits in 16-month-old apoE4-KI mice in the target quadrant and target cross tests (n=6-13 mice/group). Values are mean±SEM. *p<0.005 (t test). (C) Total number of GAD67-positive GABAergic interneurons in the hilus of apoE3-KI mice, apoE4-KI mice, and apoE4-KI mice treated with pentobarbital. Values are mean±SEM. p<0.01, ***p<0.005 vs. apoE3-KI mice (t test). (D) Female 21-month-old apoE4-KI mice were treated with pentobarbital (PB, 20 mg/kg) or saline (n=8 per group) for 21 days before and daily during the MWM test. Saline-treated apoE3-KI mice (n=8) served as controls. The learning curve of pentobarbital-treated apoE4-KI mice differed from that of saline-treated apoE4-KI mice (p<0.05, repeated-measures ANOVA) but resembled that of saline-treated apoE3-KI mice. Values are mean±SEM. HD, hidden day; VD, visible day.

FIG. 5. Localization of apoE4(Δ272-299) in the Hippocampus and its Effects on Neurodegeneration and Tau Pathology in the Presence and Absence of Tau.

(A-D) Double immunofluorescence staining for apoE (green) and NeuN (red) in the hippocampus of apoE4(Δ272-299)mE−/−Tau+/+ mice (magnification: A, 100×; B, C, and D 400×). (E) Double immunofluorescence staining for apoE (green) and synaptophysin (Syn, red) in the CA3 region of apoE4(Δ272-299)mE−/−Tau+/+ mice (600×). (F) Double immunofluorescence staining for apoE (green) and MAP2 (red) in the CA3 region of apoE4(Δ272-299)mE−/−Tau+/+ mice (magnification, 600×). (G and H) Hematoxylin-eosin (HE) staining of the dentate gyrus of apoE4(Δ272-299) mE−/− Tau+/+ (G) and wildtype (H) mice (magnification, 200×). (I-K) Immunofluorescence staining for MAP2 in the hilus of the dentate gyrus of apoE4(Δ272-299)mE−/−Tau+/+ (I), wildtype (J), and apoE4(Δ272-299)mE−/−Tau−/− (K) mice (magnification, 200×). (L-N) Anti-p-tau (AT8 monoclonal antibody) immunostaining of the hilus of apoE4 (Δ272-299)mE−/−Tau+/+(L), mE−/−Tau+/+(M), and apoE4 (Δ272-299)mE−/− Tau−/− (N) mice (magnification, 400×). (O and P) Anti-p-tau (AT8 monoclonal antibody) immunostaining of the CA3 region (O) of the hippocampus and the subiculum (P) of apoE4(Δ272-299)mE−/−Tau+/+ mice (magnification, 400×). All mice were 11-13 months of age.

FIG. 6. Loss of GABAergic Interneurons in the Hilus of the Dentate Gyrus of ApoE4(Δ272-299)mE−/−Tau+/+ Mice and Rescue by Tau Removal.

The brains of 14 mE−/−Tau+/+, 10 apoE4(Δ272-299) mE−/−Tau+/+, 12 apoE4(Δ272-299)mE−/−Tau−/−, eight mE−/−Tau−/−, and 16 wildtype mice (all females) were collected at 12 months of age after behavioral assessment, sectioned, and immunostained with antibodies against GAD67, neuropeptide Y (NPY), or somatostatin. (A-O) Photomicrographs (200×) of GABAergic interneurons in the hilus after staining with anti-GAD67 (A-E), anti-NPY (F-J), or anti-somatostatin (K-O). (P-R) Total number of GAD67-positive (P), NPY-positive (Q), and somatostatin-positive (R) GABAergic interneurons in the hilus. Values are mean±SEM. ***p<0.005 (t test).

FIG. 7. Eliminating Tau Prevents the Neurotoxic Effect of ApoE4 Fragments on Primary Hippocampal GABAergic Neurons.

(A-D) Primary hippocampal neurons from individual P0 pups (mE−/−Tau+/+, apoE4(Δ272-299)mE−/− Tau+/+, apoE4(Δ272-299)mE−/−Tau−/−, and mE−/−Tau−/−) were cultured for 14 days in vitro (DIV14) and double stained with anti-GAD67 (green) and DAPI (blue). Shown are representative images collected from three mice of each genotype and five fields per coverslip (magnification, 200×). (E) Numbers of GAD67-positive neurons were quantified as described in Experimental Procedures. Values are mean±SEM. p<0.01, *p<0.005 (t test).

FIG. 8. Spatial Learning and Memory Deficits in ApoE4 (Δ272-299)mE−/− Tau+/+ Mice and Rescue by Tau Removal.

(A) Fourteen mE−/−Tau+/+, 10 apoE4(Δ272-299)mE−/− Tau+/+, 12 apoE4(Δ272-299)mE−/−Tau−/−, eight mE−/−

Tau−/−, and 16 wildtype mice (all females) were tested at 12 months of age in the MWM. Values are mean±SEM. In the hidden platform days, learning curves differed significantly by genotype (p<0.001, repeated-measures ANOVA). In post-hoc comparisons, apoE4(Δ272-299)mE−/−Tau+/+ mice learned poorly (p<0.01 vs. other groups). ApoE4 (Δ272-299)mE−/−Tau−/−, mE−/−Tau+/+, and wildtype mice performed at a similar level. (B) In the probe trial 24 h after the last hidden platform training, the number of target platform crossings versus crossings of the equivalent area in the other quadrants differed by genotype (p<0.05). In post-hoc comparisons, apoE4(Δ272-299)mE−/−Tau−/− mice performed better than apoE4(Δ272-299)mE−/−Tau+/+ mice (p<0.01) in the target crossing test. Only apoE4(Δ272-299) mE−/−Tau+/+ mice showed impaired memory in the probe trail, and the deficit was rescued by tau removal. Values are mean±SEM. *p<0.005. (C) In the probe trial 24 h after the last hidden platform training, the time spent in the target quadrant versus the other quadrants differed by genotypes (p<0.01). In post-hoc comparisons, only apoE4(Δ272-299) mE−/−Tau+/+ mice showed impaired memory in the probe test, and the deficit was rescued by tau removal. Values are mean±SEM. *p<0.005. (D-F) Latency on hidden days 1-5 correlated inversely with the number of GAD67-positive (D), somatostatin-positive (E), and NPY-positive (F) GABAergic interneurons in the hilus in apoE4(Δ272-299) mE−/−Tau+/+ mice. n=10 per analysis. (G) ApoE4(Δ272-299)mE−/−Tau−/− mice were treated with picrotoxin (Picro, 1 mg/kg i.p.) or saline (n=6-8 per group) for 3 days before and daily during the MWM test. Saline-treated apoE4(Δ272-299)mE−/−Tau+/+ and mE−/−Tau+/+ mice (n=6-8 per group) served as controls. The learning curve of picrotoxin-treated apoE4(Δ272-299)mE−/−Tau−/− mice resembled that of saline-treated apoE4(Δ272-299)mE−/−Tau+/+ mice, which differed significantly from those of saline-treated controls (p<0.01). Values are mean±SEM. (H) In the probe trial 24 h after the last hidden session, picrotoxin-treated apoE4(Δ272-299)mE−/−Tau−/− mice performed significantly worse than saline-treated apoE4(Δ272-299)mE−/−Tau−/− (p<0.05) or mE−/−Tau+/+ mice (p<0.01) in the target crossing test. n=6-8 mice per group. Values are mean±SEM. *p<0.05, **p<0.01.

FIG. 9. Performance in the Cued Platform Trial does not Correlate with the Number of Hilar GABAergic Interneurons in apoE3-KI and apoE4-KI Mice at 16 and 21 Months of Age.

Ten apoE3-KI and 12 apoE4-KI mice at 16 months of age and eight apoE3-KI and eight apoE4-KI mice at 21 months of age (all females) were tested in the MWM. (A and B) Performance in the cued platform trial did not correlate with the number of GAD67-positive GABAergic interneurons in apoE4-KI mice (A, n=12) or apoE3-KI mice (B, n=10) at 16 months of age. (C and D) Performance in the cued platform trial did not correlate with the number of somatostatin-positive GABAergic interneurons in apoE4-KI mice (C, n=12) or apoE3-KI mice (D, n=10) at 16 months of age. (E and F) Performance in the cued platform trial did not correlate with the number of somatostatinpositive GABAergic interneurons in apoE4-KI mice (E, n=8) or apoE3-KI mice (F, n=8) at 21 months of age.

FIG. 10. (A) Eliminating tau does not rescue apoE4 fragment-caused abnormal anxiety in apoE4(Δ272-299) mE−/−Tau+/+ mice. Nine mE−/−Tau+/+, 10 apoE4(Δ272-299)mE−/−Tau+/+, 12 apoE4(Δ272-299)mE−/−Tau−/−, six mE−/−Tau−/−, and eight wildtype mice (all females), were tested in an elevated plus maze at 12 months of age. Values are mean±SEM. *p<0.001 (t test). (B-D) Ten female apoE4(Δ272-299)mE−/−Tau+/+ were tested at 12 months of age in the MWM. Performance in the cued platform trial did not correlate with the number of GAD67-positive (B), somatostatin-positive (C), or NPY-positive (D) hilar GABAergic interneurons in apoE4(Δ272-299)mE−/−Tau+/+ mice. (E) Treatment with the GABAA receptor antagonist picrotoxin (Picro) does not alter the number of hilar GABAergic interneurons in ApoE4(Δ272-299)mE−/−Tau−/− mice. Female apoE4(Δ272-299)mE−/−Tau−/− mice at 12 months of age were treated with picrotoxin (Picro, 1 mg/kg i.p.) or saline (n=6-8 per group) for 3 days before the MWM test and every day during the test. Age-matched, saline-treated apoE4(Δ272-299)mE−/−Tau+/+ and mE−/−Tau+/+ mice (n=6-8 per group) served as controls. Total number of GAD67-positive interneurons in the hilus was quantified after the behavioral test. Values are mean±SEM. *p<0.005 (t test). (F and G) Treatment with a low dose of picrotoxin does not alter the learning and memory performance in wildtype and mE−/−Tau+/+ mice. Female wildtype and mE−/−Tau+/+ mice at 12 months of age were treated with intraperitoneal injections of picrotoxin (Picro, 1 mg/kg) or saline (n=8 per group) for 3 days before the MWM test and every day during the test. Age-matched, saline-treated wildtype and mE−/−Tau+/+ mice (n=8 per group) served as controls. There was no significant difference among the learning curves (F). In the probe trial performed 24 h after the last hidden platform training, the time spent in the target quadrant versus the other quadrants does not differ by genotypes or treatment (G). Values are mean±SEM. ***p<0.005 (t test). (H) Treatment with GABAA receptor potentiator pentobarbital rescues the learning deficit in apoE4(Δ272-299)mE−/−Tau+/+ mice. Female mE−/−Tau+/+ and apoE4(Δ272-299)mE−/−Tau+/+ mice at 12 months of age were treated with intraperitoneal injections of pentobarbital (PB, 20 mg/kg) or saline (n=7-9 per group) for 21 days before the MWM test and every day during the test. In the hidden platform sessions, learning curves differed significantly by genotype and treatment (p<0.01, repeated-measures ANOVA). In post-hoc comparisons, apoE4(Δ272-299)mE−/−Tau+/+ mice learned poorly versus mE−/−Tau+/+ mice (p<0.005). ApoE4(Δ272-299)mE−/−Tau+/+ mice treated with pentobarbital learned better than saline-treated apoE4(Δ272-299)mE−/−Tau+/+ mice (p<0.01). Values are mean±SEM.

REFERENCES

Bareggi, S. R., Franceschi, M., Bonini, L., Zecca, L., and Smirne, S. (1982). Decreased CSF concentrations of homovanillic acid and γ-aminobutyric acid in Alzheimer's disease. Age- or disease-related modifications? Arch Neurol 39, 709-712.

Bell, R. D., and Zlokovic, B. V. (2009). Neurovascular mechanisms and blood-brain barrier disorder in Alzheimer's disease. Acta Neuropathol 118, 103-113.

Bour, A., Grootendorst, J., Vogel, E., Kelche, C., Dodart, J.-C., Bales, K., Moreau, P.-H., Sullivan, P. M., and Mathis, C. (2008). Middle-aged human apoE4 targeted-replacement mice show retention deficits on a wide range of spatial memory tasks. Behavioral Brain Res 193, 174-182.

Brecht, W. J., Harris, F. M., Chang, S., Tesseur, I., Yu, G.-Q., Xu, Q., Fish, J. D., Wyss-Coray, T., Buttini, M., Mucke, L., et al. (2004). Neuron-specific apolipoprotein E4 proteolysis is associated with increased tau phosphorylation in brains of transgenic mice. J Neurosci 24, 2527-2534.

Brosh, I., and Barkai, E. (2009). Learning-induced enhancement of feedback inhibitory synaptic transmission. Learn Mem 16, 413-416.

Brunden, K. R., Trojanowski, J. Q., and Lee, V. M. Y. (2009). Advances in tau-focused drug discovery for Alzheimer's disease and related tauopathies. Nat Rev Drug Discov 8, 783-793.

Bu, G. (2009). Apolipoprotein E and its receptors in Alzheimer's disease: pathways, pathogenesis and therapy. Nat Rev Neurosci 10, 333-344.

Caselli, R. J., Dueck, A. C., Osborne, D., Sabbagh, M. N., Connor, D. J., Ahern, G. L., Baxter, L. C., Rapcsak, S. Z., Shi, J., Woodruff, B. K., et al. (2009). Longitudinal modeling of age-related memory decline and the APOE ε 4 effect. N Engl J Med 361, 255-263.

Corder, E. H., Saunders, A. M., Strittmatter, W. J., Schmechel, D. E., Gaskell, P. C., Small, G. W., Roses, A. D., Haines, J. L., and Pericak-Vance, M. A. (1993). Gene dose of apolipoprotein E type 4 allele and the risk of Alzheimer's disease in late onset families. Science 261, 921-923.

Crowther, R. A. (1993). Tau protein and paired helical filaments of Alzheimer's disease. Curr Opin Struct Biol 3, 202-206.

Cui, Y., Costa, R. M., Murphy, G. G., Elgersma, Y., Zhu, Y., Gutmann, D. H., Parada, L. F., Mody, I., and Silva, A. J. (2008). Neurofibromin regulation of ERK signaling modulates GABA release and learning. Cell 135, 549-560.

Davies, P., Katzman, R., and Terry, R. D. (1980). Reduced somatostatin-like immunoreactivity in cerebral cortex from cases of Alzheimer disease and Alzheimer senile dementia. Nature 288, 279-280.

Dawson, H. N., Ferreira, A., Eyster, M. V., Ghoshal, N., Binder, L. I., and Vitek, M. P. (2001). Inhibition of neuronal maturation in primary hippocampal neurons from tau deficient mice. J Cell Sci 114, 1179-1187.

Dennis, N. A., Browndyke, J. N., Stokes, J., Need, A., Burke, J. R., Welsh-Bohmer, K. A., and Cabeza, R. (2009). Temporal lobe functional activity and connectivity in young adult APOE e4 carriers. Alzheimers Dement 5, 1-9.

Farrer, L. A., Cupples, L. A., Haines, J. L., Hyman, B., Kukull, W. A., Mayeux, R., Myers, R. H., Pericak-Vance, M. A., Risch, N., and Van Duijn, C. M. (1997). Effects of age, sex, and ethnicity on the association between apolipoprotein E genotype and Alzheimer disease. A meta-analysis. J Am Med Assoc 278, 1349-1356.

Filippini, N., Macintosh, B. J., Hough, M. G., Goodwin, G. M., Frisoni, G. B., Smith, S. M., Matthews, P. M., Beckmann, C. F., and Mackay, C. E. (2009). Distinct patterns of brain activity in young carriers of the APOE-ε4 allele. Proc Natl Acad Sci USA 106, 7209-7214.

Götz, J., Chen, F., van Dorpe, J., and Nitsch, R. M. (2001). Formation of neurofibrillary tangles in P301L tau transgenic mice induced by Ab42 fibrils. Science 293, 1491-1495.

Grouselle, D., Winsky-Sommerer, R., David, J. P., Delacourte, A., Dournaud, P., and Epelbaum, J. (1998). Loss of somatostatin-like immunoreactivity in the frontal cortex of Alzheimer patients carrying the apolipoprotein epsilon 4 allele. Neurosci Lett 255, 21-24.

Hardy, J., Cowburn, R., Barton, A., Reynolds, G., Dodd, P., Wester, P., O"Carroll, A. M., Lofdahl, E., and Winblad, B. (1987). A disorder of cortical CABAergic innervation in Alzheimer's disease. Neurosi Lett 73, 192-196.

Hardy, J., and Selkoe, D. J. (2002). The amyloid hypothesis of Alzheimer's disease: Progress and problems on the road to therapeutics. Science 297, 353-356.

Harris, F. M., Brecht, W. J., Xu, Q., Mahley, R. W., and Huang, Y. (2004a). Increased tau phosphorylation in apolipoprotein E4 transgenic mice is associated with activation of extracellular signal-regulated kinase: Modulation by zinc. J Biol Chem 279, 44795-44801.

Harris, F. M., Brecht, W. J., Xu, Q., Tesseur, I., Kekonius, L., Wyss-Coray, T., Fish, J. D., Masliah, E., Hopkins, P. C., Scearce-Levie, K., et al. (2003). Carboxyl-terminal-truncated apolipoprotein E4 causes Alzheimer's disease-like neurodegeneration and behavioral deficits in transgenic mice. Proc Natl Acad Sci USA 100, 10966-10971.

Harris, F. M., Tesseur, I., Brecht, W. J., Xu, Q., Mullendorff, K., Chang, S., Wyss-Coray, T., Mahley, R. W., and Huang, Y. (2004b). Astroglial regulation of apolipoprotein E expression in neuronal cells. Implications for Alzheimer's disease. J Biol Chem 279, 3862-3868.

Hartman, R. E., Wozniak, D. F., Nardi, A., Olney, J. W., Sartorius, L., and Holtzman, D. M. (2001). Behavioral phenotyping of GFAP-apoE3 and -apoE4 transgenic mice: ApoE4 mice show profound working memory impairments in the absence of Alzheimer's-like neuropathology. Exp Neurol 170, 326-344.

Herz, J., and Beffert, U. (2000). Apolipoprotein E receptors: Linking brain development and Alzheimer's disease. Nat Rev Neurosci 1, 51-58.

Hoe, H. S., and Rebeck, G. W. (2008). Functional interactions of APP with the apoE receptor family. J Neurochem 106, 2263-2271.

Hu, J. H., Ma, Y. H., Jiang, J., Yang, N., Duan, S. H., Jiang, Z. H., Mei, Z. T., Fei, J., and Guo, L. H. (2004). Cognitive impairment in mice over-expressing gamma-aminobutyric acid transporter 1 (GAT1) Neuroreport 15, 9-12.

Huang, Y. (2006a). Apolipoprotein E and Alzheimer disease. Neurology 66 (Suppl. 1), S79-S85.

Huang, Y. (2006b). Molecular and cellular mechanisms of apolipoprotein E4 neurotoxicity and potential therapeutic strategies. Curr Opin Drug Discov Dev 9, 627-641.

Huang, Y., Liu, X. Q., Wyss-Coray, T., Brecht, W. J., Sanan, D. A., and Mahley, R. W. (2001). Apolipoprotein E fragments present in Alzheimer's disease brains induce neurofibrillary tangle-like intracellular inclusions in neurons. Proc Natl Acad Sci USA 98, 8838-8843.

Irizarry, M. C., Rebeck, G. W., Cheung, B., Bales, K., Paul, S. M., Holtzman, D. M., and Hyman, B. T. (2000). Modulation of Aβ deposition in APP transgenic mice by an apolipoprotein E null background. Ann N Y Acad Sci 920, 171-178.

Jasinska, M., Siucinska, E., Cybulska-Klosowicz, A., Pyza, E., Furness, D. N., Kossut, M., and Glazewski, S. (2010). Rapid, learning-induced inhibitory synaptogenesis in murin barrel field. J Neurosci 30, 1176-1184.

Kim, J., Basak, J. M., and Holtzman, D. M. (2009). The role of apolipoprotein E in Alzheimer's disease. Neuron 63, 287-303.

Lewis, J., Dickson, D. W., Lin, W.-L., Chisholm, L., Corral, A., Jones, G., Yen, S.-H., Sahara, N., Skipper, L., Yager, D., et al. (2001). Enhanced neurofibrillary degeneration in transgenic mice expressing mutant tau and APP. Science 293, 1487-1491.

Li, G., Bien-Ly, N., Andrews-Zwilling, Y., Xu, Q., Bernardo, A., Ring, K., Halabisky, B., Deng, C., Mahley, R. W., and Huang, Y. (2009). GABAergic interneuron dysfunction impairs hippocampal neurogenesis in adult apolipoprotein E4 knockin mice. Cell Stem Cell 5, 634-645.

Mahley, R. W. (1988). Apolipoprotein E: Cholesterol transport protein with expanding role in cell biology. Science 240, 622-630.

Mahley, R. W., Weisgraber, K. H., and Huang, Y. (2006). Apolipoprotein E4: A causative factor and therapeutic target in neuropathology, including Alzheimer's disease. Proc Natl Acad Sci USA 103, 5644-5651.

Namba, Y., Tomonaga, M., Kawasaki, H., Otomo, E., and Ikeda, K. (1991). Apolipoprotein E immunoreactivity in cerebral amyloid deposits and neurofibrillary tangles in Alzheimer's disease and kuru plaque amyloid in Creutzfeldt-Jakob disease. Brain Res 541, 163-166.

Nitz, D., and McNaughton, B. (2004). Differential modulation of CA1 and dentate gyrus interneurons during exploration of novel environments. Am Physiol Soc 91, 863-872.

Palop, J. J., and Mucke, L. (2009). Epilepsy and cognitive impairments in Alzheimer disease. Neurol Rev 66, 435-440.

Perrin, R. J., Fagan, A. M., and Holztman, D. M. (2009). Multimodal techniques for diagnosis and prognosis of Alzheimer's disease. Nature 461, 917-922.

Raber, J., Wong, D., Buttini, M., Orth, M., Bellosta, S., Pitas, R. E., Mahley, R. W., and Mucke, L. (1998). Isoform-specific effects of human apolipoprotein E on brain function revealed in ApoE knockout mice: Increased susceptibility of females. Proc Natl Acad Sci USA 95, 10914-10919.

Raber, J., Wong, D., Yu, G.-Q., Buttini, M., Mahley, R. W., Pitas, R. E., and Mucke, L. (2000). Apolipoprotein E and cognitive performance. Nature 404, 352-354.

Rapoport, M., Dawson, H. N., Binder, L. I., Vitek, M. P., and Ferreira, A. (2002). Tau is essential to b-amyloid-induced neurotoxicity. Proc Natl Acad Sci USA 99, 6364-6369.

Roberson, E. D., Scearce-Levie, K., Palop, J. J., Yan, F., Cheng, I. H., Wu, T., Gerstein, H., Yu, G.-Q., and Mucke, L. (2007). Reducing endogenous tau ameliorates amyloid β-induced deficits in an Alzheimer's disease mouse model. Science 316, 750-754.

Seidl, R., Cairns, N., Singewald, N., Kaehler, S. T., and Lubec, G. (2001). Differences between GABA levels in Alzheimer's disease and Down syndrome with Alzheimer-like neuropathology. Naunyn Schmiedeberg Arch Pharmacol 363, 139-145.

Selkoe, D. J. (1991). The molecular pathology of Alzheimer's disease. Neuron 6, 487-498.

Small, S. A., and Duff, K. (2008). Linking Aβ and tau in late-onset Alzheimer's disease: A dual pathway hypothesis. Neuron 60, 534-542.

Strittmatter, W. J., Saunders, A. M., Goedert, M., Weisgraber, K. H., Dong, L.-M., Jakes, R., Huang, D. Y., Pericak-Vance, M., Schmechel, D., and Roses, A. D. (1994). Isoform-specific interactions of apolipoprotein E with microtubule-associated protein tau: Implications for Alzheimer disease. Proc Natl Acad Sci USA 91, 11183-11186.

Strittmatter, W. J., Saunders, A. M., Schmechel, D., Pericak-Vance, M., Enghild, J., Salvesen, G. S., and Roses, A. D. (1993). Apolipoprotein E: High-avidity binding to b-amyloid and increased frequency of type 4 allele in late-onset familial Alzheimer disease. Proc Natl Acad Sci USA 90, 1977-1981.

Sullivan, P. M., Mace, B. E., Maeda, N., and Schmechel, D. E. (2004). Marked regional differences of brain human apolipoprotein E expression in targeted replacement mice. Neuroscience 124, 725-733.

Tanzi, R. E., and Bertram, L. (2001). New frontiers in Alzheimer's disease genetics. Neuron 32, 181-184.

Tesseur, I., Van Dorpe, J., Bruynseels, K., Bronfman, F., Sciot, R., Van Lommel, A., and Van Leuven, F. (2000a). Prominent axonopathy and disruption of axonal transport in transgenic mice expressing human apolipoprotein E4 in neurons of brain and spinal cord. Am J Pathol 157, 1495-1510.

Tesseur, I., Van Dorpe, J., Spittaels, K., Van den Haute, C., Moechars, D., and Van Leuven, F. (2000b). Expression of human apolipoprotein E4 in neurons causes hyperphosphorylation of protein tau in the brains of transgenic mice. Am J Pathol 156, 951-964.

Vepsalainen, S., Helisalmi, S., Koivisto, A. M., Tapaninen, T., Hiltunen, M., and Soininen, H. (2007). Somatostatin genetic variants modify the risk for Alzheimer's disease among Finnish patients. J Neurol 254, 1504-1508.

Weisgraber, K. H. (1994). Apolipoprotein E: Structure-function relationships. Adv Protein Chem 45, 249-302.

Wisniewski, T., and Frangione, B. (1992). Apolipoprotein E: A pathological chaperone protein in patients with cerebral and systemic amyloid. Neurosci Lett 135, 235-238.

Xu, Q., Walker, D., Bernardo, A., Brodbeck, J., Balestra, M. E., and Huang, Y. (2008). Intron-3 retention/splicing controls neuronal expression of apolipoprotein E in the CNS. J Neurosci 28, 1452-1459.

Xue, S., Jia, L., and Jia, J. (2009). Association between somatostatin gene polymorphisms and sporadic Alzheimer's disease in Chinese population. Neurosci Lett 465, 181-183.

Zhao, C., Deng, W., and Gage, F. H. (2008). Mechanisms and functional implications of adult neurogenesis. Cell 132, 645-660.

Zhong, N., and Weisgraber, K. H. (2009). Understanding the association of apolipoprotein E4 with Alzheimer's disease: Clues from its structure. J Biol Chem 284, 6027-6031.

Zimmer, R., Teelken, A. W., Trieling, W. B., Weber, W., Weihmayr, T., and Lauter, H. (1984). γ-Aminobutyric acid and homovanillic acid concentration in the CSF of patients with senile dementia of Alzheimer's type. Arch Neurol 41, 602-604.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of increasing the functionality of a GABAergic interneuron in the hilus of the hippocampus of an individual having at least one apolipoprotein E4 (apoE4) allele, the method comprising administering to the individual a tau-specific interfering nucleic acid that binds to a tau target and reduces the level of a tau polypeptide in the GABAergic interneuron, wherein the tau target is a contiguous stretch of at least 10 nucleotides of 5596-5807 of SEQ ID NO:2, wherein the tau-specific interfering nucleic acid is coupled to a carrier molecule that provides targeted delivery of the tau-specific interfering nucleic acid to the GABAergic interneuron.

2. The method of claim 1, wherein said tau-specific interfering nucleic acid is encoded by a nucleotide sequence operably lined to a neuron-specific transcriptional control element that is active in the GABAergic interneuron, wherein the nucleotide sequence is present in a recombinant expression vector.

3. The method of claim 1, wherein said administering is via a local route of administration.

4. The method of claim 3, wherein said administering is via intracranial administration.

5. The method of claim 1, wherein said increasing the functionality of a GABAergic interneuron results in an increase in cognitive function in the individual as determined by a cognitive assessment.

6. The method of claim 5, wherein said cognitive function is learning or memory.

7. The method of claim 1, wherein the carrier molecule is an antibody that specifically binds to the GABAergic interneuron.

* * * * *